US009745352B2

(12) United States Patent
Raman et al.

(10) Patent No.: US 9,745,352 B2
(45) **Date of Patent: *Aug. 29, 2017**

(54) INFLUENZA TREATMENT AND/OR CHARACTERIZATION, HUMAN-ADAPTED HA POLYPEPTIDES; VACCINES

(71) Applicant: Massachusetts Institute of Technology, Cambridge, MA (US)

(72) Inventors: Rahul Raman, Waltham, MA (US); Xiaoying Koh, Cambridge, MA (US); Karthik Viswanathan, Waltham, MA (US); Ram Sasisekharan, Bedford, MA (US); Aarthi Chandrasekaran, San Jose, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/341,285

(22) Filed: Jul. 25, 2014

(65) Prior Publication Data

US 2015/0147329 A1 May 28, 2015

Related U.S. Application Data

(63) Continuation of application No. 13/239,376, filed on Sep. 21, 2011, now Pat. No. 8,802,110.

(Continued)

(51) Int. Cl.
*A61K 39/145* (2006.01)
*C07K 14/005* (2006.01)
(Continued)

(52) U.S. Cl.
CPC ............ *C07K 14/005* (2013.01); *A61K 39/12* (2013.01); *A61K 39/145* (2013.01);
(Continued)

(58) Field of Classification Search
None
See application file for complete search history.

(56) References Cited

U.S. PATENT DOCUMENTS

| | | | |
|---|---|---|---|
| 4,166,452 | A | 9/1979 | Generales, Jr. |
| 4,270,537 | A | 6/1981 | Romaine |

(Continued)

FOREIGN PATENT DOCUMENTS

| | | |
|---|---|---|
| JP | 2010-500880 A | 1/2010 |
| JP | 2010-501074 A | 1/2010 |

(Continued)

OTHER PUBLICATIONS

Liu et al. Structures of receptor complexes formed by hemagglutinins from the Asian Influenza pandemic of 1957. Proc. Natl. Acad. Sci. 2009; 40: 17175-17180.*

(Continued)

*Primary Examiner* — Janet L Andres
*Assistant Examiner* — Stuart W Snyder
(74) *Attorney, Agent, or Firm* — Choate, Hall & Stewart LLP; Brenda Herschbach Jarrell; Cassandra Gianna Luca

(57) ABSTRACT

The present invention provides, among other things, methods, reagents, and systems for the treatment, detection, analysis, and/or characterization of influenza infections.

6 Claims, 42 Drawing Sheets

Related U.S. Application Data

(60) Provisional application No. 61/384,780, filed on Sep. 21, 2010.

(51) Int. Cl.

| | |
|---|---|
| ***A61K 39/12*** | (2006.01) |
| ***C07K 16/10*** | (2006.01) |
| ***C12N 7/00*** | (2006.01) |
| ***G01N 33/569*** | (2006.01) |

(52) U.S. Cl.

CPC ............ *C07K 16/1018* (2013.01); *C12N 7/00* (2013.01); *G01N 33/56983* (2013.01); *C12N 2760/16122* (2013.01); *C12N 2760/16133* (2013.01); *C12N 2760/16134* (2013.01); *G01N 2333/11* (2013.01)

(56) References Cited

U.S. PATENT DOCUMENTS

| | | | |
|---|---|---|---|
| 4,596,556 | A | 6/1986 | Morrow et al. |
| 4,692,411 | A | 9/1987 | Ghose |
| 4,790,824 | A | 12/1988 | Morrow et al. |
| 4,816,567 | A | 3/1989 | Cabilly et al. |
| 4,886,499 | A | 12/1989 | Cirelli et al. |
| 4,940,460 | A | 7/1990 | Casey, I. et al. |
| 4,941,880 | A | 7/1990 | Burns |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,417,662 | A | 5/1995 | Hjertman et al. |
| 5,466,220 | A | 11/1995 | Brenneman |
| 5,500,161 | A | 3/1996 | Andrianov et al. |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,649,912 | A | 7/1997 | Peterson |
| 5,698,390 | A | 12/1997 | Houghton et al. |
| 5,704,911 | A | 1/1998 | Parsons |
| 5,893,397 | A | 4/1999 | Peterson et al. |
| 5,993,412 | A | 11/1999 | Deily et al. |
| 8,802,110 | B2 | 8/2014 | Raman et al. |
| 2005/0009008 | A1 | 1/2005 | Robinson et al. |
| 2008/0241918 | A1 | 10/2008 | Sasisekharan et al. |
| 2009/0081193 | A1 | 3/2009 | Sasisekharan et al. |
| 2009/0269342 | A1 | 10/2009 | Sasisekharan et al. |
| 2010/0004195 | A1 | 1/2010 | Sasisekharan et al. |
| 2010/0061990 | A1 | 3/2010 | Sasisekharan et al. |
| 2011/0033490 | A1 | 2/2011 | Jayaraman et al. |
| 2012/0219585 | A1 | 8/2012 | Raman et al. |

FOREIGN PATENT DOCUMENTS

| | | | |
|---|---|---|---|
| WO | WO-9111465 | A1 | 8/1991 |
| WO | WO-9713537 | A1 | 4/1997 |
| WO | WO-9737705 | A1 | 10/1997 |
| WO | WO-9934850 | A1 | 7/1999 |
| WO | WO-0200885 | A2 | 1/2002 |
| WO | WO-2005020889 | A2 | 3/2005 |
| WO | WO-2006108226 | A1 | 10/2006 |
| WO | WO-2007130327 | A2 | 11/2007 |
| WO | WO-2007130330 | A2 | 11/2007 |
| WO | WO-2008005777 | A2 | 1/2008 |
| WO | WO-2008040060 | A1 | 4/2008 |
| WO | WO-2008054535 | A2 | 5/2008 |
| WO | WO-2008061243 | A2 | 5/2008 |
| WO | WO-2008/073161 | A2 | 6/2008 |
| WO | WO-2008094197 | A2 | 8/2008 |
| WO | WO-2008094200 | A2 | 8/2008 |
| WO | WO-2008148104 | A1 | 12/2008 |
| WO | WO-2009009876 | A1 | 1/2009 |
| WO | WO-2009012489 | A1 | 1/2009 |
| WO | WO-2009/089119 | A2 | 7/2009 |
| WO | WO-2009089121 | A2 | 7/2009 |
| WO | WO-2010006452 | A1 | 1/2010 |
| WO | WO-2010/093537 | A2 | 8/2010 |
| WO | WO-2012/040406 | A2 | 3/2012 |

OTHER PUBLICATIONS

Ekiert et al. Antibody Recognition of a Highly Conserved Influenza Virus Epitope. Science, 2009; 324: 246-251.*

Allison, A.C., The Mode of Action of Immunological Adjuvants, Dev. Biol. Stand., 92:3-11 (1998).

Altschul, S.F., et al., Basic Local Alignment Search Tool, J. Mol. Biol., 215(3):403-410 (1990).

Altschul, S.F., et al., Gapped BLAST and PSI-BLAST: a new generation of protein database search programs, Nucleic Acids Research, 25(17):3389-3402 (1997).

Altschul, S.F., et al., Local Alignment Statistics, Methods in Enzymology, 266(27):460-480.

Basler, C., et al., Influenza Viruses, Wiley Encyclopedia of Molecular Medicine, vol. 3, New York: John Wiley and Sons, pp. 1741-1747 (2002).

Baxevanis, A.D., et al., Bioinformatics : A Practical Guide to the Analysis of Genes and Proteins, Wiley, 1998.

Baylor, N.W., et al., Aluminum salts in vaccines—US perspective, Vaccine, 20:S18-S23 (2002).

Bresson, J.L., et al., Safety and immunogenicity of an inactivated split-virion influenza A/Vietnam/1194/2004 (H5N1) vaccine: phase I randomised trial, Lancet, 367:1657-1664 (2006).

Cao, M., et al., Enhancement of the protective effect of inactivated influenza virus vaccine by cytokines, Vaccine, 10(4):238-241 (1992).

Chandrasekaran, A., et al., Glycan topology determines human adaptation of avaian H5N1 virus hemagglutinin, Nature Biotechnology, 26:107-113 (2008).

Childs, R.A., et al., Receptor-binding specificity of pandemic influenza A (H1N1) 2009 virus determined by carbohydrate microarray, Nature Biotechnology, 27(9):797-799 (2009).

Connor, R.J., et al., Receptor Specificity in Human, Avian, and Equine H2 and H3 Influenza Virus Isolates, Virology, 205:17-23 (1994).

Cooper, C.L., et al., Safety and immunogenicity of CPG 7909 injection as an adjuvant to Fluarix influenza vaccine, Vaccine, 22:3136-3143 (2004).

Eisen, M.B., et al., Binding of the Influenza A Virus to Cell-Surface Receptors: Structures of Five Hemagglutinin-Sialyloligosaccharide Complexes Determined by X-Ray Crystallography, Virology, 232:19-31 (1997).

Enserink, M., ‘Pandemic Vaccine’ Appears to Protect Only at High Doses, Science, 309:996 (2005).

Fishwild, D.M., et al., High-avidity human IgGκ monoclonal antibodies from a novel strain of minilocus transgenic mice, Nature Biotechnology, 14(7):845-851 (1996).

Gambaryan, A.S., et al., Differences Between Influenza Virus Receptors on Target Cells of Duck and Chicken and Receptor Specificity of the 1997 H5N1 Chicken and Human Influenza Viruses from Hong Kong, Avian Diseases, 47:1154-1160 (2003).

Gamblin, S.J., et al., The Structure and Receptor Binding Properties of the 1918 Influenza Hemagglutinin, Science, 303:1838-1842 (2004).

GenBank record No. ABC66574.1 (GI:84797248), Influenza A virus (A/chicken/Bantul/BBVet-I/2005(H5N1)).

Ghockhikyan, A., et al., Prototype Alzheimer’s disease epitope vaccine induced strong Th2-type anti-Aβ antibody response with Alum to Quil A adjuvant switch, Vaccine, 24:2275-2282 (2006).

Glaser, L., et al., A Single Amino Acid Substitution in 1918 Influenza Virus Hemagglutinin Changes Receptor Binding Specificity, Journal of Virolology, 79(17):11533-11536 (2005).

(56) References Cited

OTHER PUBLICATIONS

Glaser, L., et al., Sequence analysis and receptor specificity of the hemagglutinin of a recent influenza H2N2 virus isolated from chicken in North America, Glycoconj J., 23:93-99 (2006).
Ha, Y., et al., X-ray structure of the hemagglutinin of a potential H3 avian progenitor of the 1968 Hong Kong pandemic influenza virus, Virology, 309:209-218 (2003).
Ha, Y., et al., X-ray structures of H5 avian and H9 swine influenza virus hemagglutinins bound to avian and human receptor analogs, PNAS, 98(20):11181-11186 (2001).
Harlow, E., et al., Antibodies: A Laboratory Manual, Cold Spring Harbor Laboratory (1988).
Hensley, S,E., et al., Hemagglutinin Receptor Binding Avidity Drives Influenza A Virus Antigenic Drift, Science, 326:734-736 (2009).
Hoogenboom, H.R., et al., Construction and Expression of Antibody-Tumor Necrosis Factor Fusion Proteins, Molecular Immunology, 28(9):1027-1037 (1991).
Imberty, A., et al., An Unusual Carbohydrate Binding Site Revealed by the Structures of Two Maackia amurensis Lectins Complexed with Sialic Acid-containing Oligosaccharides, Journal of Biological Chemistry, 275(23):17541-17548 (2000).
International Search Report of PCT/US11/52670, 6 pages (Mar. 23, 2012).
Itoh, Y., et al., In vitro and in vivo characterization of new swine-origin H1N1 influenza viruses, Nature, 460:1021-1025 (2009).
Jayasena, S.D., Aptamers: An Emerging Class of Molecules That Rival Antibodies in Diagnostics, Clinical Chemistry, 45(9):1628-1650 (1999).
Katz, J.M., et al., A nonionic block co-polymer adjuvant (CRL1005) enhances the immunogenicity and protective efficacy of inactivated influenza vaccine in young and aged mice, Vaccine, 18:2177-2187 (2000).
Kreuter, J., et al., Long-Term Studies of Microencapsulated and Adsorbed Influenza Vaccine Nanoparticles, Journal of Pharmaceutical Science, 70(4):367-371 (1981).
Liu, J., et al., Structures of receptor complexes formed by hemagglutinins from the Asian Influenza pandemic of 1957, PNAS, 106(40):17175-17180 (2009).
Lonberg, N., et al., Antigen-specific human antibodies from mice comprising four distinct genetic modifications, Nature, 368:856-859 (1994).
Lonberg, N., et al., Human Antibodies from Transgenic Mice, Intern. Rev. Immunol., 13(1):65-93 (1995).
Losman, M.J., et al., Baboon Anti-Idiotype Antibodies Mimic A Carcinoembryonic Antigen Epitope, Int. J. Cancer, 46:310-314 (1990).
Ma, W., et al., Identification of H2N3 influenza A viruses from swine in the United States, PNAS, 104(52):20949-20954 (2007).
Maines, T.,R., et al., Transmission and Pathogenesis of Swine-Origin 2009 A(H1N1) Influenza Viruses in Ferrets and Mice, Science, 325:484-487 (2009).
Maines, T.R., et al., Lack of transmission of H5N1 avian-human reassortant influenza viruses in a ferret model, PNAS, 103(32):12121-12126 (2006).
Makarova, N.V., et al., Transmission of Eurasian avian H2 influenza virus to shorebirds in North America, Journal of General Virology, 80:3167-3171 (1999).
Marks, J.D., et al., By-Passing Immunization: Building High Affinity Human Antibodies by Chain Shuffling, Biotechnology, 10:779-783 (1992).
Marks, J.D., et al., By-passing Immunization: Human Antibodies from V-gene Libraries Displayed on Phage, J. Mol. Biol., 222:581-597 (1991).
Matrosovich et al., Early Alterations of the Receptor-Binding Properties of H1, H2, and H3 Avian Influenza Virus Hemagglutinins after Their Introduction into Mammals, J. Virol., 74(18):8502-8512 (2000).
Mbwuike, I.N., et al., Enhancement of the protective efficacy of inactivated influenza A virus vaccine in aged mice by IL-2 liposomes, Vaccine, 8:347-352 (1990).
Milstein, C., et al., Hybrid hybridomas and their use in immunohistochemistry, Nature 305:537-540 (1983).
Misener, et al., (eds.), Bioinformatics Methods and Protocols (Methods in Molecular Biology, vol. 132), Humana Press, 1999.
Mostow, S.R., et al., Application of the Single Radial Diffusion Test for Assay of Antibody to Influenza Type A Viruses, Journal of Clinical Microbiology, 2(6):531-540 (1975).
NCBI website, protein Blast of GenBank record No. ABW74701.1 (GI:158604860), Influenza A virus (A/Indonesia/TLL001/2006(H5N1)), (<http://blast.ncbi.nlm.nih.gov/Blast.cigi>), Oct. 28, 2011.
Nicholson, K.G., et al., Textbook of Influenza, Blackwell Science, Malden, MA, 1998.
Pappas, C., et al., Receptor Specificity and Transmission of H2N2 Subtype Viruses Isolated from the Pandemic of 1957, PLoS ONE, 5(6):e11158 (10 pages) (2010).
Payne, L.G., et al., Poly[di(carboxylataphenoxy)phosphazene] (PCPP) is a potent immunoadjuvant for an influenza vaccine, Vaccine, 16(1):92-98 (1998).
Phillips, N.C., et al., Enhanced antibody response to liposome-associated protein antigens: preferential stimulation of IgG2a/b production, Vaccine, 10:151-158 (1992).
Reisfeld, R.A., et al., Human tumour-associated antigens: targets for monoclonal antibody-mediated cancer therapy, Cancer Surveys, 4(1):271-290 (1985).
Remington Pharmaceutical Sciences, 19th ed., Mack Publishing Co., Easton, PA, 1995.
Remington The Science and Practice of Pharmacy, 21st ed., Lippincott, Williams & Wilkins, Baltimore, MD, 2006.
Ribi, E., et al., Modulation of Humoral and Cell-Mediated Immune Response, Immunobiology and Immunopharmacology of Bacterial Endotoxins, 407-420 (1986).
Riechmann, L., et al., Reshaping human antibodies for therapy, Nature, 332:323-327 (1988).
Rogers, G.N., et al., Receptor Determinants of Human and Animal Influenza Virus Isolates: Differences in Receptor Specificity of the H3 Hemagglutinin Based on Species of Origin, Virology, 127:361-373 (1983).
Rogers, G.N., et al., Single amino acid substitutions in influenza haemagglutinin change receptor binding specificity, Nature, 304:76-78 (1983).
Russell, C.J., et al., The Genesis of a Pandemic Influenza Virus, Cell, 123:368-371 (2005).
Russell, R.J., et al., Avian and human receptor binding by hemagglutinins of influenza A viruses, Glyconconj J., 23:85-92 (2006).
Russell, R.J., et al., H1 and H7 influenza haemagglutinin structures extend a structural classification of haemagglutinin subtypes, Virology, 325:287-296 (2004).
Sambrook et al., Molecular Cloning: A Laboratory Manual, CSHL Press, Sections 7.71-7.77 (1989).
Sauter, N.K., et al., Binding of Influenza Virus Hemagglutinin to Analogs of Its Cell-Surface Receptor, Sialic Acid: Analysis by Proton Nuclear Magnetic Resonance Spectroscopy and X-ray Crystallography, Biochemistry, 31:9609-9621 (1992).
Schafer, J.R., et al., Origin of the Pandemic 1957 H2 Influenza A Virus and the Persistence of Its Possible Progenitors in the Avian Reservoir, Virology, 194 781-788 (1993).
Schild, G.C., et al., Single-radial-haemolysis: a new method for the assay of antibody to influenza haemagglutinin, Bull. World Health Organ., 52:43-50 & 223-31, (1975).
Shinya, K., et al., Influenza virus receptors in the human airway: Avian and human flu viruses seem to target different regions of a patent's respiratory tract, Nature, 440: 435-436 (2006).
Shriver, Z., et al., Context-Specific Target Definition in Influenza A Virus Hemagglutinin-Glycan Receptor Interactions, Chemistry & Biology, 16:803-814 (2009).
Skehel, J.J., et al., Receptor Binding and Membrane Fusion in Virus Entry: The Influenza Hemagglutinin, Annu. Rev. Biochem., 69:531-569 (2000).

(56) References Cited

OTHER PUBLICATIONS

Srinivasan, A., et al., Quantitative biochemical rationale for differences in transmissibility of 1918 pandemic influenza A viruses, PNAS, 105(8):2800-2805 (2008).
Stevens, J., et al., Recent avian H5H1 viruses exhibit increased propensity for acquiring human receptor specificity, J. Mol. Biol., 381(5):1382-1394 (2008).
Stevens, J., et al., Structure and Receptor Specificity of the Hemagglutinin from an H5H1 Influenza Virus, Science, 312:404-410 (2006).
Stevens, J., et al., Structure of the Uncleaved Human H1 Hemagglutinin from the Extinct 1918 Influenza Virus, Science, 303:1866-1870 (2004).
Stevens, J., et. al., Glycan Microarray Analysis of the Hemagglutinins from Modern and Pandemic Influenza Viruses Reveals Different Receptor Specificities, J. Mol. Biol., 355:1143-1155 (2006).
Stevens, J.M., et. al., Glycan microarray technologies: tools to survey host specificity of influenza viruses, Nature Reviews Microbiology, 4:857-864 (2006).
Swiss-Prot_Q0A2X3, Hemagglutinin precursor, Nov. 21, 2006 [online]. Retrieved on Dec. 21, 2011. Retrieved from the internet: <URL: http://www.ncbi.nlm.nih.gov/protein/Q0A2X3> LOCUS, source, and ORIGIN.
Treanor, J.J., et al., Safety and Immunogenicity of an Inactivated Subvirion Influenza A (H5N1) Vaccine, N. Eng J. Med., 354(13):1343-1351 (2006).
Tuerk, C., et al., Systematic Evolution of Ligands by Exponential Enrichment: RNA Ligands to Bacteriophage T4 DNA Polymerase, Science, 249:505-510 (1990).
Tumpey et al., Characterization of the Reconstructed 1918 Spanish Influenza Pandemic Virus, Science, 310:77-80 (2005).
Tumpey, T.M., et al., A Two-Amino Acid Change in the Hemagglutinin of the 1918 Influenza Virus Abolishes Transmission Science, 315:655-659 (2007).
Unkeless, J.C., et al., Structure and Function of Human and Murine Receptors for IgG, Ann. Rev. Immunol., 6:251-281 (1988).
Van Hoeven, N., et al., Human HA and polymerase subunit PB2 proteins confer transmission of an avian influenza virus through the air, PNAS, 106(9):3366-3371 (2009).
Van Riel, D., et al., Human and Avian Influenza Viruses Target Different Cells in the Lower Respiratory Tract of Humans and Other Mammals, The American Journal of Pathology, 171(4):1215-1223 (2007).
Verhoeyen, M., et al., Reshaping Human Antibodies: Grafting an Antilysozyme Activity, Science, 239:1534-1536 (1988).
Viswanathan et al., Determinants of Glycan Receptor Specificity of H2N2 Influenze A Virus Hemagglutinin, PLoS One, 5(10):e13768 1-9 (2010).
Wan, H., et al., Replication and Transmission of H9N2 Influenza Viruses in Ferrets: Evaluation of Pandemic Potential, PLoS One, 3(8):e2923 (13 pages) (2008).
Wang, K., et al., Expression and purification of an influenza hemagglutinin—one step closer to a recombinant protein-based influenza vaccine, Vaccine, 24:2176-2185 (2006).
Wei, C.J., et al., Cross-Neutralization of 1918 and 2009 Influenza Viruses: Role of Glycans in Viral Evolution and Vaccine Design, Science Translation Medicine, 2(24):24ra21 (8 pages) (2010).
Weiss, S.M., Predictive Data Mining—A Practical Guide, Morgan Kaufmann, San Francisco, CA (1998).
Written Opinion of PCT/US11/52670, 16 pages (Mar. 23, 2012).
Xu, D., et al., Distinct Glycan Topology for Avian and Human Sialopentasaccharide Receptor Analogues Upon Binding Different Hemagglutinins: A Molecular Dynamics Perspective, J. Mol. Biol., 387:465-491 (2009).
Xu, R., et al., Structure, Receptor Binding and Antigenicity of Influenza Virus Hemagglutinins from the 1957 H2N2 Pandemic, J. Virol., 84(4):1715-1721 (2010).
Yamada, S., et al., Haemagglutinin mutations responsible for the binding of H5N1 influenza A viruses to human-type receptors, Nature, 444:378-382 (2006).
Yang, Z.Y., et al., Immunization by Avian H5 Influenza Hemagglutinin Mutants with Altered Receptor Binding Specificity, Science, 317:825-828 (2007).
Yen, H.L., et al., Pandemic Influenza as a Current Threat, Curr. Top. Microb. Immunol., 333:3-24 (2009).
Extended European Search Report for EP 11827500.7, 8 pages (Mar. 13, 2015).
GenBank Accession No. AF270723.1, GI:8927529, 1 page, first referenced Jul. 6, 2000, last accessed Aug. 14, 2000.
Viswanathan, K. et al., Glycans as receptors for influenza pathogenesis, Glycoconjugate Journal, 27(6): 561-570 (2010).
Embl-Ebi: Alignment Seq ID No. 1 HA A/Albany/1/1958 (H2N2) Retrieved from the Internet: URL: http://www.ebi.ac.uk/Tools/services/web/tool1120161214-165058-0396-17685060-pg.
Embl-Ebi: Alignment Seq ID No. 1/ADG59715.1 (HA A/EI Salvador/2-Q226 Retrieved from the Internet:URL:http://www.ebi.ac.uk/Tools/services/web/tool1120161214-161135-0802-19761733-oy.
Hemagglutinin [Influenza A virus (A/Albany/1/1958(H2N2))]-Protein-NCBI.
Hemagglutinin [Influenza A virus (A/EI Salvador/2-Q226U1957(H2N2))]-Prat.

* cited by examiner

```
POSITIONS FROM 1 TILL 60
          CONSENSUS SEQUENCE          MAIIYLILLFTAVRGDQICIGYHANNSTEKVDTILERNVTVTHAKDILEKTHNGKLCKLN
BAA02771 A/Adachi/2/57(H2N2)          ------------------------------------------------------------
ABP49470 A/Albany/1/1958 (H2N2)       ............................................................
ABO44090 A/Albany/1/1959 (H2N2)       ............................................................
ABQ01355 A/Albany/1/1960 (H2N2)       ............................................................
ABO52247 A/Albany/1/1968 (H2N2)       ............................................................
ACV49600 A/Japan/305/1957 (H2N2)      ............................................................
BAC43764 A/Kayano/57 (H2N2)           .............................................N..............
ACD88670 A/chicken/PA/298101-4/2004   .......................S....................Q...............
         (H2N2)
ACJ69319 A/chicken/Pennsylvania/Sg-   .......................S....................Q...............
         00426/2004 (H2N2)
ACJ69324 A/chicken/Pennsylvania/Sg-   .......................S....................Q...............
         00427/2004 (H2N2)
POSITIONS FROM 61 TILL 120
          CONSENSUS SEQUENCE          GIPPLELGDCSIAGWLLGNPECDRLLRVPEWSYIMEKENPRDGLCYPGSFNDYEELKHLL
BAA02771 A/Adachi/2/57(H2N2)          ------------------------------------------------------------
ABP49470 A/Albany/1/1958 (H2N2)       ..........................S.................................
ABO44090 A/Albany/1/1959 (H2N2)       ............................................................
ABQ01355 A/Albany/1/1960 (H2N2)       ............................................................
ABO52247 A/Albany/1/1968 (H2N2)       .........................................YS.................
ACV49600 A/Japan/305/1957 (H2N2)      ..........................S.................................
BAC43764 A/Kayano/57 (H2N2)           ..........................I.................................
ACD88670 A/chicken/PA/298101-4/2004   ..........................T.......I......N.........N........
         (H2N2)
ACJ69319 A/chicken/Pennsylvania/Sg-   ..........................T.......I......N.........N........
         00426/2004 (H2N2)
ACJ69324 A/chicken/Pennsylvania/Sg-   ..........................T.......I......N.........N........
         00427/2004 (H2N2)
```

FIG. 1A

```
POSITIONS FROM 121 TILL 180
         CONSENSUS SEQUENCE          SSVKHFEKVKILPKDRWTQHTTTGGSRACAVSGNPSFFRNMVWLTKKGSNYPVAKGSYNN
BAA02771 A/Adachi/2/57(H2N2)         ------------------------------------------------------------
ABP49470 A/Albany/1/1958 (H2N2)      ............................................................
ABO44090 A/Albany/1/1959 (H2N2)      .........................................I..................
ABQ01355 A/Albany/1/1960 (H2N2)      .........R...............................I..................
ABO52247 A/Albany/1/1968 (H2N2)      ...............G....K.D...K......K..............P......R....
ACV49600 A/Japan/305/1957 (H2N2)     .............................................E..............
BAC43764 A/Kayano/57 (H2N2)          ............................................................
ACD88670 A/chicken/PA/298101-4/2004  ...R........ARN...........Q...IY.G....................R.....
         (H2N2)
ACJ69319 A/chicken/Pennsylvania/Sg-  ...R........ARN...........Q...IY.G....................R.....
         00426/2004 (H2N2)
ACJ69324 A/chicken/Pennsylvania/Sg-  ...R........ARN...........Q...IY.G....................R.....
         00427/2004 (H2N2)
POSITIONS FROM 181 TILL 240
         CONSENSUS SEQUENCE          TSGEQMLIIWGVHHPNDETEQRTLYQNVGTYVSVGTSTLNKRSTPEIATRPKVNGLGGRM
BAA02771 A/Adachi/2/57(H2N2)         ------------------------------------------------------------
ABP49470 A/Albany/1/1958 (H2N2)      ..................................S..........D..............
ABO44090 A/Albany/1/1959 (H2N2)      ..................................V..........K..............
ABQ01355 A/Albany/1/1960 (H2N2)      ...............I............E.....V..........K..............
ABO52247 A/Albany/1/1968 (H2N2)      ..................A...A...K......AS.............A..E.S...S..
ACV49600 A/Japan/305/1957 (H2N2)     .......................................................Q....
BAC43764 A/Kayano/57 (H2N2)          ...............I.....I...................................S..
ACD88670 A/chicken/PA/298101-4/2004  ...........I......N...A..............K.....V...........Q....
         (H2N2)
ACJ69319 A/chicken/Pennsylvania/Sg-  ...........I..........A..............K.....V...........Q....
         00426/2004 (H2N2)
ACJ69324 A/chicken/Pennsylvania/Sg-  ...........I..........A..............K.....V...........Q....
         00427/2004 (H2N2)
```

FIG. 1B

```
POSITIONS FROM 241 TILL 300
         CONSENSUS SEQUENCE          EFSWTLLDMWDTINFESTGNLIAPEYGFKISKRGSSGIMKTEGTLENCETKCQTPLGAIN
BAA02771 A/Adachi/2/57(H2N2)         ------------------------------------------------------------
ABP49470 A/Albany/1/1958 (H2N2)      .........................................G..................
ABO44090 A/Albany/1/1959 (H2N2)      ............................................................
ABQ01355 A/Albany/1/1960 (H2N2)      ............................................................
ABO52247 A/Albany/1/1968 (H2N2)      ........V....S.......V......................G...............
ACV49600 A/Japan/305/1957 (H2N2)     ............................................................
BAC43764 A/Kayano/57 (H2N2)          ............................................................
ACD88670 A/chicken/PA/298101-4/2004  .....I...L..............................G...................
         (H2N2)
ACJ69319 A/chicken/Pennsylvania/Sg-  .....I...L..............................G...................
         00426/2004 (H2N2)
ACJ69324 A/chicken/Pennsylvania/Sg-  .....I...L..............................G...................
         00427/2004 (H2N2)
POSITIONS FROM 301 TILL 360
         CONSENSUS SEQUENCE          TTLPFHNVHPLTIGECPKYVKSEKLVLATGLRNVPQIESRGLFGAIAGFIEGGWQGMVDG
BAA02771 A/Adachi/2/57(H2N2)         ............................................................
ABP49470 A/Albany/1/1958 (H2N2)      ............................................................
ABO44090 A/Albany/1/1959 (H2N2)      ............................................................
ABQ01355 A/Albany/1/1960 (H2N2)      ............................................................
ABO52247 A/Albany/1/1968 (H2N2)      ..............................P.............................
ACV49600 A/Japan/305/1957 (H2N2)     ............................................................
BAC43764 A/Kayano/57 (H2N2)          ............................................................
ACD88670 A/chicken/PA/298101-4/2004  .......I...............R....................................
         (H2N2)
ACJ69319 A/chicken/Pennsylvania/Sg-  .......I..............KR....................................
         00426/2004 (H2N2)
ACJ69324 A/chicken/Pennsylvania/Sg-  .......I...............R....................................
         00427/2004 (H2N2)
```

FIG. 1C

```
POSITIONS FROM 361 TILL 420
         CONSENSUS SEQUENCE            WYGYHHSNDQGSGYAADKESTQKAFDGITNKVNSVIEKMNTQFEAVGKEFSNLERRLENL
BAA02771 A/Adachi/2/57(H2N2)           ..................................................G.........
ABP49470 A/Albany/1/1958 (H2N2)        ............................................................
ABO44090 A/Albany/1/1959 (H2N2)        ......................R.....................................
ABQ01355 A/Albany/1/1960 (H2N2)        ......................R.....................................
ABO52247 A/Albany/1/1968 (H2N2)        ..........................R...........................K.....
ACV49600 A/Japan/305/1957 (H2N2)       ............................................................
BAC43764 A/Kayano/57 (H2N2)            ............................................................
ACD88670 A/chicken/PA/298101-4/2004    ........................I.........I.......S.......N...K.....
         (H2N2)
ACJ69319 A/chicken/Pennsylvania/Sg-    ........................I...I.....I...............N...K.....
         00426/2004 (H2N2)
ACJ69324 A/chicken/Pennsylvania/Sg-    ..................K.....I.........I........G......N...K.....
         00427/2004 (H2N2)
POSITIONS FROM 421 TILL 480
         CONSENSUS SEQUENCE            NKKMEDGFLDVWTYNAELLVLMENERTLDFHDSNVKNLYDKVRMQLRDNVKELGNGCFEF
BAA02771 A/Adachi/2/57(H2N2)           ..........--------------------------------------------------
ABP49470 A/Albany/1/1958 (H2N2)        ............................................................
ABO44090 A/Albany/1/1959 (H2N2)        .......L..................I.................................
ABQ01355 A/Albany/1/1960 (H2N2)        ............................................................
ABO52247 A/Albany/1/1968 (H2N2)        ............................................................
ACV49600 A/Japan/305/1957 (H2N2)       ............................................................
BAC43764 A/Kayano/57 (H2N2)            ............................................................
ACD88670 A/chicken/PA/298101-4/2004    .................................................A..........
         (H2N2)
ACJ69319 A/chicken/Pennsylvania/Sg-    .................................................A..........
         00426/2004 (H2N2)
ACJ69324 A/chicken/Pennsylvania/Sg-    .........................M.......................A..........
         00427/2004 (H2N2)
```

FIG. 1D

```
POSITIONS FROM 481 TILL 540
        CONSENSUS SEQUENCE          YHKCDDECMNSVKNGTYDYPKYEEESKLNRNEIKGVKLSSMGVYQILAIYATVAGSLSLA
BAA02771 A/Adachi/2/57(H2N2)        ------------------------------------------------------------
ABP49470 A/Albany/1/1958 (H2N2)     ............................................................
ABO44090 A/Albany/1/1959 (H2N2)     ............................................................
ABQ01355 A/Albany/1/1960 (H2N2)     ............................................................
ABO52247 A/Albany/1/1968 (H2N2)     ............................K...............................
ACV49600 A/Japan/305/1957 (H2N2)    ............................................................
BAC43764 A/Kayano/57 (H2N2)         ............................................................
ACD88670 A/chicken/PA/298101-4/2004 .......................................N....................
         (H2N2)
ACJ69319 A/chicken/Pennsylvania/Sg- .......................................N....................
         00426/2004 (H2N2)
ACJ69324 A/chicken/Pennsylvania/Sg- .......................................N....................
         00427/2004 (H2N2)

POSITIONS FROM 541 TILL 562
        CONSENSUS SEQUENCE                                  IMMAGISFWMCSNGSLQCRICI
BAA02771 A/Adachi/2/57(H2N2)                                ----------------------
ABP49470 A/Albany/1/1958 (H2N2)                             ......................
ABO44090 A/Albany/1/1959 (H2N2)                             ......................
ABQ01355 A/Albany/1/1960 (H2N2)                             ......................
ABO52247 A/Albany/1/1968 (H2N2)                             ..I...................
ACV49600 A/Japan/305/1957 (H2N2)                            ......................
BAC43764 A/Kayano/57 (H2N2)                                 .................F....
ACD88670 A/chicken/PA/298101-4/2004 (H2N2)                  ..I...FL..............
ACJ69319 A/chicken/Pennsylvania/Sg-00426/2004 (H2N2)        ..I...FL..............
ACJ69324 A/chicken/Pennsylvania/Sg-00427/2004 (H2N2)        ..I...FL..............
```

FIG. 1E

```
POSITIONS FROM 1 TILL 60
          CONSENSUS SEQUENCE                  MKTIIALSYIFCLALGQDLPGNDNSTATLCLGHHAVPNGTLVKTITNDQIEVTNATELVQ
AAB69805 A/ALASKA/84(H3N2)                    -----------------K..........................................
ABP49514 A/ALBANY/10/1968 (H3N2)              ...........Y................................................
ABQ58928 A/BANGKOK/2/1979 (H3N2)              ----------------.N..........................................
ACF41735 A/HONG KONG/1-1-MA- 12/1968(H3N2)    ..............................................D.............
ABB54514 A/MEMPHIS/1/1968 (H3N2)              ..............................................D.............
AAT64722 A/NETHERLANDS/209/80 (H3N2)          .............VFA.N..........................................
AAL60153 A/OREGON/4/80 (H3N2)                 ----------------.N................T.........................
ACH95743 A/TAIWAN/VGHYM0109-12/1984 (H3N2)    ------------------------------------------------------------

POSITIONS FROM 61 TILL 120
          CONSENSUS SEQUENCE                  SSSTGRICDSPHRILDGKNCTLIDALLGDPHCDGFQNEKWDLFVERSKAFSNCYPYDVPD
AAB69805 A/ALASKA/84(H3N2)                    ............................................................
ABP49514 A/ALBANY/10/1968 (H3N2)              ....K..NN........ID..............V....T.....................
ABQ58928 A/BANGKOK/2/1979 (H3N2)              ............................................................
ACF41735 A/HONG KONG/1-1-MA- 12/1968(H3N2)    ....K..NN........ID..............V....T.....................
ABB54514 A/MEMPHIS/1/1968 (H3N2)              ....K..NN........I...............V..D.T.....................
AAT64722 A/NETHERLANDS/209/80 (H3N2)          ......................V.....................................
AAL60153 A/OREGON/4/80 (H3N2)                 ......................V.....................................
ACH95743 A/TAIWAN/VGHYM0109-12/1984 (H3N2)    ----------------------------------------------------------..
```

FIG. 2A

```
POSITIONS FROM 121 TILL 180
        CONSENSUS SEQUENCE                        YASLRSLVASSGTLEFINEGFNWTGVTQSGGSYACKRGSDNSFFSRLNWLYESESKYPVL
AAB69805 A/ALASKA/84(H3N2)                        .......................................V..................A.
ABP49514 A/ALBANY/10/1968 (H3N2)                  .................T...T......N...N.....PGSG........TK.G.T....
ABQ58928 A/BANGKOK/2/1979 (H3N2)                  ............................................................
ACF41735 A/HONG KONG/1-1-MA- 12/1968(H3N2)        .................T...T......N...N.....PGSG........TK.G.T....
ABB54514 A/MEMPHIS/1/1968 (H3N2)                  .................T...T......N...N.....PGSG........TK.G.T....
AAT64722 A/NETHERLANDS/209/80 (H3N2)              ...................S........................................
AAL60153 A/OREGON/4/80 (H3N2)                     ...................S............S...........................
ACH95743 A/TAIWAN/VGHYM0109-12/1984 (H3N2)        ................T......................V....................

POSITIONS FROM 181 TILL 240
        CONSENSUS SEQUENCE                        NVTMPNNGNFDKLYIWGVHHPSTDKEQTNLYVRASGRVTVSTKRSQQTIIPNIGSRPWVR
AAB69805 A/ALASKA/84(H3N2)                        ........K............I..........................V.....P.....
ABP49514 A/ALBANY/10/1968 (H3N2)                  .......D...............NQ...S...Q.........R.................
ABQ58928 A/BANGKOK/2/1979 (H3N2)                  .......................Y....K...............................
ACF41735 A/HONG KONG/1-1-MA- 12/1968(H3N2)        .......D...............NQ...S...Q.........R..........W......
ABB54514 A/MEMPHIS/1/1968 (H3N2)                  .......D...............NQ...S...Q.........R.................
AAT64722 A/NETHERLANDS/209/80 (H3N2)              ............................................................
AAL60153 A/OREGON/4/80 (H3N2)                     ............................................................
ACH95743 A/TAIWAN/VGHYM0109-12/1984 (H3N2)        ........K.......................................V...........
```

FIG. 2B

```
POSITIONS FROM 241 TILL 300
      CONSENSUS SEQUENCE                        GLSSRISIYWTIVKPGDILLINSNGNLIAPRGYFKIRTGKSSIMRSDAPIGTCISECITP
AAB69805 A/ALASKA/84(H3N2)                      .......................T.............................S......
ABP49514 A/ALBANY/10/1968 (H3N2)                .................V.V...............M..............D.........
ABQ58928 A/BANGKOK/2/1979 (H3N2)                ............................................................
ACF41735 A/HONG KONG/1-1-MA- 12/1968(H3N2)      .................V.V...............M..............D.........
ABB54514 A/MEMPHIS/1/1968 (H3N2)                .................V.V...............M..............D.........
AAT64722 A/NETHERLANDS/209/80 (H3N2)            .....................................................S......
AAL60153 A/OREGON/4/80 (H3N2)                   .....................................................S......
ACH95743 A/TAIWAN/VGHYM0109-12/1984 (H3N2)      .......................T.............................S..----

POSITIONS FROM 301 TILL 360
      CONSENSUS SEQUENCE                        NGSIPNDKPFQNVNKITYGACPKYVKQNTLKLATGMRNVPEKQTRGLFGAIAGFIENGWE
AAB69805 A/ALASKA/84(H3N2)                      ......................R......................---------------
ABP49514 A/ALBANY/10/1968 (H3N2)                ............................................................
ABQ58928 A/BANGKOK/2/1979 (H3N2)                .............................................---------------
ACF41735 A/HONG KONG/1-1-MA- 12/1968(H3N2)      ............................................................
ABB54514 A/MEMPHIS/1/1968 (H3N2)                ............................................................
AAT64722 A/NETHERLANDS/209/80 (H3N2)            ..............................................I.............
AAL60153 A/OREGON/4/80 (H3N2)                   ......................R.......................I.............
ACH95743 A/TAIWAN/VGHYM0109-12/1984 (H3N2)      ------------------------------------------------------------
```

FIG. 2C

POSITIONS FROM 361 TILL 420

| | |
|---|---|
| **CONSENSUS SEQUENCE** | **GMIDGWYGFRHQNSEGTGQAADLKSTQAAIDQINGKLNRVIEKTNEKFHQIEKEFSEVEG** |
| AAB69805 A/ALASKA/84(H3N2) | ------------------------------------------------------------ |
| ABP49514 A/ALBANY/10/1968 (H3N2) | ............................................................ |
| ABQ58928 A/BANGKOK/2/1979 (H3N2) | ------------------------------------------------------------ |
| ACF41735 A/HONG KONG/1-1-MA- 12/1968(H3N2) | ............................................................ |
| ABB54514 A/MEMPHIS/1/1968 (H3N2) | ............................................................ |
| AAT64722 A/NETHERLANDS/209/80 (H3N2) | ..V--------------------------------------------------------- |
| AAL60153 A/OREGON/4/80 (H3N2) | ..XX..------------------------------------------------------ |
| ACH95743 A/TAIWAN/VGHYM0109-12/1984 (H3N2) | ------------------------------------------------------------ |

POSITIONS FROM 421 TILL 480

| | |
|---|---|
| **CONSENSUS SEQUENCE** | **RIQDLEKYVEDTKIDLWSYNAELLVALENQHTIDLTDSEMNKLFEKTRRQLRENAEDMGN** |
| AAB69805 A/ALASKA/84(H3N2) | ------------------------------------------------------------ |
| ABP49514 A/ALBANY/10/1968 (H3N2) | ............................................................ |
| ABQ58928 A/BANGKOK/2/1979 (H3N2) | ------------------------------------------------------------ |
| ACF41735 A/HONG KONG/1-1-MA- 12/1968(H3N2) | ............................................................ |
| ABB54514 A/MEMPHIS/1/1968 (H3N2) | ............................................................ |
| AAT64722 A/NETHERLANDS/209/80 (H3N2) | ------------------------------------------------------------ |
| AAL60153 A/OREGON/4/80 (H3N2) | ------------------------------------------------------------ |
| ACH95743 A/TAIWAN/VGHYM0109-12/1984 (H3N2) | ------------------------------------------------------------ |

FIG. 2D

POSITIONS FROM 481 TILL 540

| | |
|---|---|
| CONSENSUS SEQUENCE | GCFKIYHKCDNACIESIRNGTYDHDVYRDEALNNRFQIKGVELKSGYKDWILWISFAISC |
| AAB69805 A/ALASKA/84(H3N2) | ------------------------------------------------------------ |
| ABP49514 A/ALBANY/10/1968 (H3N2) | ............................................................ |
| ABQ58928 A/BANGKOK/2/1979 (H3N2) | ------------------------------------------------------------ |
| ACF41735 A/HONG KONG/1-1-MA- 12/1968(H3N2) | ..........................N................................. |
| ABB54514 A/MEMPHIS/1/1968 (H3N2) | ............................................................ |
| AAT64722 A/NETHERLANDS/209/80 (H3N2) | ------------------------------------------------------------ |
| AAL60153 A/OREGON/4/80 (H3N2) | ------------------------------------------------------------ |
| ACH95743 A/TAIWAN/VGHYM0109-12/1984 (H3N2) | ------------------------------------------------------------ |

POSITIONS FROM 541 TILL 566

| | |
|---|---|
| CONSENSUS SEQUENCE | FLLCVVLLGFIMWACQRGNIRCNICI |
| AAB69805 A/ALASKA/84(H3N2) | -------------------------- |
| ABP49514 A/ALBANY/10/1968 (H3N2) | .......................... |
| ABQ58928 A/BANGKOK/2/1979 (H3N2) | -------------------------- |
| ACF41735 A/HONG KONG/1-1-MA-12/1968(H3N2) | .......................... |
| ABB54514 A/MEMPHIS/1/1968 (H3N2) | .......................... |
| AAT64722 A/NETHERLANDS/209/80(H3N2) | -------------------------- |
| AAL60153 A/OREGON/4/80 (H3N2) | -------------------------- |
| ACH95743 A/TAIWAN/VGHYM0109-12/1984 (H3N2) | -------------------------- |

FIG. 2E

DOTTED GRAY LINES, 4S AND 6S INDICATE POTENTIAL SITES FOR FUCOSYLATION AND SULFATION MODIFICATIONS

LONG α2-6 *UMBRELLA*-LIKE TOPOLOGY GLYCANS THAT ARE NOT DECOYS

N-LINKED GLYCANS:

*α2-6 LINKAGE ON GlcNAc OF TYPE 1/TYPE 2 EXTENSION*

LONG α2-6 *UMBRELLA*-LIKE TOPOLOGY GLYCAN DECOYS
O-LINKED GLYCANS:
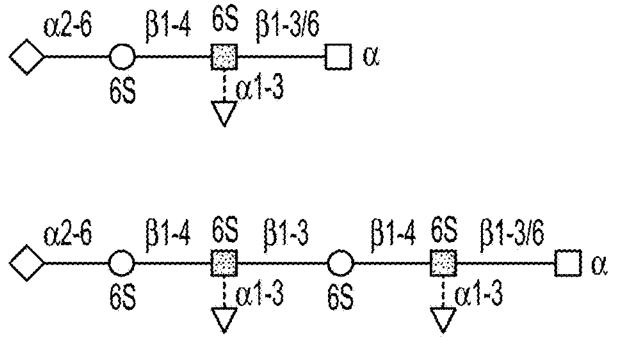
*α2-6 TYPE 2 EXTENSION BRANCH IN A CORE 2 OR 3 OR 4 TYPE STRUCTURE*
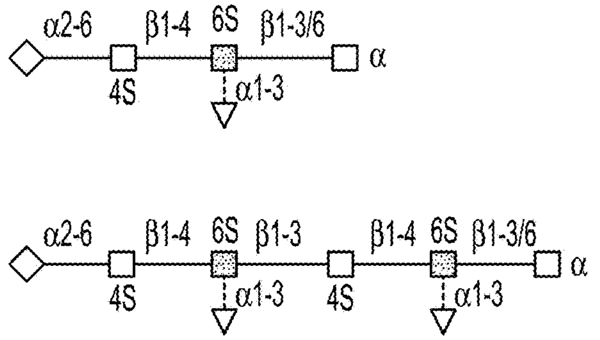
*α2-6 LacDiNAc EXTENSION BRANCH IN A CORE 2 OR 3 OR 4 TYPE STRUCTURE*
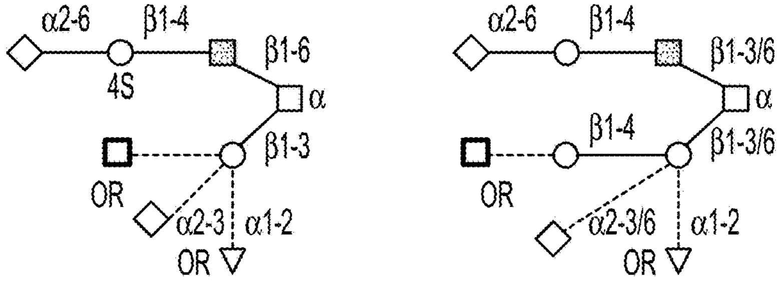
*α2-6 ATTACHED TO BRANCHED CORE 2 AND CORE 4 STRUCTURES*
FIG. 4A-4

LONG α2-6 *UMBRELLA*-LIKE TOPOLOGY GLYCAN THAT ARE NOT DECOYS

O-LINKED GLYCANS:

LONG α2-6 *UMBRELLA*-LIKE TOPOLOGY GLYCAN THAT ARE NOT DECOYS
GLYCOLIPIDS:
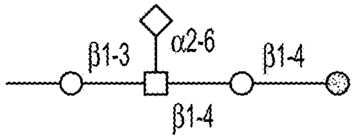
*GLUCOSYLCERAMIDE CORE GANGLIO TYPE*
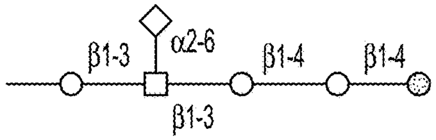
*GLUCOSYLCERAMIDE CORE GLOBO TYPE*
FIG. 4A-7

UMBRELLA-LIKE TOPOLOGY

CONE-LIKE TOPOLOGY

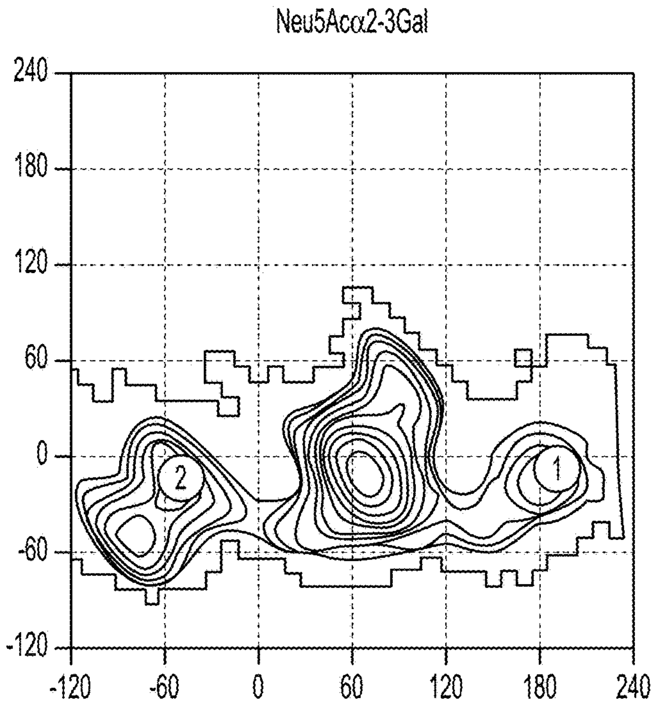
FIG. 12C-A
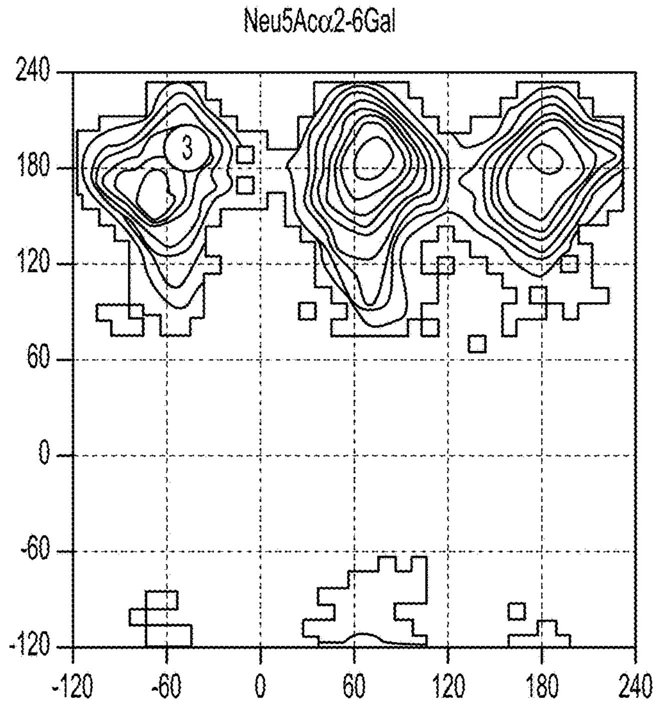
FIG. 12C-B

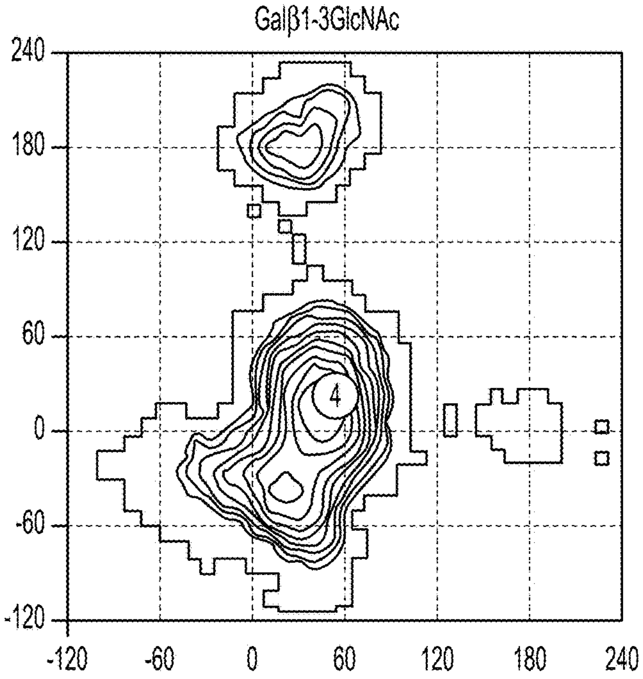
FIG. 12C-C
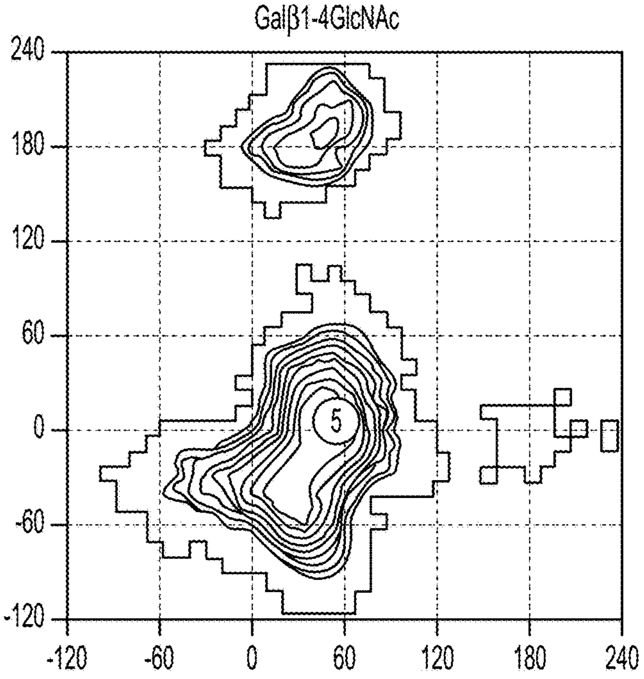
FIG. 12C-D

CONFORMATIONAL SAMPLING OF α2-3 LINKAGE

| | |
|---|---|
| *Cone-like* | 100% |
| *Umbrella-like* | 0% |

FIG. 12C-E

CONFORMATIONAL SAMPLING OF α2-6 LINKAGE

| | *Umbrella-like* (%) : *Cone-Like* (%) |
|---|---|
| $\omega = -60^\circ$ | 60 : 20 |
| $\omega = +60^\circ$ | 10 : 40 |
| $\omega = 180^\circ$ | 30 : 30 |

```
                          SEQUENCE LISTING


<160> NUMBER OF SEQ ID NOS: 28

<210> SEQ ID NO 1
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 1

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45
```

```
Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Arg Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
```

-continued

```
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 2
<211> LENGTH: 131
<212> TYPE: PRT
<213> ORGANISM: Artificial Sequence
<220> FEATURE:
<223> OTHER INFORMATION: NCBI influenza virus sequence

<400> SEQUENCE: 2

Asn Thr Thr Leu Pro Phe His Asn Val His Pro Leu Thr Ile Gly Glu
1               5                   10                  15

Cys Pro Lys Tyr Val Lys Ser Glu Lys Leu Val Leu Ala Thr Gly Leu
            20                  25                  30

Arg Asn Val Pro Gln Ile Glu Ser Arg Gly Leu Phe Gly Ala Ile Ala
        35                  40                  45

Gly Phe Ile Glu Gly Gly Trp Gln Gly Met Val Asp Gly Trp Tyr Gly
    50                  55                  60

Tyr His His Ser Asn Asp Gln Gly Ser Gly Tyr Ala Ala Asp Lys Glu
65                  70                  75                  80

Ser Thr Gln Lys Ala Phe Asp Gly Ile Thr Asn Lys Val Asn Ser Val
                85                  90                  95

Ile Glu Lys Met Asn Thr Gln Phe Glu Ala Val Gly Lys Glu Phe Gly
            100                 105                 110

Asn Leu Glu Arg Arg Leu Glu Asn Leu Asn Lys Lys Met Glu Asp Gly
        115                 120                 125

Phe Leu Asp
    130


<210> SEQ ID NO 3
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 3

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
```

-continued

```
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Ser Thr Ser Thr Leu Asn Lys Arg Ser Thr
    210                 215                 220

Pro Asp Ile Ala Thr Arg Pro Lys Val Asn Gly Leu Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Gly Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495
```

-continued

```
Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 4
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 4

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Arg Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Ile Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Val Thr Ser Thr Leu Asn Lys Arg Ser Thr
    210                 215                 220

Pro Lys Ile Ala Thr Arg Pro Lys Val Asn Gly Leu Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285
```

```
Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Arg Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Leu Leu Asp Val Trp
            420                 425                 430

Thr Tyr Asn Ala Glu Leu Leu Val Leu Met Glu Asn Glu Arg Ile Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 5
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 5

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Arg Val Pro Glu Trp Ser Tyr Ile Met Glu
```

-continued

```
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Arg Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Ile Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Glu Thr Tyr Val Ser Val Val Thr Ser Thr Leu Asn Lys Arg Ser Thr
    210                 215                 220

Pro Lys Ile Ala Thr Arg Pro Lys Val Asn Gly Leu Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Arg Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510
```

```
Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 6
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 6

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Arg Val Pro Glu Trp Ser Tyr Ile Met Glu
                85                  90                  95

Lys Glu Asn Pro Arg Tyr Ser Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Gly Trp Thr Gln His Lys Thr Asp Gly
    130                 135                 140

Gly Ser Lys Ala Cys Ala Val Ser Gly Lys Pro Ser Phe Phe Arg Asn
145                 150                 155                 160

Met Val Trp Leu Thr Lys Lys Gly Pro Asn Tyr Pro Val Ala Lys Arg
                165                 170                 175

Ser Tyr Asn Asn Thr Ser Gly Glu Gln Met Leu Ile Ile Trp Gly Val
            180                 185                 190

His His Pro Asn Asp Glu Ala Glu Gln Arg Ala Leu Tyr Gln Lys Val
        195                 200                 205

Gly Thr Tyr Val Ser Ala Ser Thr Ser Thr Leu Asn Lys Arg Ser Thr
    210                 215                 220

Pro Glu Ile Ala Ala Arg Pro Glu Val Ser Gly Leu Gly Ser Arg Met
225                 230                 235                 240

Glu Phe Ser Trp Thr Leu Leu Asp Val Trp Asp Thr Ile Ser Phe Glu
                245                 250                 255

Ser Thr Gly Asn Leu Val Ala Pro Glu Tyr Gly Phe Lys Ile Ser Lys
            260                 265                 270

Arg Gly Ser Ser Gly Ile Met Lys Thr Glu Gly Thr Leu Gly Asn Cys
        275                 280                 285

Glu Thr Lys Cys Gln Thr Pro Leu Gly Ala Ile Asn Thr Thr Leu Pro
    290                 295                 300
```

```
Phe His Asn Val His Pro Leu Thr Ile Gly Glu Cys Pro Lys Tyr Val
305                 310                 315                 320

Lys Ser Glu Lys Leu Val Leu Ala Thr Gly Pro Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Arg Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Lys Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Ile Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 7
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 7

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
```

-continued

```
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Glu Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525
```

```
Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 8
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 8

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asn Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ile Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Ile Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320
```

```
Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Phe Arg Ile
545                 550                 555                 560

Cys Ile


<210> SEQ ID NO 9
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 9

Met Ala Ile Ile Tyr Leu Ile Leu Leu Phe Thr Ala Val Arg Gly Asp
1               5                   10                  15

Gln Ile Cys Ile Gly Tyr His Ser Asn Asn Ser Thr Glu Lys Val Asp
            20                  25                  30

Thr Ile Leu Glu Arg Asn Val Thr Val Thr His Ala Gln Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Ile Glu
                85                  90                  95

Lys Glu Asn Pro Arg Asn Gly Leu Cys Tyr Pro Gly Ser Phe Asn Asn
            100                 105                 110

Tyr Glu Glu Leu Lys His Leu Leu Ser Ser Val Arg His Phe Glu Lys
```

```
        115                 120                 125

Val Lys Ile Leu Ala Arg Asn Arg Trp Thr Gln His Thr Thr Thr Gly
    130                 135                 140

Gly Ser Gln Ala Cys Ala Ile Tyr Gly Gly Pro Ser Phe Phe Arg Asn
145                 150                 155                 160

Met Val Trp Leu Thr Lys Lys Gly Ser Asn Tyr Pro Val Ala Arg Gly
                165                 170                 175

Ser Tyr Asn Asn Thr Ser Gly Glu Gln Met Leu Ile Ile Trp Gly Ile
            180                 185                 190

His His Pro Asn Asp Glu Asn Glu Gln Arg Ala Leu Tyr Gln Asn Val
        195                 200                 205

Gly Thr Tyr Val Ser Val Gly Thr Ser Lys Leu Asn Lys Arg Ser Val
    210                 215                 220

Pro Glu Ile Ala Thr Arg Pro Lys Val Asn Gly Gln Gly Gly Arg Met
225                 230                 235                 240

Glu Phe Ser Trp Thr Ile Leu Asp Met Leu Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Gly Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Ile Asp Gly Ile Thr Asn Lys Val Asn Ser Ile Ile Glu Lys Met Asn
385                 390                 395                 400

Thr Gln Ser Glu Ala Val Gly Lys Glu Phe Asn Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
    530                 535                 540
```

Gly Ile Phe Leu Trp Met Cys Ser Asn Gly Ser Leu Gln Cys Arg Ile
545 550 555 560

Cys Ile

<210> SEQ ID NO 10
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 10

Met Ala Ile Ile Tyr Leu Ile Leu Leu Phe Thr Ala Val Arg Gly Asp
1 5 10 15

Gln Ile Cys Ile Gly Tyr His Ser Asn Asn Ser Thr Glu Lys Val Asp
20 25 30

Thr Ile Leu Glu Arg Asn Val Thr Val Thr His Ala Gln Asp Ile Leu
35 40 45

Glu Lys Thr His Asn Gly Lys Leu Cys Lys Leu Asn Gly Ile Pro Pro
50 55 60

Leu Glu Leu Gly Asp Cys Ser Ile Ala Gly Trp Leu Leu Gly Asn Pro
65 70 75 80

Glu Cys Asp Arg Leu Leu Thr Val Pro Glu Trp Ser Tyr Ile Ile Glu
85 90 95

Lys Glu Asn Pro Arg Asn Gly Leu Cys Tyr Pro Gly Ser Phe Asn Asn
100 105 110

Tyr Glu Glu Leu Lys His Leu Leu Ser Ser Val Arg His Phe Glu Lys
115 120 125

Val Lys Ile Leu Ala Arg Asn Arg Trp Thr Gln His Thr Thr Thr Gly
130 135 140

Gly Ser Gln Ala Cys Ala Ile Tyr Gly Gly Pro Ser Phe Phe Arg Asn
145 150 155 160

Met Val Trp Leu Thr Lys Lys Gly Ser Asn Tyr Pro Val Ala Arg Gly
165 170 175

Ser Tyr Asn Asn Thr Ser Gly Glu Gln Met Leu Ile Ile Trp Gly Ile
180 185 190

His His Pro Asn Asp Glu Thr Glu Gln Arg Ala Leu Tyr Gln Asn Val
195 200 205

Gly Thr Tyr Val Ser Val Gly Thr Ser Lys Leu Asn Lys Arg Ser Val
210 215 220

Pro Glu Ile Ala Thr Arg Pro Lys Val Asn Gly Gln Gly Gly Arg Met
225 230 235 240

Glu Phe Ser Trp Thr Ile Leu Asp Met Leu Asp Thr Ile Asn Phe Glu
245 250 255

Ser Thr Gly Asn Leu Ile Ala Pro Glu Tyr Gly Phe Lys Ile Ser Lys
260 265 270

Arg Gly Ser Ser Gly Ile Met Lys Thr Gly Gly Thr Leu Glu Asn Cys
275 280 285

Glu Thr Lys Cys Gln Thr Pro Leu Gly Ala Ile Asn Thr Thr Leu Pro
290 295 300

Phe His Asn Ile His Pro Leu Thr Ile Gly Glu Cys Pro Lys Tyr Val
305 310 315 320

Lys Ser Lys Arg Leu Val Leu Ala Thr Gly Leu Arg Asn Val Pro Gln
325 330 335

Ile Glu Ser Arg Gly Leu Phe Gly Ala Ile Ala Gly Phe Ile Glu Gly
340 345 350

Gly Trp Gln Gly Met Val Asp Gly Trp Tyr Gly Tyr His His Ser Asn
355 360 365

Asp Gln Gly Ser Gly Tyr Ala Ala Asp Lys Glu Ser Thr Gln Lys Ala
370 375 380

Ile Asp Gly Ile Ile Asn Lys Val Asn Ser Ile Ile Glu Lys Met Asn
385 390 395 400

Thr Gln Phe Glu Ala Val Gly Lys Glu Phe Asn Asn Leu Glu Lys Arg
405 410 415

Leu Glu Asn Leu Asn Lys Lys Met Glu Asp Gly Phe Leu Asp Val Trp
420 425 430

Thr Tyr Asn Ala Glu Leu Leu Val Leu Met Glu Asn Glu Arg Thr Leu
435 440 445

Asp Phe His Asp Ser Asn Val Lys Asn Leu Tyr Asp Lys Val Arg Met
450 455 460

Gln Leu Arg Asp Asn Ala Lys Glu Leu Gly Asn Gly Cys Phe Glu Phe
465 470 475 480

Tyr His Lys Cys Asp Asp Glu Cys Met Asn Ser Val Lys Asn Gly Thr
485 490 495

Tyr Asp Tyr Pro Lys Tyr Glu Glu Glu Ser Lys Leu Asn Arg Asn Glu
500 505 510

Ile Lys Gly Val Lys Leu Ser Asn Met Gly Val Tyr Gln Ile Leu Ala
515 520 525

Ile Tyr Ala Thr Val Ala Gly Ser Leu Ser Leu Ala Ile Met Ile Ala
530 535 540

Gly Ile Phe Leu Trp Met Cys Ser Asn Gly Ser Leu Gln Cys Arg Ile
545 550 555 560

Cys Ile

<210> SEQ ID NO 11
<211> LENGTH: 562
<212> TYPE: PRT
<213> ORGANISM: Artificial Sequence
<220> FEATURE:
<223> OTHER INFORMATION: NCBI influenza virus sequence

<400> SEQUENCE: 11

Met Ala Ile Ile Tyr Leu Ile Leu Leu Phe Thr Ala Val Arg Gly Asp
1 5 10 15

Gln Ile Cys Ile Gly Tyr His Ser Asn Asn Ser Thr Glu Lys Val Asp
20 25 30

Thr Ile Leu Glu Arg Asn Val Thr Val Thr His Ala Gln Asp Ile Leu
35 40 45

Glu Lys Thr His Asn Gly Lys Leu Cys Lys Leu Asn Gly Ile Pro Pro
50 55 60

Leu Glu Leu Gly Asp Cys Ser Ile Ala Gly Trp Leu Leu Gly Asn Pro
65 70 75 80

Glu Cys Asp Arg Leu Leu Thr Val Pro Glu Trp Ser Tyr Ile Ile Glu
85 90 95

Lys Glu Asn Pro Arg Asn Gly Leu Cys Tyr Pro Gly Ser Phe Asn Asn
100 105 110

Tyr Glu Glu Leu Lys His Leu Leu Ser Ser Val Arg His Phe Glu Lys
115 120 125

Val Lys Ile Leu Ala Arg Asn Arg Trp Thr Gln His Thr Thr Thr Gly

-continued

```
    130                 135                 140

Gly Ser Gln Ala Cys Ala Ile Tyr Gly Gly Pro Ser Phe Phe Arg Asn
145                 150                 155                 160

Met Val Trp Leu Thr Lys Lys Gly Ser Asn Tyr Pro Val Ala Arg Gly
                165                 170                 175

Ser Tyr Asn Asn Thr Ser Gly Glu Gln Met Leu Ile Ile Trp Gly Ile
            180                 185                 190

His His Pro Asn Asp Glu Thr Glu Gln Arg Ala Leu Tyr Gln Asn Val
        195                 200                 205

Gly Thr Tyr Val Ser Val Gly Thr Ser Lys Leu Asn Lys Arg Ser Val
    210                 215                 220

Pro Glu Ile Ala Thr Arg Pro Lys Val Asn Gly Gln Gly Gly Arg Met
225                 230                 235                 240

Glu Phe Ser Trp Thr Ile Leu Asp Met Leu Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Gly Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Lys Ser Thr Gln Lys Ala
    370                 375                 380

Ile Asp Gly Ile Thr Asn Lys Val Asn Ser Ile Ile Glu Lys Met Asn
385                 390                 395                 400

Thr Gln Phe Gly Ala Val Gly Lys Glu Phe Asn Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Met Thr Leu
        435                 440                 445

Asp Phe His Asp Ser Asn Val Lys Asn Leu Tyr Asp Lys Val Arg Met
    450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
    530                 535                 540

Gly Ile Phe Leu Trp Met Cys Ser Asn Gly Ser Leu Gln Cys Arg Ile
545                 550                 555                 560
```

Cys Ile

<210> SEQ ID NO 12
<211> LENGTH: 566
<212> TYPE: PRT
<213> ORGANISM: Artificial Sequence
<220> FEATURE:
<223> OTHER INFORMATION: NCBI influenza virus sequence

<400> SEQUENCE: 12

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
    130                 135                 140

Gly Val Thr Gln Ser Gly Gly Ser Tyr Ala Cys Lys Arg Gly Ser Asp
145                 150                 155                 160

Asn Ser Phe Phe Ser Arg Leu Asn Trp Leu Tyr Glu Ser Glu Ser Lys
                165                 170                 175

Tyr Pro Val Leu Asn Val Thr Met Pro Asn Asn Gly Asn Phe Asp Lys
            180                 185                 190

Leu Tyr Ile Trp Gly Val His His Pro Ser Thr Asp Lys Glu Gln Thr
        195                 200                 205

Asn Leu Tyr Val Arg Ala Ser Gly Arg Val Thr Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Asn Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350
```

```
Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 13
<211> LENGTH: 328
<212> TYPE: PRT
<213> ORGANISM: Artificial Sequence
<220> FEATURE:
<223> OTHER INFORMATION: NCBI influenza virus sequence

<400> SEQUENCE: 13

Lys Leu Pro Gly Asn Asp Asn Ser Thr Ala Thr Leu Cys Leu Gly His
1               5                   10                  15

His Ala Val Pro Asn Gly Thr Leu Val Lys Thr Ile Thr Asn Asp Gln
            20                  25                  30

Ile Glu Val Thr Asn Ala Thr Glu Leu Val Gln Ser Ser Ser Thr Gly
        35                  40                  45

Arg Ile Cys Asp Ser Pro His Arg Ile Leu Asp Gly Lys Asn Cys Thr
    50                  55                  60

Leu Ile Asp Ala Leu Leu Gly Asp Pro His Cys Asp Gly Phe Gln Asn
65                  70                  75                  80

Glu Lys Trp Asp Leu Phe Val Glu Arg Ser Lys Ala Phe Ser Asn Cys
                85                  90                  95

Tyr Pro Tyr Asp Val Pro Asp Tyr Ala Ser Leu Arg Ser Leu Val Ala
            100                 105                 110

Ser Ser Gly Thr Leu Glu Phe Ile Asn Glu Gly Phe Asn Trp Thr Gly
        115                 120                 125

Val Thr Gln Ser Gly Gly Ser Tyr Ala Cys Lys Arg Gly Ser Val Asn
    130                 135                 140
```

-continued

Ser Phe Phe Ser Arg Leu Asn Trp Leu Tyr Glu Ser Glu Ser Lys Tyr
145 150 155 160

Pro Ala Leu Asn Val Thr Met Pro Asn Asn Gly Lys Phe Asp Lys Leu
165 170 175

Tyr Ile Trp Gly Val His His Pro Ile Thr Asp Lys Glu Gln Thr Asn
180 185 190

Leu Tyr Val Arg Ala Ser Gly Arg Val Thr Val Ser Thr Lys Arg Ser
195 200 205

Gln Gln Thr Val Ile Pro Asn Ile Gly Pro Arg Pro Trp Val Arg Gly
210 215 220

Leu Ser Ser Arg Ile Ser Ile Tyr Trp Thr Ile Val Lys Pro Gly Asp
225 230 235 240

Ile Leu Leu Ile Asn Ser Thr Gly Asn Leu Ile Ala Pro Arg Gly Tyr
245 250 255

Phe Lys Ile Arg Thr Gly Lys Ser Ser Ile Met Arg Ser Asp Ala Pro
260 265 270

Ile Gly Thr Cys Ser Ser Glu Cys Ile Thr Pro Asn Gly Ser Ile Pro
275 280 285

Asn Asp Lys Pro Phe Gln Asn Val Asn Lys Ile Thr Tyr Gly Ala Cys
290 295 300

Pro Arg Tyr Val Lys Gln Asn Thr Leu Lys Leu Ala Thr Gly Met Arg
305 310 315 320

Asn Val Pro Glu Lys Gln Thr Arg
325

<210> SEQ ID NO 14
<211> LENGTH: 566
<212> TYPE: PRT
<213> ORGANISM: Artificial Sequence
<220> FEATURE:
<223> OTHER INFORMATION: NCBI influenza virus sequence

<400> SEQUENCE: 14

Met Lys Thr Ile Ile Ala Leu Ser Tyr Ile Phe Tyr Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asn Asp
35 40 45

Gln Ile Glu Val Thr Asn Ala Thr Glu Leu Val Gln Ser Ser Ser Thr
50 55 60

Gly Lys Ile Cys Asn Asn Pro His Arg Ile Leu Asp Gly Ile Asp Cys
65 70 75 80

Thr Leu Ile Asp Ala Leu Leu Gly Asp Pro His Cys Asp Val Phe Gln
85 90 95

Asn Glu Thr Trp Asp Leu Phe Val Glu Arg Ser Lys Ala Phe Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Ile Thr Glu Gly Phe Thr Trp Thr
130 135 140

Gly Val Thr Gln Asn Gly Gly Ser Asn Ala Cys Lys Arg Gly Pro Gly
145 150 155 160

Ser Gly Phe Phe Ser Arg Leu Asn Trp Leu Thr Lys Ser Gly Ser Thr
165 170 175

```
Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565
```

<210> SEQ ID NO 15
<211> LENGTH: 329
<212> TYPE: PRT

<213> ORGANISM: Artificial Sequence
<220> FEATURE:
<223> OTHER INFORMATION: NCBI influenza virus sequence

<400> SEQUENCE: 15

```
Gln Asn Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Arg Ile Cys Asp Ser Pro His Arg Ile Leu Asp Gly Lys Asn Cys
    50                  55                  60

Thr Leu Ile Asp Ala Leu Leu Gly Asp Pro His Cys Asp Gly Phe Gln
65                  70                  75                  80

Asn Glu Lys Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Asn Glu Gly Phe Asn Trp Thr
        115                 120                 125

Gly Val Thr Gln Ser Gly Gly Ser Tyr Ala Cys Lys Arg Gly Ser Asp
    130                 135                 140

Asn Ser Phe Phe Ser Arg Leu Asn Trp Leu Tyr Glu Ser Glu Ser Lys
145                 150                 155                 160

Tyr Pro Val Leu Asn Val Thr Met Pro Asn Asn Gly Asn Phe Asp Lys
                165                 170                 175

Leu Tyr Ile Trp Gly Val His His Pro Ser Thr Tyr Lys Glu Gln Thr
            180                 185                 190

Lys Leu Tyr Val Arg Ala Ser Gly Arg Val Thr Val Ser Thr Lys Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Asn Gly Asn Leu Ile Ala Pro Arg Gly
                245                 250                 255

Tyr Phe Lys Ile Arg Thr Gly Lys Ser Ser Ile Met Arg Ser Asp Ala
            260                 265                 270

Pro Ile Gly Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325
```

<210> SEQ ID NO 16
<211> LENGTH: 566
<212> TYPE: PRT
<213> ORGANISM: Artificial Sequence
<220> FEATURE:
<223> OTHER INFORMATION: NCBI influenza virus sequence

<400> SEQUENCE: 16

-continued

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Trp Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
```

-continued

```
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Asn Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 17
<211> LENGTH: 566
<212> TYPE: PRT
<213> ORGANISM: Artificial Sequence
<220> FEATURE:
<223> OTHER INFORMATION: NCBI influenza virus sequence

<400> SEQUENCE: 17

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asn Cys
65                  70                  75                  80

Thr Leu Ile Asp Ala Leu Leu Gly Asp Pro His Cys Asp Val Phe Gln
                85                  90                  95

Asp Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
```

```
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 18
<211> LENGTH: 363
<212> TYPE: PRT
<213> ORGANISM: Artificial Sequence
<220> FEATURE:
<223> OTHER INFORMATION: NCBI influenza virus sequence

<400> SEQUENCE: 18

Met Lys Thr Ile Ile Ala Leu Ser Tyr Ile Phe Cys Leu Val Phe Ala
```

-continued

```
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Val Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Ser Phe Asn Trp Thr
    130                 135                 140

Gly Val Thr Gln Ser Gly Gly Ser Tyr Ala Cys Lys Arg Gly Ser Asp
145                 150                 155                 160

Asn Ser Phe Phe Ser Arg Leu Asn Trp Leu Tyr Glu Ser Glu Ser Lys
                165                 170                 175

Tyr Pro Val Leu Asn Val Thr Met Pro Asn Asn Gly Asn Phe Asp Lys
            180                 185                 190

Leu Tyr Ile Trp Gly Val His His Pro Ser Thr Asp Lys Glu Gln Thr
        195                 200                 205

Asn Leu Tyr Val Arg Ala Ser Gly Arg Val Thr Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Asn Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val
        355                 360
```

<210> SEQ ID NO 19
<211> LENGTH: 350
<212> TYPE: PRT
<213> ORGANISM: Artificial Sequence
<220> FEATURE:
<223> OTHER INFORMATION: NCBI influenza virus sequence
<220> FEATURE:
<221> NAME/KEY: misc_feature
<222> LOCATION: (347)..(348)
<223> OTHER INFORMATION: Xaa can be any naturally occurring amino acid

<400> SEQUENCE: 19

```
Gln Asn Leu Pro Gly Asn Asp Asn Ser Thr Ala Thr Leu Cys Leu Gly
1               5                   10                  15

His His Thr Val Pro Asn Gly Thr Leu Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Arg Ile Cys Asp Ser Pro His Arg Ile Leu Asp Gly Lys Asn Cys
    50                  55                  60

Thr Leu Val Asp Ala Leu Leu Gly Asp Pro His Cys Asp Gly Phe Gln
65                  70                  75                  80

Asn Glu Lys Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Asn Glu Ser Phe Asn Trp Thr
        115                 120                 125

Gly Val Thr Gln Ser Gly Gly Ser Ser Ala Cys Lys Arg Gly Ser Asp
    130                 135                 140

Asn Ser Phe Phe Ser Arg Leu Asn Trp Leu Tyr Glu Ser Glu Ser Lys
145                 150                 155                 160

Tyr Pro Val Leu Asn Val Thr Met Pro Asn Asn Gly Asn Phe Asp Lys
                165                 170                 175

Leu Tyr Ile Trp Gly Val His His Pro Ser Thr Asp Lys Glu Gln Thr
            180                 185                 190

Asn Leu Tyr Val Arg Ala Ser Gly Arg Val Thr Val Ser Thr Lys Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Asn Gly Asn Leu Ile Ala Pro Arg Gly
                245                 250                 255

Tyr Phe Lys Ile Arg Thr Gly Lys Ser Ser Ile Met Arg Ser Asp Ala
            260                 265                 270

Pro Ile Gly Thr Cys Ser Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Xaa Xaa Gly Trp
            340                 345                 350
```

<210> SEQ ID NO 20
<211> LENGTH: 178
<212> TYPE: PRT
<213> ORGANISM: Artificial Sequence
<220> FEATURE:
<223> OTHER INFORMATION: NCBI influenza virus sequence

<400> SEQUENCE: 20

```
Pro Asp Tyr Ala Ser Leu Arg Ser Leu Val Ala Ser Ser Gly Thr Leu
1               5                   10                  15

Glu Phe Thr Asn Glu Gly Phe Asn Trp Thr Gly Val Thr Gln Ser Gly
            20                  25                  30

Gly Ser Tyr Ala Cys Lys Arg Gly Ser Val Asn Ser Phe Phe Ser Arg
        35                  40                  45

Leu Asn Trp Leu Tyr Glu Ser Glu Ser Lys Tyr Pro Val Leu Asn Val
    50                  55                  60

Thr Met Pro Asn Asn Gly Lys Phe Asp Lys Leu Tyr Ile Trp Gly Val
65                  70                  75                  80

His His Pro Ser Thr Asp Lys Glu Gln Thr Asn Leu Tyr Val Arg Ala
                85                  90                  95

Ser Gly Arg Val Thr Val Ser Thr Lys Arg Ser Gln Gln Thr Val Ile
            100                 105                 110

Pro Asn Ile Gly Ser Arg Pro Trp Val Arg Gly Leu Ser Ser Arg Ile
        115                 120                 125

Ser Ile Tyr Trp Thr Ile Val Lys Pro Gly Asp Ile Leu Leu Ile Asn
    130                 135                 140

Ser Thr Gly Asn Leu Ile Ala Pro Arg Gly Tyr Phe Lys Ile Arg Thr
145                 150                 155                 160

Gly Lys Ser Ser Ile Met Arg Ser Asp Ala Pro Ile Gly Thr Cys Ser
                165                 170                 175

Ser Glu


<210> SEQ ID NO 21
<211> LENGTH: 106
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (2)..(2)
<223> OTHER INFORMATION: X= Tyr or Phe
<220> FEATURE:
<221> NAME/KEY: MISC_FEATURE
<222> LOCATION: (4)..(33)
<223> OTHER INFORMATION: X= any amino acid
<220> FEATURE:
<221> NAME/KEY: MISC_FEATURE
<222> LOCATION: (34)..(34)
<223> OTHER INFORMATION: X is absent or any amino acid
<220> FEATURE:
<221> NAME/KEY: MISC_FEATURE
<222> LOCATION: (35)..(35)
<223> OTHER INFORMATION: X is absent or any amino acid
<220> FEATURE:
<221> NAME/KEY: MISC_FEATURE
<222> LOCATION: (36)..(36)
<223> OTHER INFORMATION: X is absent or any amino acid
<220> FEATURE:
<221> NAME/KEY: MISC_FEATURE
<222> LOCATION: (37)..(37)
<223> OTHER INFORMATION: X is absent or any amino acid
<220> FEATURE:
<221> NAME/KEY: MISC_FEATURE
<222> LOCATION: (38)..(38)
<223> OTHER INFORMATION: X is absent or any amino acid
<220> FEATURE:
<221> NAME/KEY: MISC_FEATURE
<222> LOCATION: (39)..(39)
<223> OTHER INFORMATION: X is absent or any amino acid
<220> FEATURE:
<221> NAME/KEY: MISC_FEATURE
<222> LOCATION: (40)..(40)
<223> OTHER INFORMATION: X is absent or any amino acid
<220> FEATURE:
```

<221> NAME/KEY: MISC_FEATURE
<222> LOCATION: (41)..(41)
<223> OTHER INFORMATION: X is absent or any amino acid
<220> FEATURE:
<221> NAME/KEY: MISC_FEATURE
<222> LOCATION: (42)..(42)
<223> OTHER INFORMATION: X is absent or any amino acid
<220> FEATURE:
<221> NAME/KEY: MISC_FEATURE
<222> LOCATION: (43)..(43)
<223> OTHER INFORMATION: X is absent or any amino acid
<220> FEATURE:
<221> NAME/KEY: MISC_FEATURE
<222> LOCATION: (44)..(44)
<223> OTHER INFORMATION: X is absent or any amino acid
<220> FEATURE:
<221> NAME/KEY: MISC_FEATURE
<222> LOCATION: (45)..(45)
<223> OTHER INFORMATION: X is absent or any amino acid
<220> FEATURE:
<221> NAME/KEY: MISC_FEATURE
<222> LOCATION: (46)..(46)
<223> OTHER INFORMATION: X is absent or any amino acid
<220> FEATURE:
<221> NAME/KEY: MISC_FEATURE
<222> LOCATION: (47)..(47)
<223> OTHER INFORMATION: X is absent or any amino acid
<220> FEATURE:
<221> NAME/KEY: MISC_FEATURE
<222> LOCATION: (48)..(48)
<223> OTHER INFORMATION: X is absent or any amino acid
<220> FEATURE:
<221> NAME/KEY: MISC_FEATURE
<222> LOCATION: (50)..(54)
<223> OTHER INFORMATION: X is any amino acid
<220> FEATURE:
<221> NAME/KEY: MISC_FEATURE
<222> LOCATION: (55)..(55)
<223> OTHER INFORMATION: X is absent or any amino acid
<220> FEATURE:
<221> NAME/KEY: MISC_FEATURE
<222> LOCATION: (56)..(56)
<223> OTHER INFORMATION: X is absent or any amino acid
<220> FEATURE:
<221> NAME/KEY: MISC_FEATURE
<222> LOCATION: (57)..(57)
<223> OTHER INFORMATION: X is absent or any amino acid
<220> FEATURE:
<221> NAME/KEY: MISC_FEATURE
<222> LOCATION: (58)..(58)
<223> OTHER INFORMATION: X is absent or any amino acid
<220> FEATURE:
<221> NAME/KEY: MISC_FEATURE
<222> LOCATION: (59)..(59)
<223> OTHER INFORMATION: X is absent or any amino acid
<220> FEATURE:
<221> NAME/KEY: MISC_FEATURE
<222> LOCATION: (60)..(60)
<223> OTHER INFORMATION: X is absent or any amino acid
<220> FEATURE:
<221> NAME/KEY: MISC_FEATURE
<222> LOCATION: (61)..(61)
<223> OTHER INFORMATION: X is absent or any amino acid
<220> FEATURE:
<221> NAME/KEY: MISC_FEATURE
<222> LOCATION: (62)..(62)
<223> OTHER INFORMATION: X is absent or any amino acid
<220> FEATURE:
<221> NAME/KEY: MISC_FEATURE
<222> LOCATION: (63)..(63)
<223> OTHER INFORMATION: X is absent or any amino acid
<220> FEATURE:
<221> NAME/KEY: MISC_FEATURE
<222> LOCATION: (64)..(64)
<223> OTHER INFORMATION: X is absent or any amino acid
<220> FEATURE:
<221> NAME/KEY: MISC_FEATURE
<222> LOCATION: (65)..(65)
<223> OTHER INFORMATION: X is absent or any amino acid
<220> FEATURE:
<221> NAME/KEY: MISC_FEATURE
<222> LOCATION: (66)..(66)
<223> OTHER INFORMATION: X is absent or any amino acid
<220> FEATURE:
<221> NAME/KEY: MISC_FEATURE
<222> LOCATION: (67)..(67)
<223> OTHER INFORMATION: X is absent or any amino acid
<220> FEATURE:
<221> NAME/KEY: MISC_FEATURE
<222> LOCATION: (68)..(68)
<223> OTHER INFORMATION: X is absent or any amino acid
<220> FEATURE:
<221> NAME/KEY: MISC_FEATURE
<222> LOCATION: (69)..(69)
<223> OTHER INFORMATION: X is absent or any amino acid
<220> FEATURE:
<221> NAME/KEY: MISC_FEATURE
<222> LOCATION: (71)..(95)
<223> OTHER INFORMATION: X is any amino acid
<220> FEATURE:
<221> NAME/KEY: MISC_FEATURE
<222> LOCATION: (88)..(113)
<223> OTHER INFORMATION: X is any amino acid
<220> FEATURE:
<221> NAME/KEY: MISC_FEATURE
<222> LOCATION: (96)..(96)
<223> OTHER INFORMATION: X is absent or any amino acid
<220> FEATURE:
<221> NAME/KEY: MISC_FEATURE
<222> LOCATION: (97)..(97)
<223> OTHER INFORMATION: X is absent or any amino acid
<220> FEATURE:
<221> NAME/KEY: MISC_FEATURE
<222> LOCATION: (98)..(98)
<223> OTHER INFORMATION: X is absent or any amino acid
<220> FEATURE:
<221> NAME/KEY: MISC_FEATURE
<222> LOCATION: (99)..(99)
<223> OTHER INFORMATION: X is absent or any amino acid
<220> FEATURE:
<221> NAME/KEY: MISC_FEATURE
<222> LOCATION: (100)..(100)
<223> OTHER INFORMATION: X is absent or any amino acid
<220> FEATURE:
<221> NAME/KEY: MISC_FEATURE
<222> LOCATION: (102)..(103)
<223> OTHER INFORMATION: X is any amino acid

<400> SEQUENCE: 21

```
Cys Xaa Pro Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Trp Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Trp Xaa Xaa His His Pro
            100                 105
```

<210> SEQ ID NO 22
<211> LENGTH: 8
<212> TYPE: PRT
<213> ORGANISM: Artificial Sequence
<220> FEATURE:
<223> OTHER INFORMATION: HA sequence element consensus sequence element

<400> SEQUENCE: 22

Gly Ala Ile Ala Gly Phe Ile Glu
1               5

<210> SEQ ID NO 23
<211> LENGTH: 23
<212> TYPE: PRT
<213> ORGANISM: Artificial Sequence
<220> FEATURE:
<223> OTHER INFORMATION: HA sequence element consensus sequence element
<220> FEATURE:
<221> NAME/KEY: MISC_FEATURE
<222> LOCATION: (2)..(5)
<223> OTHER INFORMATION: X = is any amino acid
<220> FEATURE:
<221> NAME/KEY: MISC_FEATURE
<222> LOCATION: (6)..(6)
<223> OTHER INFORMATION: X = is absent or any amino acid
<220> FEATURE:
<221> NAME/KEY: MISC_FEATURE
<222> LOCATION: (7)..(7)
<223> OTHER INFORMATION: X = is absent or any amino acid
<220> FEATURE:
<221> NAME/KEY: MISC_FEATURE
<222> LOCATION: (8)..(8)
<223> OTHER INFORMATION: X = is absent or any amino acid
<220> FEATURE:
<221> NAME/KEY: MISC_FEATURE
<222> LOCATION: (9)..(9)
<223> OTHER INFORMATION: X = is absent or any amino acid
<220> FEATURE:
<221> NAME/KEY: MISC_FEATURE
<222> LOCATION: (10)..(10)
<223> OTHER INFORMATION: X = is absent or any amino acid
<220> FEATURE:
<221> NAME/KEY: MISC_FEATURE
<222> LOCATION: (11)..(11)
<223> OTHER INFORMATION: X = is absent or any amino acid
<220> FEATURE:
<221> NAME/KEY: MISC_FEATURE
<222> LOCATION: (12)..(12)
<223> OTHER INFORMATION: X = is absent or any amino acid
<220> FEATURE:
<221> NAME/KEY: MISC_FEATURE
<222> LOCATION: (13)..(13)
<223> OTHER INFORMATION: X = is absent or any amino acid
<220> FEATURE:
<221> NAME/KEY: MISC_FEATURE
<222> LOCATION: (14)..(14)
<223> OTHER INFORMATION: X = is absent or any amino acid
<220> FEATURE:
<221> NAME/KEY: MISC_FEATURE
<222> LOCATION: (15)..(15)
<223> OTHER INFORMATION: X = is absent or any amino acid

<400> SEQUENCE: 23

Pro Xaa Xaa Xaa Xaa Xaa Xaa Xaa Xaa Xaa Xaa Xaa Xaa Xaa Xaa Gly
1               5                   10                  15

Ala Ile Ala Gly Phe Ile Glu
            20

<210> SEQ ID NO 24
<211> LENGTH: 570
<212> TYPE: PRT
<213> ORGANISM: Artificial Sequence
<220> FEATURE:
<223> OTHER INFORMATION: NCBI Sambucus Nigra Lectin Sequence

<400> SEQUENCE: 24

Met Arg Leu Val Ala Lys Leu Leu Tyr Leu Ala Val Leu Ala Ile Cys
1               5                   10                  15

```
Gly Leu Gly Ile His Gly Ala Leu Thr His Pro Arg Val Thr Pro Pro
            20                  25                  30

Val Tyr Pro Ser Val Ser Phe Asn Leu Thr Gly Ala Asp Thr Tyr Glu
        35                  40                  45

Pro Phe Leu Arg Ala Leu Gln Glu Lys Val Ile Leu Gly Asn His Thr
    50                  55                  60

Ala Phe Asp Leu Pro Val Leu Asn Pro Glu Ser Gln Val Ser Asp Ser
65                  70                  75                  80

Asn Arg Phe Val Leu Val Pro Leu Thr Asn Pro Ser Gly Asp Thr Val
                85                  90                  95

Thr Leu Ala Ile Asp Val Val Asn Leu Tyr Val Val Ala Phe Ser Ser
            100                 105                 110

Asn Gly Lys Ser Tyr Phe Phe Ser Gly Ser Thr Ala Val Gln Arg Asp
        115                 120                 125

Asn Leu Phe Val Asp Thr Thr Gln Glu Glu Leu Asn Phe Thr Gly Asn
    130                 135                 140

Tyr Thr Ser Leu Glu Arg Gln Val Gly Phe Gly Arg Val Tyr Ile Pro
145                 150                 155                 160

Leu Gly Pro Lys Ser Leu Asp Gln Ala Ile Ser Ser Leu Arg Thr Tyr
                165                 170                 175

Thr Leu Thr Ala Gly Asp Thr Lys Pro Leu Ala Arg Gly Leu Leu Val
            180                 185                 190

Val Ile Gln Met Val Ser Glu Ala Ala Arg Phe Arg Tyr Ile Glu Leu
        195                 200                 205

Arg Ile Arg Thr Ser Ile Thr Asp Ala Ser Glu Phe Thr Pro Asp Leu
    210                 215                 220

Leu Met Leu Ser Met Glu Asn Asn Trp Ser Ser Met Ser Ser Glu Ile
225                 230                 235                 240

Gln Gln Ala Gln Pro Gly Gly Ile Phe Ala Gly Val Val Gln Leu Arg
                245                 250                 255

Asp Glu Arg Asn Asn Ser Ile Glu Val Thr Asn Phe Arg Arg Leu Phe
            260                 265                 270

Glu Leu Thr Tyr Ile Ala Val Leu Leu Tyr Gly Cys Ala Pro Val Thr
        275                 280                 285

Ser Ser Ser Tyr Ser Asn Asn Ala Ile Asp Ala Gln Ile Ile Lys Met
    290                 295                 300

Pro Val Phe Arg Gly Gly Glu Tyr Glu Lys Val Cys Ser Val Val Glu
305                 310                 315                 320

Val Thr Arg Arg Ile Ser Gly Trp Asp Gly Leu Cys Val Asp Val Arg
                325                 330                 335

Tyr Gly His Tyr Ile Asp Gly Asn Pro Val Gln Leu Arg Pro Cys Gly
            340                 345                 350

Asn Glu Cys Asn Gln Leu Trp Thr Phe Arg Thr Asp Gly Thr Ile Arg
        355                 360                 365

Trp Leu Gly Lys Cys Leu Thr Ala Ser Ser Ser Val Met Ile Tyr Asp
    370                 375                 380

Cys Asn Thr Val Pro Pro Glu Ala Thr Lys Trp Val Val Ser Ile Asp
385                 390                 395                 400

Gly Thr Ile Thr Asn Pro His Ser Gly Leu Val Leu Thr Ala Pro Gln
                405                 410                 415

Ala Ala Glu Gly Thr Ala Leu Ser Leu Glu Asn Asn Ile His Ala Ala
            420                 425                 430

Arg Gln Gly Trp Thr Val Gly Asp Val Glu Pro Leu Val Thr Phe Ile
```

435 440 445

Val Gly Tyr Lys Gln Met Cys Leu Arg Glu Asn Gly Glu Asn Asn Phe
450 455 460

Val Trp Leu Glu Asp Cys Val Leu Asn Arg Val Gln Gln Glu Trp Ala
465 470 475 480

Leu Tyr Gly Asp Gly Thr Ile Arg Val Asn Ser Asn Arg Ser Leu Cys
485 490 495

Val Thr Ser Glu Asp His Glu Pro Ser Asp Leu Ile Val Ile Leu Lys
500 505 510

Cys Glu Gly Ser Gly Asn Gln Arg Trp Val Phe Asn Thr Asn Gly Thr
515 520 525

Ile Ser Asn Pro Asn Ala Lys Leu Leu Met Asp Val Ala Gln Arg Asp
530 535 540

Val Ser Leu Arg Lys Ile Ile Leu Tyr Arg Pro Thr Gly Asn Pro Asn
545 550 555 560

Gln Gln Trp Ile Thr Thr Thr His Pro Ala
565 570

<210> SEQ ID NO 25
<211> LENGTH: 569
<212> TYPE: PRT
<213> ORGANISM: Artificial Sequence
<220> FEATURE:
<223> OTHER INFORMATION: NCBI Sambucus Nigra Lectin Sequence

<400> SEQUENCE: 25

Met Lys Val Val Ala Thr Ile Leu Tyr Leu Val Val Leu Ala Ile Cys
1 5 10 15

Gly Leu Gly Ile His Gly Ala His Pro Thr His Ser Ala Pro Pro Thr
20 25 30

Val Tyr Pro Ser Val Ser Phe Asn Leu Thr Glu Ala Asn Ser Asn Glu
35 40 45

Tyr Arg His Phe Leu Gln Glu Leu Arg Gly Lys Val Ile Leu Gly Ser
50 55 60

His Arg Ala Phe Asp Leu Pro Val Leu Asn Pro Glu Ser Lys Val Ser
65 70 75 80

Asp Ser Asp Arg Phe Val Leu Val Arg Leu Thr Asn Pro Ser Arg Lys
85 90 95

Lys Val Thr Leu Ala Ile Asp Val Val Thr Phe Tyr Val Val Ala Phe
100 105 110

Ala Gln Asn Asp Arg Ser Tyr Phe Phe Ser Gly Ser Ser Glu Val Gln
115 120 125

Arg Glu Asn Leu Phe Val Asp Thr Thr Gln Glu Asp Leu Asn Phe Lys
130 135 140

Gly Asp Tyr Thr Ser Leu Glu His Gln Val Gly Phe Gly Arg Val Tyr
145 150 155 160

Ile Pro Leu Gly Pro Lys Ser Leu Ala Gln Ser Ile Ser Ser Leu Ser
165 170 175

Thr Tyr Lys Ser Ser Ala Gly Asp Asn Lys Arg Leu Ala Arg Ser Leu
180 185 190

Leu Val Val Ile Gln Met Val Ser Glu Ala Ala Arg Phe Arg Tyr Ile
195 200 205

Gln Leu Arg Ile Gln Ala Ser Ile Thr Asp Ala Lys Glu Phe Thr Pro
210 215 220

Asp Leu Leu Met Leu Ser Met Glu Asn Lys Trp Ser Ser Met Ser Ser

```
225                 230                 235                 240

Glu Ile Gln Gln Ala Gln Pro Gly Gly Ala Phe Ala Gln Val Val Lys
                245                 250                 255

Leu Leu Asp Gln Arg Asn His Pro Ile Asp Val Thr Asn Phe Arg Arg
            260                 265                 270

Leu Phe Gln Leu Thr Ser Val Ala Val Leu Leu His Gly Cys Pro Thr
        275                 280                 285

Val Thr Lys Met Pro Ala Tyr Ile Ile Lys Met Pro Val Phe Asn Gly
    290                 295                 300

Gly Glu Asp Glu Glu Arg Cys Ser Val Val Glu Glu Val Thr Arg Arg
305                 310                 315                 320

Ile Gly Gly Arg Asp Gly Phe Cys Ala Glu Val Lys Asn Gly Asp Glu
                325                 330                 335

Lys Asp Gly Thr Pro Val Gln Leu Ser Ser Cys Gly Glu Gln Ser Asn
            340                 345                 350

Gln Gln Trp Thr Phe Ser Thr Asp Gly Thr Ile Gln Ser Leu Gly Lys
        355                 360                 365

Cys Leu Thr Thr Ser Ser Ser Val Met Ile Tyr Asn Cys Lys Val Val
    370                 375                 380

Pro Pro Glu Ser Thr Lys Trp Val Val Ser Ile Asp Gly Thr Ile Thr
385                 390                 395                 400

Asn Pro Arg Ser Gly Leu Val Leu Thr Ala Pro Lys Ala Ala Glu Gly
                405                 410                 415

Thr Leu Val Ser Leu Glu Lys Asn Val His Ala Ala Arg Gln Gly Trp
            420                 425                 430

Ile Val Gly Asn Val Glu Pro Leu Val Thr Phe Ile Val Gly Tyr Glu
        435                 440                 445

Gln Met Cys Leu Glu Thr Asn Pro Gly Asn Asn Asp Val Ser Leu Gly
    450                 455                 460

Asp Cys Ser Val Lys Ser Ala Ser Lys Val Asp Gln Lys Trp Ala Leu
465                 470                 475                 480

Tyr Gly Asp Gly Thr Ile Arg Val Asn Asn Asp Arg Ser Leu Cys Val
                485                 490                 495

Thr Ser Glu Gly Lys Ser Ser Asn Glu Pro Ile Ile Ile Leu Lys Cys
            500                 505                 510

Leu Gly Trp Ala Asn Gln Arg Trp Val Phe Asn Thr Asp Gly Thr Ile
        515                 520                 525

Ser Asn Pro Asp Ser Lys Leu Val Met His Val Asp Gln Asn Asp Val
    530                 535                 540

Pro Leu Arg Lys Ile Ile Leu Ser His Pro Ser Gly Thr Ser Asn Gln
545                 550                 555                 560

Gln Trp Ile Ala Ser Thr His Pro Ala
                565
```

<210> SEQ ID NO 26
<211> LENGTH: 286
<212> TYPE: PRT
<213> ORGANISM: Artificial Sequence
<220> FEATURE:
<223> OTHER INFORMATION: NCBI Polyporous Squamosus Lectin 1a Sequence

<400> SEQUENCE: 26

```
Met Ser Phe Gln Gly His Gly Ile Tyr Tyr Ile Ala Ser Ala Tyr Val
1               5                   10                  15

Ala Asn Thr Arg Leu Ala Leu Ser Glu Asp Ser Ser Ala Asn Lys Ser
```

```
            20                  25                  30

Pro Asp Val Ile Ile Ser Ser Asp Ala Val Asp Pro Leu Asn Asn Leu
        35                  40                  45

Trp Leu Ile Glu Pro Val Gly Glu Ala Asp Thr Tyr Thr Val Arg Asn
    50                  55                  60

Ala Phe Ala Gly Ser Tyr Met Asp Leu Ala Gly His Ala Ala Thr Asp
65                  70                  75                  80

Gly Thr Ala Ile Ile Gly Tyr Arg Pro Thr Gly Gly Asp Asn Gln Lys
                85                  90                  95

Trp Ile Ile Ser Gln Ile Asn Asp Val Trp Lys Ile Lys Ser Lys Glu
            100                 105                 110

Thr Gly Thr Phe Val Thr Leu Leu Asn Gly Asp Gly Gly Gly Thr Gly
        115                 120                 125

Thr Val Val Gly Trp Gln Asn Ile Thr Asn Asn Thr Ser Gln Asn Trp
    130                 135                 140

Thr Phe Gln Lys Leu Ser Gln Thr Gly Ala Asn Val His Ala Thr Leu
145                 150                 155                 160

Leu Ala Cys Pro Ala Leu Arg Gln Asp Phe Lys Ser Tyr Leu Ser Asp
                165                 170                 175

Gly Leu Tyr Leu Val Leu Thr Arg Asp Gln Ile Ser Ser Ile Trp Gln
            180                 185                 190

Ala Ser Gly Leu Gly Ser Thr Pro Trp Arg Ser Glu Ile Phe Asp Cys
        195                 200                 205

Asp Asp Phe Ala Thr Val Phe Lys Gly Ala Val Ala Lys Trp Gly Asn
    210                 215                 220

Glu Asn Phe Lys Ala Asn Gly Phe Ala Leu Leu Cys Gly Leu Met Phe
225                 230                 235                 240

Gly Ser Lys Ser Ser Gly Ala His Ala Tyr Asn Trp Phe Val Glu Arg
                245                 250                 255

Gly Asn Phe Ser Thr Val Thr Phe Phe Glu Pro Gln Asn Gly Thr Tyr
            260                 265                 270

Ser Ala Asn Ala Trp Asp Tyr Lys Ala Tyr Phe Gly Leu Phe
        275                 280                 285


<210> SEQ ID NO 27
<211> LENGTH: 292
<212> TYPE: PRT
<213> ORGANISM: Artificial Sequence
<220> FEATURE:
<223> OTHER INFORMATION: NCBI Polyporous Squamosus Lectin 1b sequence

<400> SEQUENCE: 27

Met Ser Phe Glu Gly His Gly Ile Tyr His Ile Pro His Ala His Val
1               5                   10                  15

Ala Asn Ile Arg Met Ala Leu Ala Asn Arg Gly Ser Gly Gln Asn Gly
            20                  25                  30

Thr Pro Val Ile Ala Trp Asp Ser Asn Asn Asp Ala Phe Asp His Met
        35                  40                  45

Trp Leu Val Glu Pro Thr Gly Glu Ala Asp Thr Tyr Thr Ile His Asn
    50                  55                  60

Val Ser Thr Gly Thr Tyr Met Asp Val Thr Ala Ser Ala Val Ala Asp
65                  70                  75                  80

Asn Thr Pro Ile Ile Gly Tyr Gln Arg Thr Gly Asn Asp Asn Gln Lys
                85                  90                  95

Trp Ile Ile Arg Gln Val Gln Thr Asp Gly Gly Asp Arg Pro Trp Lys
```

```
            100                 105                 110

Ile Gln Cys Lys Ala Thr Gly Thr Phe Ala Thr Leu Tyr Ser Gly Gly
        115                 120                 125

Gly Ser Gly Thr Ala Ile Val Gly Trp Arg Leu Val Asn Ser Asn Gly
    130                 135                 140

Asn Gln Asp Trp Val Phe Gln Lys Leu Ser Gln Thr Ser Val Asn Val
145                 150                 155                 160

His Ala Thr Leu Leu Ala Cys Gly Ala Thr Val Gly Gln Asp Phe Lys
                165                 170                 175

Asn Tyr Leu Tyr Asp Gly Leu Tyr Leu Val Leu Pro Arg Asp Arg Ile
            180                 185                 190

Ser Ala Ile Trp Lys Ala Ser Gly Leu Gly Glu Thr Ala Arg Arg Asp
        195                 200                 205

Gly Ile Tyr Asp Ser Asp Glu Phe Ala Met Thr Phe Lys Ser Ala Ala
    210                 215                 220

Ala Thr Trp Gly Lys Glu Asn Phe Lys Ala Asp Gly Phe Ala Ile Leu
225                 230                 235                 240

Cys Gly Met Met Phe Gly Thr Lys Ala Ser Thr Asn Arg His Ala Tyr
                245                 250                 255

Asn Trp Val Val Glu Arg Gly Ser Phe Ser Thr Val Thr Phe Phe Glu
            260                 265                 270

Pro Gln Asn Gly Thr Tyr Ser Asp Asp Ala Trp Gly Tyr Lys Ala Tyr
        275                 280                 285

Phe Gly Leu Phe
    290
```

<210> SEQ ID NO 28
<211> LENGTH: 139
<212> TYPE: PRT
<213> ORGANISM: Artificial Sequence
<220> FEATURE:
<223> OTHER INFORMATION: Engineered HA Polypeptide
<220> FEATURE:
<221> NAME/KEY: MISC_FEATURE
<222> LOCATION: (1)..(1)
<223> OTHER INFORMATION: X = Arg, Lys, Gln, Met or His
<220> FEATURE:
<221> NAME/KEY: MISC_FEATURE
<222> LOCATION: (2)..(41)
<223> OTHER INFORMATION: X = is any amino acid
<220> FEATURE:
<221> NAME/KEY: MISC_FEATURE
<222> LOCATION: (42)..(42)
<223> OTHER INFORMATION: X = is absent or any amino acid
<220> FEATURE:
<221> NAME/KEY: MISC_FEATURE
<222> LOCATION: (43)..(43)
<223> OTHER INFORMATION: X = is absent or any amino acid
<220> FEATURE:
<221> NAME/KEY: MISC_FEATURE
<222> LOCATION: (44)..(44)
<223> OTHER INFORMATION: X = is absent or any amino acid
<220> FEATURE:
<221> NAME/KEY: MISC_FEATURE
<222> LOCATION: (45)..(45)
<223> OTHER INFORMATION: X = is absent or any amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: X = is absent or any amino acid
<220> FEATURE:
<221> NAME/KEY: MISC_FEATURE
<222> LOCATION: (48)..(48)
<223> OTHER INFORMATION: X = is absent or any amino acid
<220> FEATURE:
<221> NAME/KEY: MISC_FEATURE
<222> LOCATION: (49)..(49)
<223> OTHER INFORMATION: X = is absent or any amino acid
<220> FEATURE:
<221> NAME/KEY: MISC_FEATURE
<222> LOCATION: (50)..(50)
<223> OTHER INFORMATION: X = is absent or any amino acid
<220> FEATURE:
<221> NAME/KEY: MISC_FEATURE
<222> LOCATION: (51)..(51)
<223> OTHER INFORMATION: X = is absent or any amino acid
<220> FEATURE:
<221> NAME/KEY: MISC_FEATURE
<222> LOCATION: (52)..(52)
<223> OTHER INFORMATION: X = is absent or any amino acid
<220> FEATURE:
<221> NAME/KEY: MISC_FEATURE
<222> LOCATION: (53)..(53)
<223> OTHER INFORMATION: X = is absent or any amino acid
<220> FEATURE:
<221> NAME/KEY: MISC_FEATURE
<222> LOCATION: (54)..(54)
<223> OTHER INFORMATION: X = is absent or any amino acid
<220> FEATURE:
<221> NAME/KEY: MISC_FEATURE
<222> LOCATION: (55)..(55)
<223> OTHER INFORMATION: X = is absent or any amino acid
<220> FEATURE:
<221> NAME/KEY: MISC_FEATURE
<222> LOCATION: (56)..(56)
<223> OTHER INFORMATION: X = is absent or any amino acid
<220> FEATURE:
<221> NAME/KEY: MISC_FEATURE
<222> LOCATION: (57)..(57)
<223> OTHER INFORMATION: X = is absent or any amino acid
<220> FEATURE:
<221> NAME/KEY: MISC_FEATURE
<222> LOCATION: (58)..(58)
<223> OTHER INFORMATION: X = is absent or any amino acid
<220> FEATURE:
<221> NAME/KEY: MISC_FEATURE
<222> LOCATION: (59)..(59)
<223> OTHER INFORMATION: X = is absent or any amino acid
<220> FEATURE:
<221> NAME/KEY: MISC_FEATURE
<222> LOCATION: (60)..(60)
<223> OTHER INFORMATION: X = is absent or any amino acid
<220> FEATURE:
<221> NAME/KEY: MISC_FEATURE
<222> LOCATION: (61)..(61)
<223> OTHER INFORMATION: X = is absent or any amino acid
<220> FEATURE:
<221> NAME/KEY: MISC_FEATURE
<222> LOCATION: (62)..(62)
<223> OTHER INFORMATION: X = is absent or any amino acid
<220> FEATURE:
<221> NAME/KEY: MISC_FEATURE
<222> LOCATION: (63)..(63)
<223> OTHER INFORMATION: X = is absent or any amino acid
<220> FEATURE:
<221> NAME/KEY: MISC_FEATURE
<222> LOCATION: (64)..(64)
<223> OTHER INFORMATION: X = is absent or any amino acid
<220> FEATURE:
<221> NAME/KEY: MISC_FEATURE
<222> LOCATION: (65)..(65)
<223> OTHER INFORMATION: X = is absent or any amino acid
<220> FEATURE:
<221> NAME/KEY: MISC_FEATURE
<222> LOCATION: (66)..(66)
<223> OTHER INFORMATION: X = is absent or any amino acid
<220> FEATURE:
<221> NAME/KEY: MISC_FEATURE
<222> LOCATION: (67)..(67)
<223> OTHER INFORMATION: X = is absent or any amino acid
<220> FEATURE:

<221> NAME/KEY: MISC_FEATURE
<222> LOCATION: (68)..(68)
<223> OTHER INFORMATION: X = is absent or any amino acid
<220> FEATURE:
<221> NAME/KEY: MISC_FEATURE
<222> LOCATION: (69)..(69)
<223> OTHER INFORMATION: X = is absent or any amino acid
<220> FEATURE:
<221> NAME/KEY: MISC_FEATURE
<222> LOCATION: (70)..(70)
<223> OTHER INFORMATION: X = is absent or any amino acid
<220> FEATURE:
<221> NAME/KEY: MISC_FEATURE
<222> LOCATION: (71)..(71)
<223> OTHER INFORMATION: X = is absent or any amino acid
<220> FEATURE:
<221> NAME/KEY: MISC_FEATURE
<222> LOCATION: (72)..(72)
<223> OTHER INFORMATION: X = Ala, Asp, Glu, Leu, Ile, Met, Ser, Thr, Cys or Val
<220> FEATURE:
<221> NAME/KEY: MISC_FEATURE
<222> LOCATION: (73)..(92)
<223> OTHER INFORMATION: X = is any amino acid
<220> FEATURE:
<221> NAME/KEY: MISC_FEATURE
<222> LOCATION: (93)..(93)
<223> OTHER INFORMATION: X = is absent or any amino acid
<220> FEATURE:
<221> NAME/KEY: MISC_FEATURE
<222> LOCATION: (94)..(94)
<223> OTHER INFORMATION: X = is absent or any amino acid
<220> FEATURE:
<221> NAME/KEY: MISC_FEATURE
<222> LOCATION: (95)..(95)
<223> OTHER INFORMATION: X = is absent or any amino acid
<220> FEATURE:
<221> NAME/KEY: MISC_FEATURE
<222> LOCATION: (96)..(96)
<223> OTHER INFORMATION: X = is absent or any amino acid
<220> FEATURE:
<221> NAME/KEY: MISC_FEATURE
<222> LOCATION: (97)..(97)
<223> OTHER INFORMATION: X = is absent or any amino acid
<220> FEATURE:
<221> NAME/KEY: MISC_FEATURE
<222> LOCATION: (98)..(98)
<223> OTHER INFORMATION: X = is absent or any amino acid
<220> FEATURE:
<221> NAME/KEY: MISC_FEATURE
<222> LOCATION: (99)..(99)
<223> OTHER INFORMATION: X = is absent or any amino acid
<220> FEATURE:
<221> NAME/KEY: MISC_FEATURE
<222> LOCATION: (100)..(100)
<223> OTHER INFORMATION: X = is absent or any amino acid
<220> FEATURE:
<221> NAME/KEY: MISC_FEATURE
<222> LOCATION: (101)..(101)
<223> OTHER INFORMATION: X = is absent or any amino acid
<220> FEATURE:
<221> NAME/KEY: MISC_FEATURE
<222> LOCATION: (102)..(102)
<223> OTHER INFORMATION: X = is absent or any amino acid
<220> FEATURE:
<221> NAME/KEY: MISC_FEATURE
<222> LOCATION: (103)..(103)
<223> OTHER INFORMATION: X = is absent or any amino acid
<220> FEATURE:
<221> NAME/KEY: MISC_FEATURE
<222> LOCATION: (104)..(104)
<223> OTHER INFORMATION: X = is absent or any amino acid
<220> FEATURE:
<221> NAME/KEY: MISC_FEATURE
<222> LOCATION: (105)..(105)
<223> OTHER INFORMATION: X = is absent or any amino acid
<220> FEATURE:
<221> NAME/KEY: MISC_FEATURE
<222> LOCATION: (106)..(106)

<223> OTHER INFORMATION: X = is absent or any amino acid
<220> FEATURE:
<221> NAME/KEY: MISC_FEATURE
<222> LOCATION: (107)..(107)
<223> OTHER INFORMATION: X = is absent or any amino acid
<220> FEATURE:
<221> NAME/KEY: MISC_FEATURE
<222> LOCATION: (108)..(108)
<223> OTHER INFORMATION: X = is absent or any amino acid
<220> FEATURE:
<221> NAME/KEY: MISC_FEATURE
<222> LOCATION: (109)..(109)
<223> OTHER INFORMATION: X = is absent or any amino acid
<220> FEATURE:
<221> NAME/KEY: MISC_FEATURE
<222> LOCATION: (110)..(110)
<223> OTHER INFORMATION: X = is absent or any amino acid
<220> FEATURE:
<221> NAME/KEY: MISC_FEATURE
<222> LOCATION: (111)..(111)
<223> OTHER INFORMATION: X = is absent or any amino acid
<220> FEATURE:
<221> NAME/KEY: MISC_FEATURE
<222> LOCATION: (112)..(112)
<223> OTHER INFORMATION: X = is absent or any amino acid
<220> FEATURE:
<221> NAME/KEY: MISC_FEATURE
<222> LOCATION: (113)..(113)
<223> OTHER INFORMATION: X = is absent or any amino acid
<220> FEATURE:
<221> NAME/KEY: MISC_FEATURE
<222> LOCATION: (114)..(114)
<223> OTHER INFORMATION: X = is absent or any amino acid
<220> FEATURE:
<221> NAME/KEY: MISC_FEATURE
<222> LOCATION: (115)..(115)
<223> OTHER INFORMATION: X = is absent or any amino acid
<220> FEATURE:
<221> NAME/KEY: MISC_FEATURE
<222> LOCATION: (116)..(116)
<223> OTHER INFORMATION: X = is absent or any amino acid
<220> FEATURE:
<221> NAME/KEY: MISC_FEATURE
<222> LOCATION: (117)..(117)
<223> OTHER INFORMATION: X = is absent or any amino acid
<220> FEATURE:
<221> NAME/KEY: MISC_FEATURE
<222> LOCATION: (118)..(118)
<223> OTHER INFORMATION: X = is absent or any amino acid
<220> FEATURE:
<221> NAME/KEY: MISC_FEATURE
<222> LOCATION: (119)..(119)
<223> OTHER INFORMATION: X = is absent or any amino acid
<220> FEATURE:
<221> NAME/KEY: MISC_FEATURE
<222> LOCATION: (120)..(120)
<223> OTHER INFORMATION: X = is absent or any amino acid
<220> FEATURE:
<221> NAME/KEY: MISC_FEATURE
<222> LOCATION: (121)..(121)
<223> OTHER INFORMATION: X = is absent or any amino acid
<220> FEATURE:
<221> NAME/KEY: MISC_FEATURE
<222> LOCATION: (122)..(122)
<223> OTHER INFORMATION: X = is absent or any amino acid
<220> FEATURE:
<221> NAME/KEY: MISC_FEATURE
<222> LOCATION: (123)..(123)
<223> OTHER INFORMATION: X = Ala, Cys, Gly, Ile, Leu, Met, Phe, Pro, Trp, or Val
<220> FEATURE:
<221> NAME/KEY: MISC_FEATURE
<222> LOCATION: (124)..(124)
<223> OTHER INFORMATION: X = is any amino acid
<220> FEATURE:
<221> NAME/KEY: MISC_FEATURE
<222> LOCATION: (125)..(125)
<223> OTHER INFORMATION: X = is absent or any amino acid
<220> FEATURE:

<221> NAME/KEY: MISC_FEATURE
<222> LOCATION: (126)..(126)
<223> OTHER INFORMATION: X = is absent or any amino acid
<220> FEATURE:
<221> NAME/KEY: MISC_FEATURE
<222> LOCATION: (127)..(127)
<223> OTHER INFORMATION: X = is absent or any amino acid
<220> FEATURE:
<221> NAME/KEY: MISC_FEATURE
<222> LOCATION: (128)..(128)
<223> OTHER INFORMATION: X = is absent or any amino acid
<220> FEATURE:
<221> NAME/KEY: MISC_FEATURE
<222> LOCATION: (129)..(129)
<223> OTHER INFORMATION: X = is absent or any amino acid
<220> FEATURE:
<221> NAME/KEY: MISC_FEATURE
<222> LOCATION: (130)..(130)
<223> OTHER INFORMATION: X = is absent or any amino acid
<220> FEATURE:
<221> NAME/KEY: MISC_FEATURE
<222> LOCATION: (131)..(131)
<223> OTHER INFORMATION: X = is absent or any amino acid
<220> FEATURE:
<221> NAME/KEY: MISC_FEATURE
<222> LOCATION: (132)..(132)
<223> OTHER INFORMATION: X = is absent or any amino acid
<220> FEATURE:
<221> NAME/KEY: MISC_FEATURE
<222> LOCATION: (133)..(133)
<223> OTHER INFORMATION: X = is absent or any amino acid
<220> FEATURE:
<221> NAME/KEY: MISC_FEATURE
<222> LOCATION: (134)..(134)
<223> OTHER INFORMATION: X = is absent or any amino acid
<220> FEATURE:
<221> NAME/KEY: MISC_FEATURE
<222> LOCATION: (135)..(135)
<223> OTHER INFORMATION: X = is absent or any amino acid
<220> FEATURE:
<221> NAME/KEY: MISC_FEATURE
<222> LOCATION: (136)..(136)
<223> OTHER INFORMATION: X = is absent or any amino acid
<220> FEATURE:
<221> NAME/KEY: MISC_FEATURE
<222> LOCATION: (137)..(137)
<223> OTHER INFORMATION: X = is absent or any amino acid
<220> FEATURE:
<221> NAME/KEY: MISC_FEATURE
<222> LOCATION: (138)..(138)
<223> OTHER INFORMATION: X = is absent or any amino acid
<220> FEATURE:
<221> NAME/KEY: MISC_FEATURE
<222> LOCATION: (139)..(139)
<223> OTHER INFORMATION: X = Arg, Asp, Glu, Gln, His, Lys, Ser, Gly,
Thr, or Tyr

<400> SEQUENCE: 28

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110
```

-continued

```
Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa
    130                 135
```

INFLUENZA TREATMENT AND/OR CHARACTERIZATION, HUMAN-ADAPTED HA POLYPEPTIDES; VACCINES

RELATED APPLICATIONS

This patent application is a continuation of U.S. application Ser. No. 13/239,376, filed on Sep. 21, 2011, which claims priority to U.S. provisional Patent Application Ser. No. 61/384,780, filed Sep. 21, 2010, the disclosure of which is incorporated herein in its entirety.

GOVERNMENT SUPPORT

This invention was made with government support under Grant Nos. R37 GM057073 and U54 GM2116 awarded by the National Institutes of Health. The government has certain rights in this invention.

BACKGROUND OF THE INVENTION

Influenza has a long history of pandemics, epidemics, resurgences and outbreaks. Among influenza strains, H2 strains pose particular challenges in light of the waning population immunity to H2 hemagglutinin. There is a need for vaccines and therapeutic strategies for effective treatment or delay of onset of disease caused by influenza virus; there is a particular need for vaccines and therapeutic strategies for effective treatment or delay of onset of disease caused by H2 influenza viruses.

SUMMARY OF THE INVENTION

The present invention provides binding agents that show a strong ability to discriminate between umbrella-topology and cone-topology glycans. In some embodiments, provided binding agents are engineered HA polypeptides. In some embodiments, provided binding agents are engineered H2 HA polypeptides. In some embodiments, provided binding agents show an ability to discriminate between umbrella-topology and cone-topology glycans that is at least effective as that shown by an RTLS HA polypeptide (e.g., an RTLS H2 HA polypeptide) as described herein.

In some embodiments, the present invention provides, among other things, engineered hemagglutinin (HA) polypeptides that include a sequence element referred to herein as “RTLS”. As described herein, the RTLS element refers to the presence of particular amino acids at positions corresponding to residues 137, 193, 226, and 228 of the HA polypeptide. In some embodiments, the present invention provides improvements to engineered HA polypeptides, for example in that the improved engineered HA polypeptides have certain particular amino acids residues at positions corresponding to 137, 193, 226, and 228. As described herein, such HA polypeptides have a variety of unexpected and useful characteristics as compared with prior art HA polypeptides, including prior art engineered HA polypeptides.

The present invention also provides, for example, diagnostic and therapeutic reagents and methods associated with provided binding agents, including vaccines. Among other things, provided reagents and methods are useful in the practice of medicine, for example in the delivery of vaccines and/or for the treatment or prevention of infection, for example with the influenza virus. In some embodiments, provided reagents and methods are particularly useful in the treatment of humans. In some embodiments, the present invention provides improvements to certain diagnostic and/or therapeutic reagents and methods, which improvement comprises, for example, inclusion, preparation and/or use of an engineered HA polypeptide as described herein, and/or of an HA polypeptide having certain particular amino acids residues at positions corresponding to 137, 193, 226, and 228.

The present invention also provides, for example, systems and reagents for identifying binding agents that effectively discriminate between umbrella-topology and cone-topology glycans. In some embodiments, such binding agents show at least as strong an ability to discriminate as does an RTLS HA polypeptide (e.g., an RTLS H2 HA polypeptide) as described herein. In some embodiments, provided binding agents show enhanced binding to umbrella-topology glycans as compared with a particular reference. In some embodiments, provided binding agents show reduced binding to cone-topology glycans as compared with a particular reference. In some embodiments, provided binding agents show both enhanced binding to umbrella-topology glycans and reduced ability to cone-topology glycans as compared with a particular reference. In some embodiments, the particular reference is a wild-type HA polypeptide. In some embodiments the particular reference is a wild-type H2 HA polypeptide. In some embodiments the particular reference is an RTLS HA polypeptide (e.g., an RTLS H2HA polypeptide). In some embodiments, the present invention provides improved systems and/or methods for identifying desirable binding agents, wherein the improvement comprises use (e.g., comparison with) of an HA polypeptide (e.g., an engineered polypeptide) having certain particular amino acids residues at positions corresponding to 137, 193, 226, and 228.

In some embodiments, provided binding agents (including provided HA polypeptides, e.g., engineered HA polypeptides) show an affinity (Kd') for umbrella-topology glycans within the range of about 1.5 nM to about 2 pM. In some embodiments, provided binding agents show an affinity (Kd') for umbrella-topology glycans within the range of about 1.5 nM to about 200 pM. In some embodiments, provided binding agents show an affinity (Kd') for umbrella-topology glycans within the range of about 200 pM to about 10 pM. In some embodiments, provided binding agents show an affinity (Kd') for umbrella-topology glycans within the range of about 10 pM to about 2 pM. In some embodiments, provided binding agents show an affinity (Kd') for cone-topology glycans that is not less than 2 nM; in some embodiments, provided binding agents show an affinity (Kd') for cone-topology glycans that is within the range of about 200 pM to about 2 nM. In some embodiments, provided binding agents show a relative affinity for umbrella glycans vs cone glycans that is about 1, about 2, about 3, about 4, about 5, about 6, about 7, about 8, about 9, about 10, about 20, about 30, about 40, about 50, about 60, about 70, about 80, about 90, about 100, about 200, about 300, about 400, about 500, about 600, about 700, about 800, about 900, about 1000, about 2000, about 3000, about 4000, about 5000, about 6000, about 7000, about 8000, about 9000, about 10,000, up to about 100,000 or more. In some embodiments, inventive binding agents show an affinity for umbrella topology glycans that is about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, about 10,000% or more than their affinity for cone topology glycans.

In some embodiments, the present invention provides HA polypeptides (e.g., engineered HA polypeptides) whose amino acid sequence includes an element as set forth below:

X137 L1 X193 L2 X226 L3 X228 (SEQ ID NO. 28), wherein:

X137 is an amino acid selected from the group consisting of arginine, lysine, glutamine, methionine and histidine; in some embodiments, X137 is selected from the group consisting of arginine and lysine; in some embodiments, X137 arginine;

L1 is a linker comprising approximately 40-70 amino acids;

X193 is an amino acid selected from the group consisting of alanine, aspartic acid, glutamic acid, leucine, isoleucine, methionine, serine, threonine, cysteine, and valine; in some embodiments, X193 is selected from the group consisting of alanine, glutamic acid and threonine; in some embodiments, X193 is threonine;

L2 is a linker comprising approximately 20-50 amino acids;

X226 is an amino acid selected from the group consisting of alanine, cysteine, glycine, isoleucine, leucine, methionine, phenylalanine, proline, tryptophan, and valine; in some embodiments, X226 is selected from the group consisting of leucine, isoleucine, and valine; in some embodiments, X226 is leucine;

L2 is a linker comprising approximately 1-15 amino acids;

X228 is an amino acid selected from the group consisting of arginine, asparagine, aspartic acid, glutamic acid, glutamine, histidine, lysine, serine, glycine, threonine, and tyrosine; in some embodiments, X228 is selected from the group consisting of arginine, asparagine, serine, and threonine; in some embodiments, X228 is serine.

In some embodiments, each of L1, L2, and L3 has a length and amino acid sequence so that X137, X193, X226, and X228 are arranged with respect to one another in three dimensions space substantially as are residues 137, 193, 226, and 228 as shown in FIG. 17 and/or 18, and/or as in an HA polypeptide selected from the group consisting of SEQ ID NO: 1, SEQ ID NO: 2, SEQ ID NO: 3, SEQ ID NO: 4, SEQ ID NO: 6 and SEQ ID NO: 7. In some embodiments, L1 comprises approximately 40-70 amino acids; in some embodiments, L1 comprises 50-60 amino acids; in some embodiments, L1 comprises 53-58 amino acids. In some embodiments, L1 is approximately 56 amino acids long and has an amino acid sequence showing at least 80%, at least 85%, at least 90%, at least 95%, at least 96%, at least 97%, at least 98%, at least 99% or 100% identity with residues 138 to 192 of SEQ ID NO: 2. In some embodiments, L2 comprises approximately 20-50 amino acids; in some embodiments, L2 comprises 30-40 amino acids; in some embodiments, L2 comprises 32-35 amino acids. In some embodiments, L2 is approximately 33 amino acids long and has an amino acid sequences showing at least 80%, at least 85%, at least 90%, at least 95%, at least 96%, at least 97%, at least 98%, at least 99% or 100% identity with residues 194 to 225 of SEQ ID NO: 2. In some embodiments, L3 comprises approximately 1-15 amino acids; in some embodiments, L3 comprises 1-10 amino acids; in some embodiments, L3 comprises 1-5 amino acids. In some embodiments, L3 is approximately 1 amino acid long and has an amino acid sequences showing 100% identity with residue 227 of SEQ ID NO: 2.

In one aspect, the present invention provides the particular recognition that high affinity binding to umbrella-topology glycans alone may not be sufficient to confer effective transmission to/infectivity of humans. Rather, the present invention provides the insight that reduced binding to cone-topology glycans may also be important.

BRIEF DESCRIPTION OF THE DRAWINGS

FIG. 1A shows an alignment for positions 1 to 120 of consensus sequences (SEQ ID NO. 1); BAA02771A/Adachi/2/57 (H2N2) (SEQ ID NO. 2); ABP49470 A/Albany/1/1958 (H2N2) (SEQ ID NO. 3); AB044090 A/Albany/1/1959 (H2N2) (SEQ ID NO. 4); AB001355 A/Albany/1/1960 (H2N2) (SEQ ID NO. 5); AB052247 A/Albany/1/1968 (H2N2) (SEQ ID NO. 6); ACV49600 A/Japan/305/1957 (H2N2) (SEQ ID NO. 7); BAC43764 A/Kayano/57 (H2N2) (SEQ ID NO. 8); ACD88670 A/Chicken/PA/298101-4/2004 (H2N2) (SEQ ID NO. 9); ACJ69319 A/Chicken/Pennsylvania/SG-00426/2004 (H2N2) (SEQ ID NO. 10); and ACJ69324 A/Chicken/Pennsylvania/SG-00426/2004 (H2N2) (SEQ ID NO. 11). FIG. 1B shows an alignment of the same consensus sequences in FIG. 1A for positions 121 to 240. FIG. 1C shows an alignment of the same consensus sequences in FIG. 1A for positions 241 to 360. FIG. 1D shows an alignment of the same consensus sequences in FIG. 1A for positions 361 to 480. FIG. 1E shows an alignment of the same consensus sequences in FIG. 1A for positions 481 to 562.

FIG. 2A shows an alignment for positions 1 to 120 of consensus sequences (SEQ ID NO. 12); AAB69805 A/Alaska/84/57 (H3N2) (SEQ ID NO. 13); ABP49514 A/Albany/10/1968 (H3N2) (SEQ ID NO. 14); AB058928 A/Bangkok/2/1979 (H3N2) (SEQ ID NO. 15); ACF41735 A/Hong Kong/1-1-MA-12/1968 (H3N2) (SEQ ID NO. 16); ABB54514 A/Memphis/1/1968 (H3N2) (SEQ ID NO. 17); AAT64722 A/Netherlands/209/80 (H3N2) (SEQ ID NO. 18); ALL60153 A/Oregon/4/80 (H3N2) (SEQ ID NO. 19); and ACH95743 A/Taiwan/VGHYM0109-12/1984 (H3N2) (SEQ ID NO. 20). FIG. 2B shows an alignment of the same consensus sequences in FIG. 2A for positions 121 to 240. FIG. 2C shows an alignment of the same consensus sequences in FIG. 2A for positions 241 to 360. FIG. 2D shows an alignment of the same consensus sequences in FIG. 2A for positions 361 to 480. FIG. 2E shows an alignment of the same consensus sequences in FIG. 2A for positions 481 to 566.

FIG. 4A(1-7) shows certain exemplary (but not exhaustive) N- and O-linked glycan structures that can adopt umbrella topologies. FIG. 4B shows certain exemplary (but not exhaustive) O-linked glycan structures that can adopt umbrella topologies.

FIG. 5A shows exemplary dose-dependent direct glycan array binding of Alb58 HA which shows high affinity binding to human receptors in comparison with avian receptor binding. FIG. 5B shows exemplary extensive staining of apical surface of human tracheal epithelia and observable staining of alveolar tissue section by Alb58 HA (lighter) shown against propidium idodide staining (darker).

FIG. 6A shows are certain exemplary dose-dependent glycan array binding of an Alb58-LG mutant. A single amino acid change from Ser228→Gly (Alb58-LG mutant) leads to a loss of avian receptor binding observed in Alb58 HA. FIG. 6B shows certain exemplary dose-dependent glycan array binding of an Alb58-QG mutant. An additional Leu226→Gln mutation (on Alb58-LG) completely transforms the binding specificity by making the Alb58-QG mutant bind predominantly to avian receptors. FIG. 6C shows certain exemplary dose-dependent glycan array binding of an Alb58-QS mutant. Alb58-QS mutant shows loss of both avian and human receptor binding. FIG. 6D shows exemplary homology based structural model of Alb58-QS mutant (RBS part is shown as a cartoon) with the human receptor. Both the Leu226 and Gln226 side chains are marked. The Gln226 in the mutant is positioned to interact with Ser228 hence making the 226 position less favorable for contacts with both human and avian receptors.

FIG. 7A shows exemplary dose-dependent direct glycan array binding of CkPA04 HA which shows high affinity binding to avian receptors in comparison with human receptors. FIG. 7B shows exemplary extensive alveolar staining and minimal staining of apical surface of the human tracheal epithelia by CkPA04 HA (lighter) shown against propidium idodide staining (darker).

FIG. 8A shows exemplary stereo view of the RBS (shown as cartoon) of CkPA04 HA—avian receptor structural complex constructed using co-crystal structure of A/Chicken/NY/91-avian receptor (PRB ID: 2WR2) as a template. The resolved coordinates of the avian receptor (Neu5Acα2→3Galβ1→3GlcNAc) are shown using a stick representation. FIG. 8B shows exemplary stereo view of RBS (shown as cartoon) of Alb58 HA—human receptor complex constructed using co-crystal structure of A/Singapore/1/57—human receptor (PDB ID: 2WR7) as the template. The resolved coordinates of the human receptor (Neu5Acα2→6Galβ1→4GlcNAcβ1→3Gal) are shown using a stick representation. The side chains of the key residues involved in interaction with glycan receptor are shown and labeled. The residues in the RBS that differ between CkPA04 and Alb58 HA are underlined.

FIG. 9A shows exemplary dose-dependent glycan receptor binding of CkPA04-LS. FIG. 9B shows exemplary human tissue binding of CkPA04-LS. FIG. 9C shows exemplary dose-dependent glycan receptor binding of CkPA04-TLS. FIG. 9D shows exemplary human tissue binding of CkPA04-TLS. FIG. 9E shows exemplary dose-dependent glycan receptor binding of CkPA04-RTLS. FIG. 9F shows exemplary human tissue binding of CkPA04-RTLS. All the mutants show substantial improvement in the human receptor binding and reduction in avian receptor binding in comparison to the WT CkPA04 HA as observed in both the glycan array tissue-binding experiments.

FIG. 10A shows certain exemplary theoretical binding curves (with the apparent binding constant Kd') that depict the differences in the binding affinity of the WT and mutant H2N2 HAs to the representative avian receptor (3'SLN-LN). FIG. 10B shows certain exemplary theoretical binding curves that depict the differences in the binding affinity of the WT and mutant H2N2 HAs to the representative human receptor (6'SLN-LN). The range of Kd' values (3-8 pM) is shown for CkPA04-TLS, Alb58 and CkPA04-RTLS that is contrasted with the Kd' value of CkPA04-LS. The binding curves were generated by fitting to the Hill equation (see Methods) and plotting the theoretically calculated fractional saturation (y-axis) against HA concentration (x-axis). The n value for all the binding events is around 1.3.

FIG. 11A shows the conformational map of Neu5Acα2-3Gal linkage. The encircled region 2 is the trans conformation observed in the APR34_H1_23, ADU63_H3_23 and ADS97_H5_23 co-crystal structures. The encircled region 1 is the conformation observed in the AAI68_H3_23 co-crystal structure. FIG. 11B shows the conformational map of Neu5Acα2-6Gal where the cis-conformation (encircled region 3) is observed in all the HA-α2-6 sialylated glycan co-crystal structures. FIG. 11C shows difference between solvent accessible surface area (SASA) of Neu5Ac α2-3 and α2-6 sialylated oligosaccharides in the respective HA-glycan co-crystal structures. The bars respectively indicate that Neu5Ac in α2-6 (positive value) or α2-3 (negative value) sialylated glycans makes more contact with glycan binding site. FIG. 11D shows difference between SASA of NeuAc in α2-3 sialylated glycans bound to swine and human H1 ($H1_{\alpha2\text{-}3}$), avian and human H3 ($H3_{\alpha2\text{-}3}$), and of NeuAc in α2-6 sialylated glycans bound to swine and human H1 ($H1_{\alpha2\text{-}6}$). The negative bar for $H3_{\alpha2\text{-}3}$ indicates lesser contact of the human H3 HA with Neu5Acα2-3Gal compared to that of avian H3. Torsion angles—ϕ: C2-C1-O-C3 (for Neu5Acα2-3/6 linkage); ψ: C1-O-C3-H3 (for Neu5Acα2-3Gal) or C1-O-C6-C5 (for Neu5Acα2-6Gal); ω: O-C6-C5-H5 (for Neu5Acα2-6Gal) linkages.

The ϕ, ψ maps were obtained from GlycoMaps DB (available through the world wide web at glycosciences.de/modeling/glycomapsdb/) which was developed by Dr. Martin Frank and Dr. Claus-Wilhelm von der Lieth (German Cancer Research Institute, Heidelberg, Germany). The coloring scheme from high energy to low energy is from darker to lighter, respectively.

Figures 1, 4A:
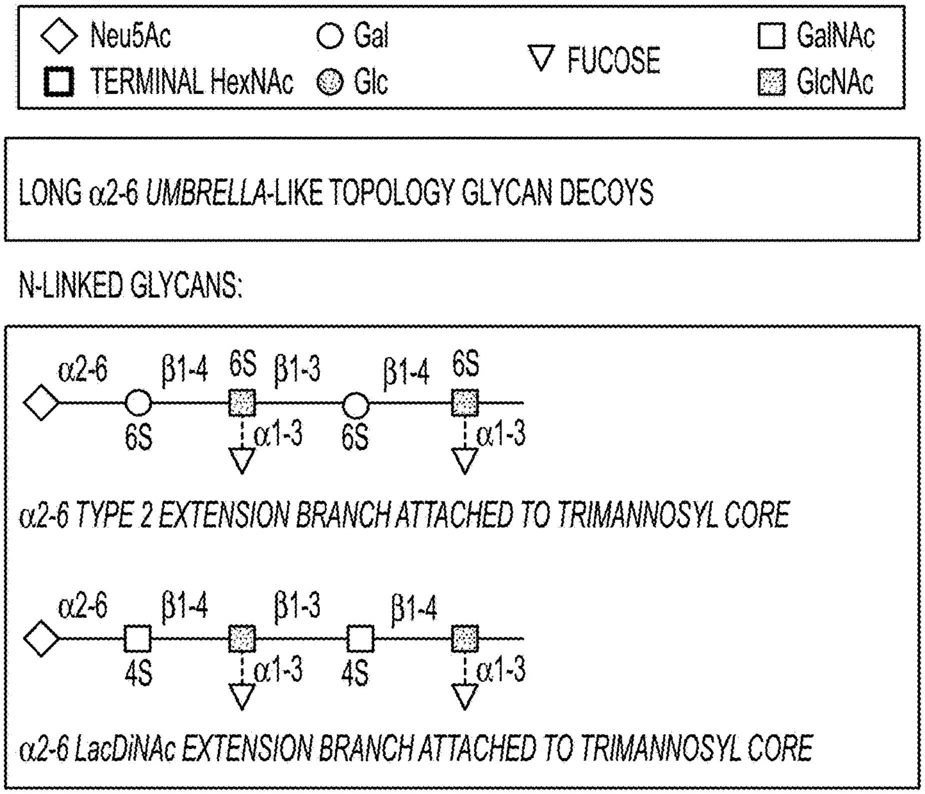
FIGS. 4A-B show exemplary umbrella topologies.
Figures 2, 4A:
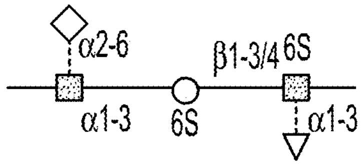
Figures 3, 4A:
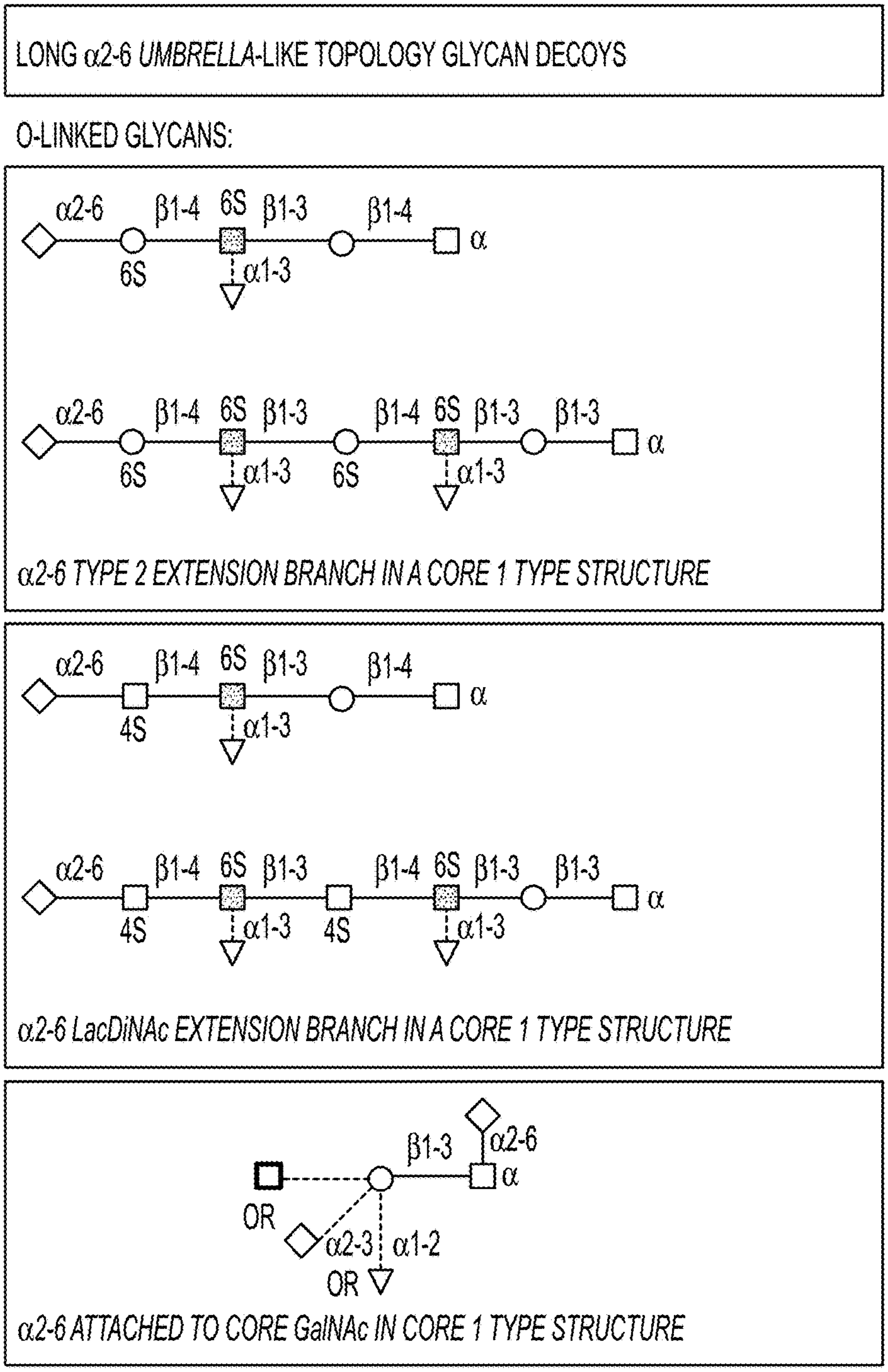
Figure 12A:
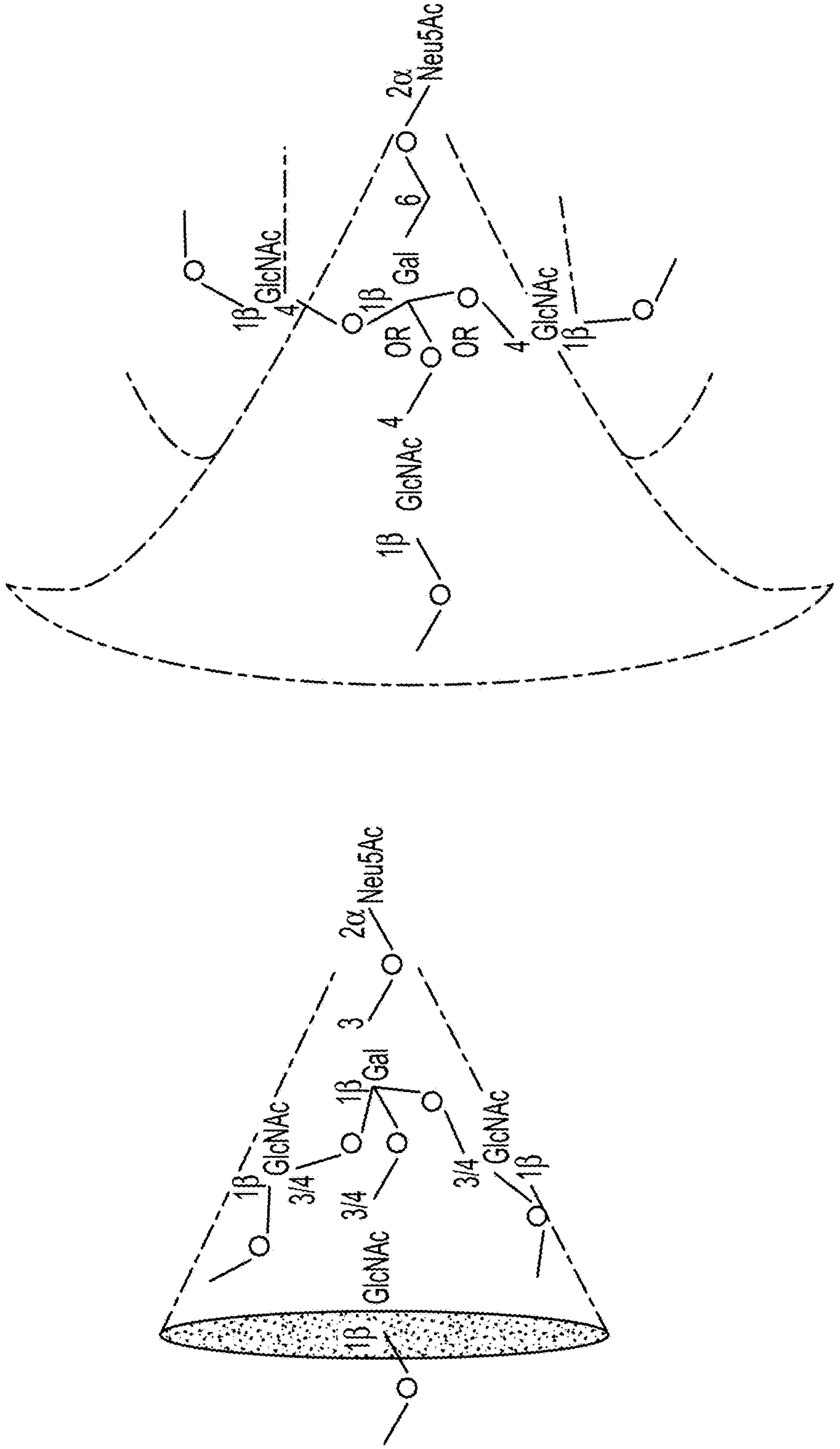
Figures 1, 12B:
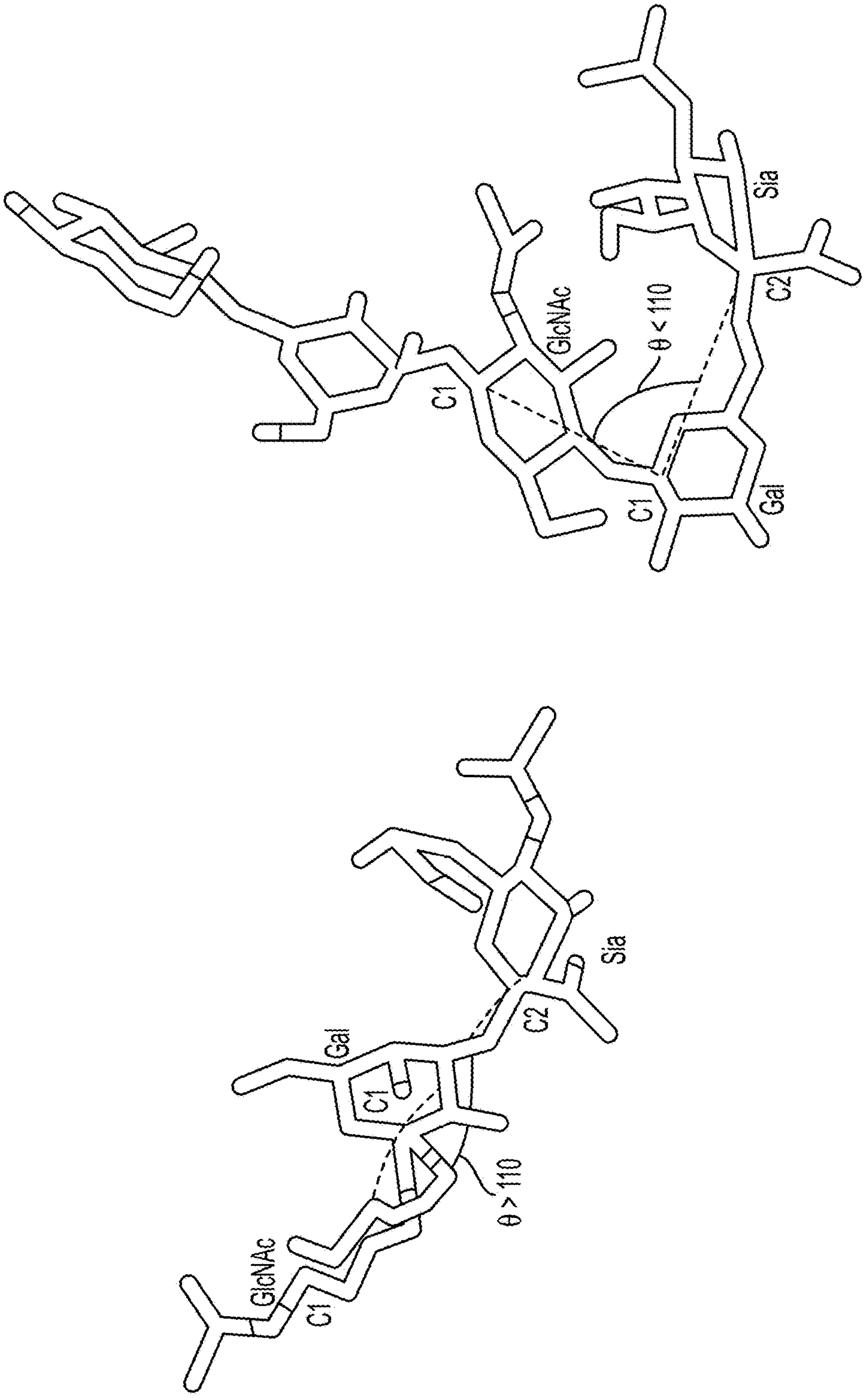
FIGS. 1A-E show alignments of exemplary sequences of wild type H2HA. Sequences were obtained from the NCBI influenza virus sequence database (available through the world wide web at ncbi.nlm.nih.gov/genomes/FLU/FLU).

FIGS. 12A-C show a framework for understanding glycan receptor specificity. α2-3- and/or α2-6-linked glycans can adopt different topologies. In some embodiments, the ability of an HA polypeptide to bind to certain of these topologies confers upon it the ability to mediate infection of different hosts, for example, humans. FIG. 12A illustrates two particularly relevant topologies, a "cone" topology and an "umbrella" topology. The cone topology can be adopted by α2-3- and/or α2-6-linked glycans, and is typical of short oligosaccharides or branched oligosaccharides attached to a core (although this topology can be adopted by certain long oligosaccharides). The umbrella topology can only be adopted by α2-6-linked glycans (presumably due to the increased conformational plurality afforded by the extra C5-C6 bond that is present in the α2-6 linkage), and is predominantly adopted by long oligosaccharides or branched glycans with long oligosaccharide branches, particularly containing the motif Neu5Acα2-6Galβ1-3/4GlcNAc-. As described herein, ability of HA polypeptides to bind the umbrella glycan topology, confers binding to human receptors and/or ability to mediate infection of humans. FIGS. 12B-1 and 12B-2 specifically show the topology of α2-3 and α2-6 as governed by the glycosidic torsion angles of the trisaccharide motifs Neu5Acα2-3Galβ1-3/4GlcNAc and Neu5Acα2-6Galβ1-4GlcNAc respectively. A parameter (θ)—angle between C2 atom of Neu5Ac and C1 atoms of the subsequent Gal and GlcNAc sugars in these trisaccharide motifs was defined to characterize the topology. Superimposition of the θ contour and the conformational maps of the α2-3 and α2-6 motifs shows that α2-3 motifs adopt 100% cone-like topology and α2-6 motifs sampled both cone-like and umbrella-like topologies (FIG. 12C). In the cone-like topology sampled by α2-3 and α2-6, GlcNAc and subsequent sugars are positioned along a region spanning a cone. Interactions of HA with cone-like topology primarily involve contacts of amino acids at the numbered positions (based on H3 HA numbering) with Neu5Ac and Gal sugars. On the other hand, in umbrella-like topology, which is unique to α2-6, \GlcNAc and subsequent sugars bend towards the HA binding site (as observed in HA-α2-6 co-crystal structures). Longer α2-6 oligosaccharides (e.g. at least a tetrasaccharide) would favor this conformation since it is stabilized by intra-sugar van der Waals contact between acetyl groups of GlcNAc and Neu5Ac. HA interactions with umbrella-like topology involve contacts of amino acids at the numbered positions (based on H3 HA numbering) with GlcNAc and subsequent sugars in addition to contacts with Neu5Ac and Gal sugars. FIG. 12C(A-F) depicts conformational sampling of cone- and umbrella-like topology by α2-3 and α2-6. FIG. 12C-A show the conformational (ϕ, ψ) map of Neu5Acα2-3Gal linkages. FIG. 12C-B shows the conformational (ϕ, ψ) map of Neu5Acα2-6Gal. FIG. 12C-C shows the conformational (ϕ, ψ) map of Galβ1-3GlcNAc linkages. FIG. 12C-D shows the conformational (ϕ, ψ) map of and Galβ1-4GlcNAc linkages. These maps obtained from GlycoMaps DB (available through the world wide web at glycosciences.de/modeling/glycomapsdb/) were generated using ab initio MD simulations using MM3 force field. Energy distribution is color coded starting from darker (representing higher energy) to lighter representing lower energy. Encircled regions 1-5 represent (ϕ, ψ) values observed for the α2-3 and α2-6 oligosaccharides in the HA-glycan co-crystal structures. The trans conformation (encircled region 1) of Neu5Acα2-3Gal predominates in HA binding pocket with the exception of the co-crystal structure of A/Aichi/2/68 H3N2 HA with α2-3 where this conformation is gauche (encircled region 2). On the other hand, the cis conformation of Neu5Acα2-6Gal (encircled region 3) predominates in HA binding pocket. The cone-like topology is sampled by encircled regions 1 and 2 and the umbrella-like topology is sampled by encircled region 3. FIG. 12C shows sampling of cone-like and umbrella-like topologies of α2-3 motif. FIG. 12C-F shows a sampling of cone-like and umbrella-like topologies of α2-6 motifs. The darker regions in the conformational maps were used as the outer boundaries to calculate the θ parameter (angle between C2 atom of Neu5Ac and C1 atoms of subsequent Gal and GlcNAc sugars) for a given set of (ϕ, ψ) values. Based on the energy cutoff, the value of θ>110° was used to characterize cone-like topology and θ<100° was used to characterize umbrella-like topology. Superimposition of the θ contour with the conformational energy map indicated that α2-3 motif adopts 100% cone-like topology since it was energetically unfavorable to adopt umbrella-like topology. On the other hand, the α2-6 motif sampled both the cone-like and umbrella-like topologies and this sampling was classified based on the ω angle (O-C6-C5-H5) of Neu5Acα2-6Gal linkage.

Figure 13:
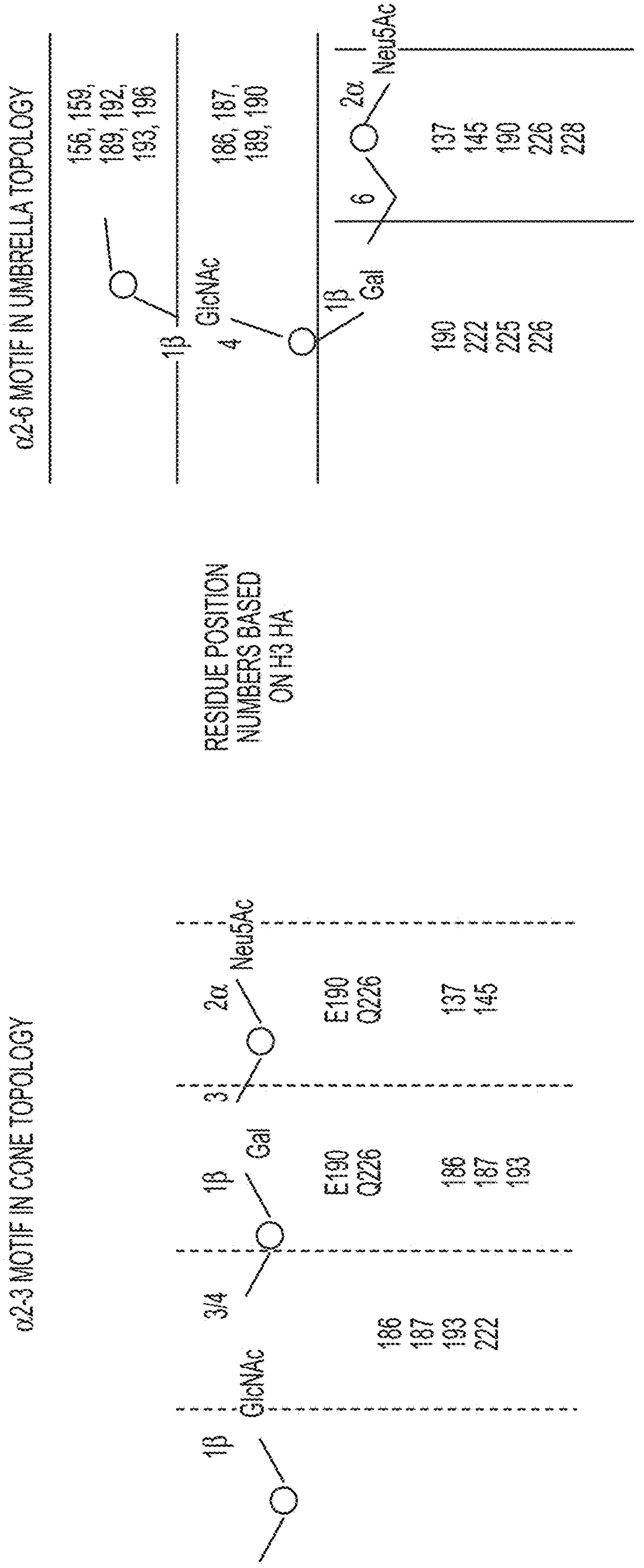

FIG. 13 shows interactions of HA residues with cone vs umbrella glycan topologies. Analysis of HA-glycan co-crystals reveals that the position of Neu5Ac relative to the HA binding site is almost invariant. Contacts with Neu5Ac involve highly conserved residues such as F98, S/T136, W153, H183 and L/I194. Contacts with other sugars involve different residues, depending on whether the sugar linkage is α2-3 or α2-6 and whether the glycan topology is cone or umbrella. For example, in the cone topology, the primary contacts are with Neu5Ac and with Gal sugars. E190 and Q226 play particularly important roles in this binding. This Figure also illustrates other positions (e.g., 137, 145, 186, 187, 193, 222) that can participate in binding to cone structures. In some cases, different residues can make different contacts with different glycan structures. The type of amino acid in these positions can influence ability of an HA polypeptide to bind to receptors with different modification and/or branching patterns in the glycan structures. In the umbrella topology, contacts are made with sugars beyond Neu5Ac and Gal. This Figure illustrates residues (e.g., 137, 145, 156, 159, 186, 187, 189, 190, 192, 193, 196, 222, 225, 226) that can participate in binding to umbrella structures. In some cases, different residues can make different contacts with different glycan structures. The type of amino acid in these positions can influence ability of an HA polypeptide to bind to receptors with different modification and/or branching patterns in the glycan structures. In some embodiments, a D residue at position 190 and/or a D residue at position 225 contribute(s) to binding to umbrella topologies.

Figure 14A:
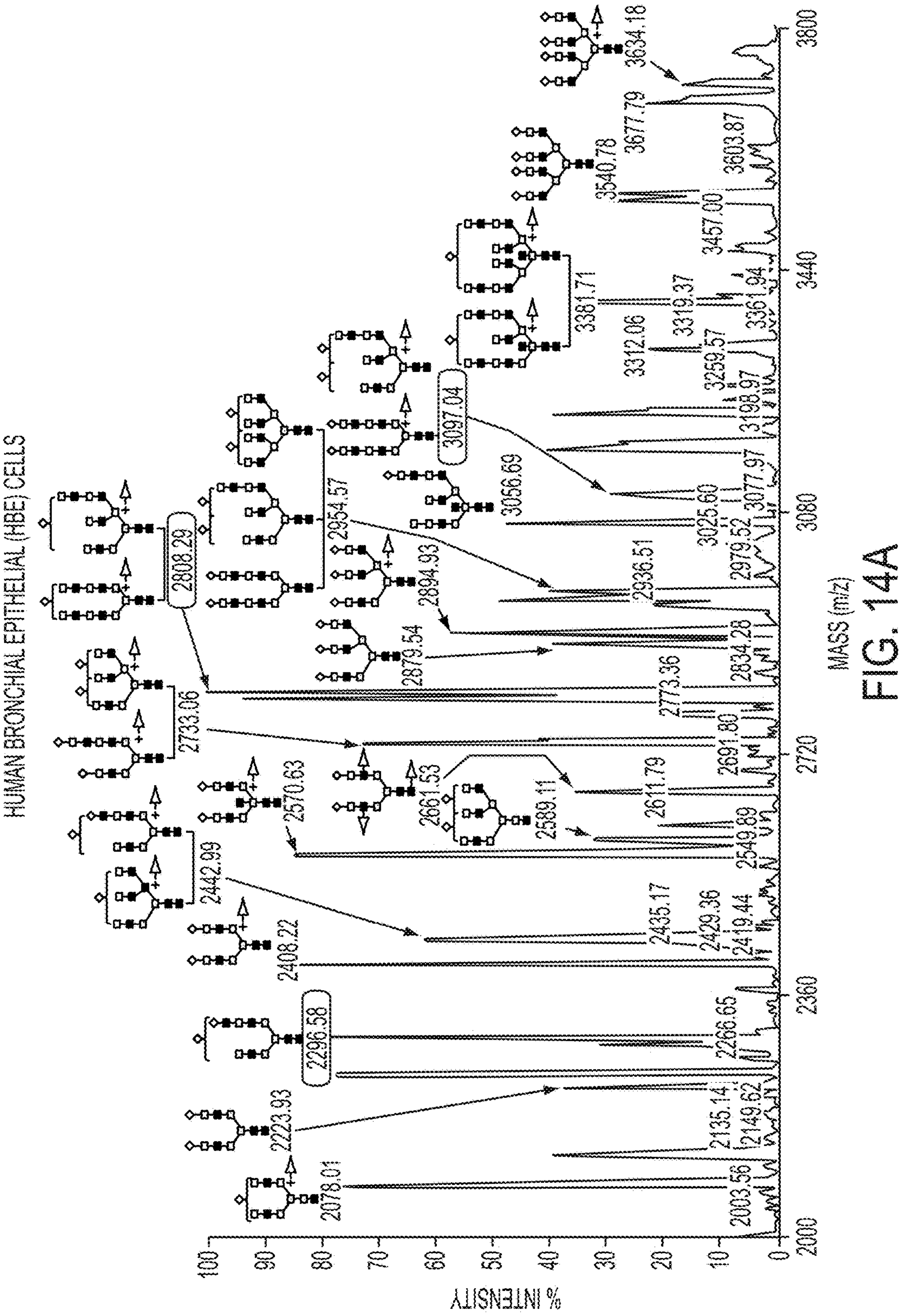
Figure 14B:
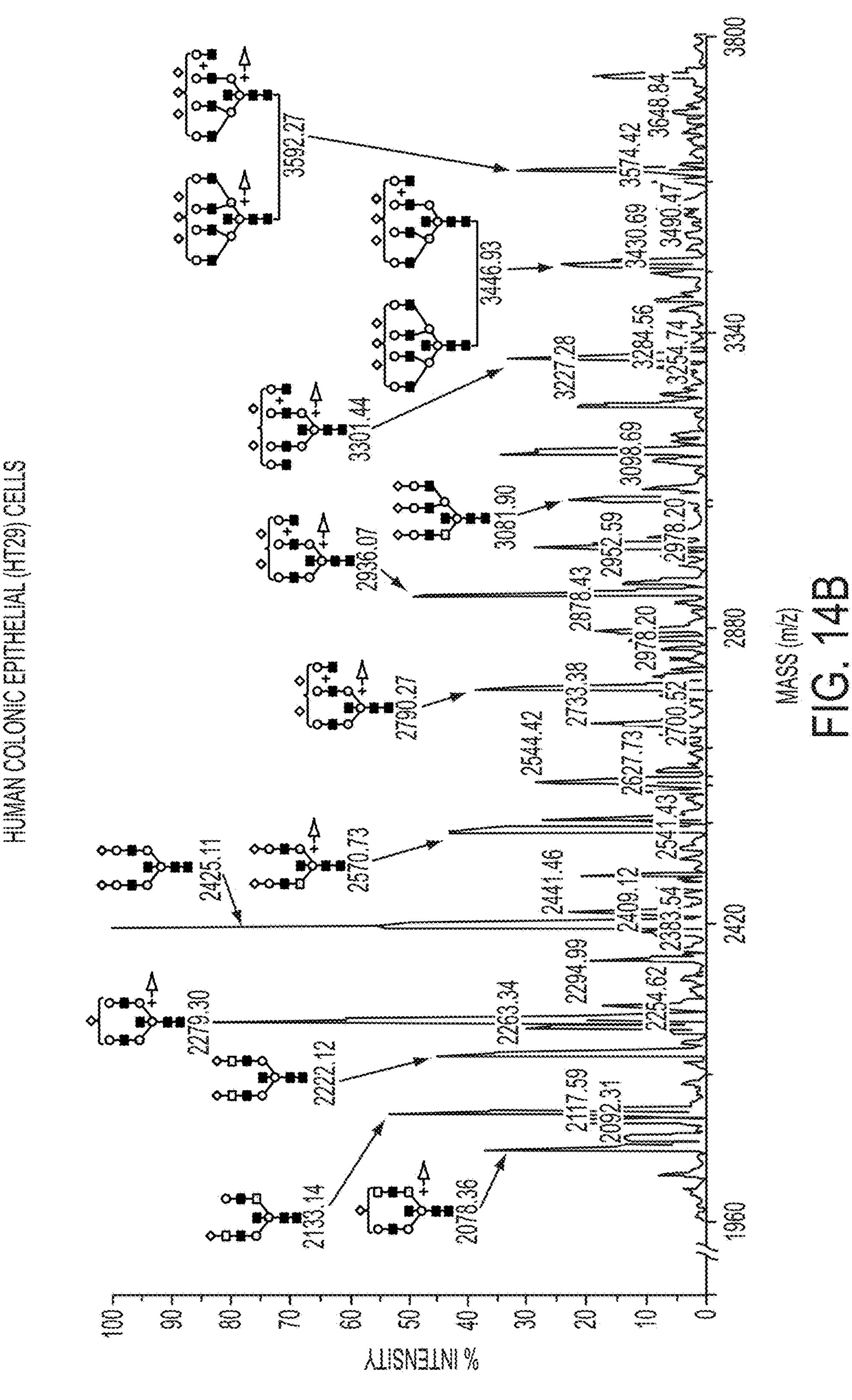

FIGS. 14A-B show a glycan profile in human epithelial cells. FIG. 14A shows the glycan profile of human bronchial epithelial cells. FIG. 14B shows the glycan profile of human colonic epithelial cells. To further investigate the glycan diversity in the upper respiratory tissues, N-linked glycans were isolated from HBEs (a representative upper respiratory cell line) and analyzed using MALDI-MS. The predominant expression of a2-6 in HBEs was confirmed by pre-treating the sample with Sialidase S (a2-3 specific) and Sialidase A (cleaves and SA). The predominant expression of glycans with long branch topology is supported by TOF-TOF fragmentation analysis of representative mass peaks. To provide a reference for glycan diversity in the upper respiratory tissues, the N-linked glycan profile of human colonic epithelial cells (HT29; a representative gut cell line) was obtained. This cell line was chosen because the current H5N1 viruses have been shown to infect gut cells. Sialidase A and S pre-treatment controls showed predominant expression of a2-3 glycans in the HT-29 cells. Moreover, the long branch glycan topology is not as prevalent as observed for HBEs. Therefore, human adaptation of the H5N1 HA would involve HA mutations that would enable high affinity binding to the diverse glycans expressed in the human upper respiratory tissues (e.g., umbrella glycans).

Figure 15A:
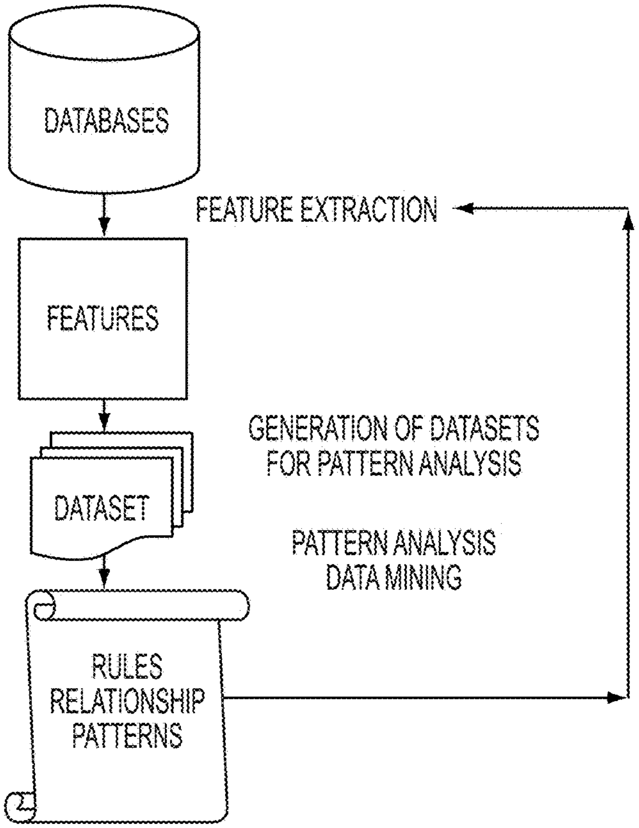
Figure 15B:
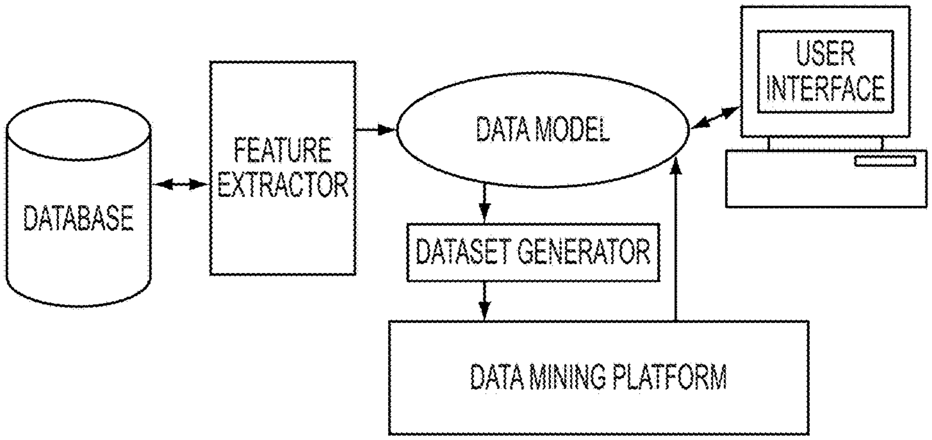

FIGS. 15A-B. Data mining platform. FIG. 15A illustrates the main components of the data mining platform. The features are derived from the data objects which are extracted from the database. The features are prepared into datasets that are used by the classification methods to derive patterns or rules. FIG. 15B shows the key software modules that enable the user to apply the data mining process to the glycan array data.

Figure 16:
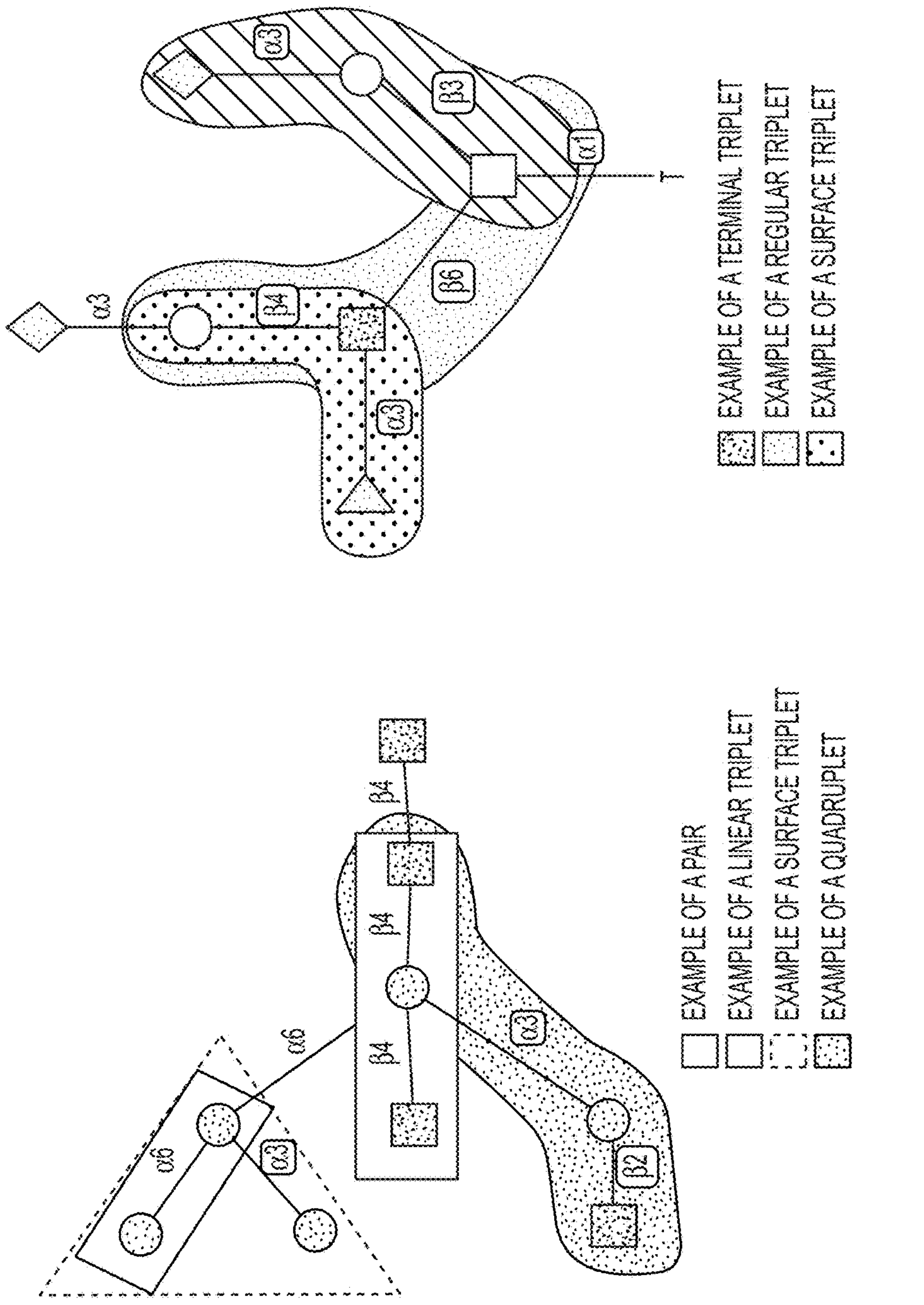

FIG. 16. Features used in data mining analysis. This figure shows the features defined herein as representative motifs that illustrate the different types of pairs, triplets and quadruplets abstracted from the glycans on the glycan microarray. The rationale behind choosing these features is based on the binding of di-tetra saccharides to the glycan binding site of HA. The final dataset comprise features from the glycans as well as the binding signals for each of the HAs screened on the array. Among the different methods for classification, the rule induction classification method was utilized. One of the main advantages of this method is that it generates IF-THEN rules which can be interpreted more easily when compared to the other statistical or mathematical methods. The two main objectives of the classification were: (1) identifying features present on a set of high affinity glycan ligands, which enhance binding, and (2) identifying features that are in the low affinity glycan ligands that are not favorable for binding.

Figure 17A:
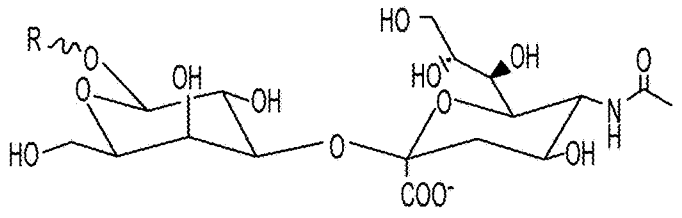
Figure 17A:
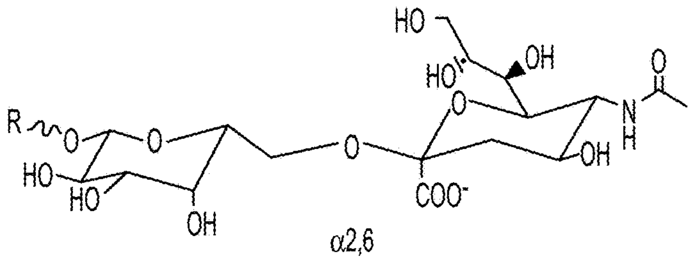
Figure 17B:
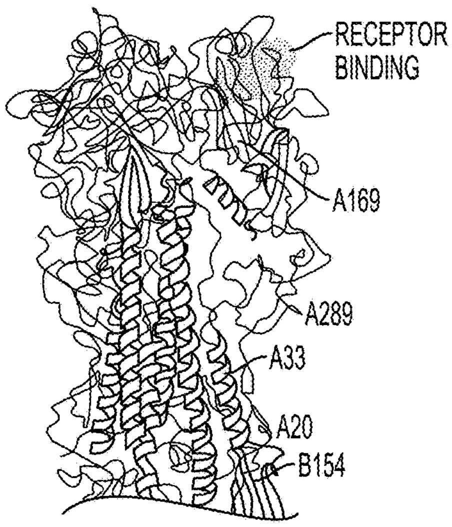
Figure 17C:
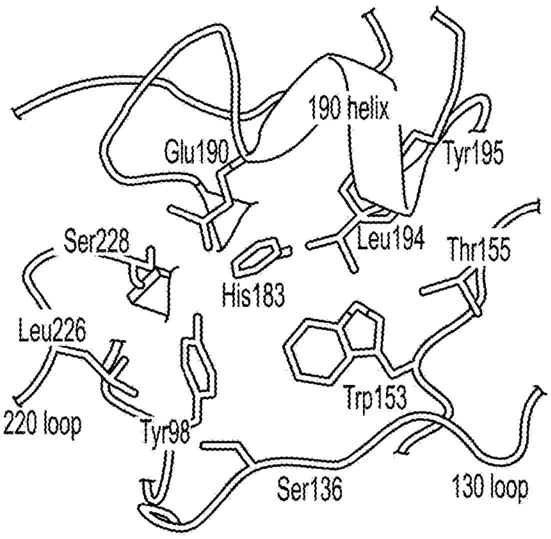

FIGS. 17A-C. Crystal Structure of Exemplary H2 HA. FIG. 17A shows the chemical structures of α2,3- and α2,6-linked glycans, with the terminal sialic acid and galactose shown here. FIG. 17B illustrates the overview of the 1957 H2 trimer. Five potential glycosylation sites are found on each monomer (as labeled). Glycans in the density map are shown. FIG. 17C shows the receptor binding site of H2. Residues involved in receptor binding, as suggested by the H3 structures, are shown in sticks. Aromatic residues comprising the base of the binding site are absolutely conserved in various HA subtypes. Residues from the 220 loop and position 190 are critical for the receptor specificity switch in H1, H2, and H3. (Xu R et al., *J Virol* 84(4):1715-1721, 2010).

Figure 18A:
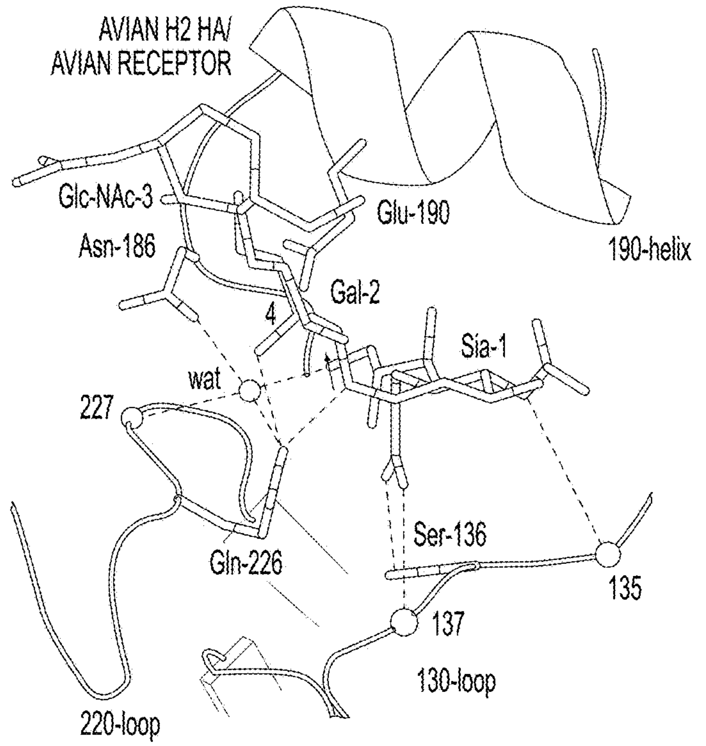
Figure 18B:
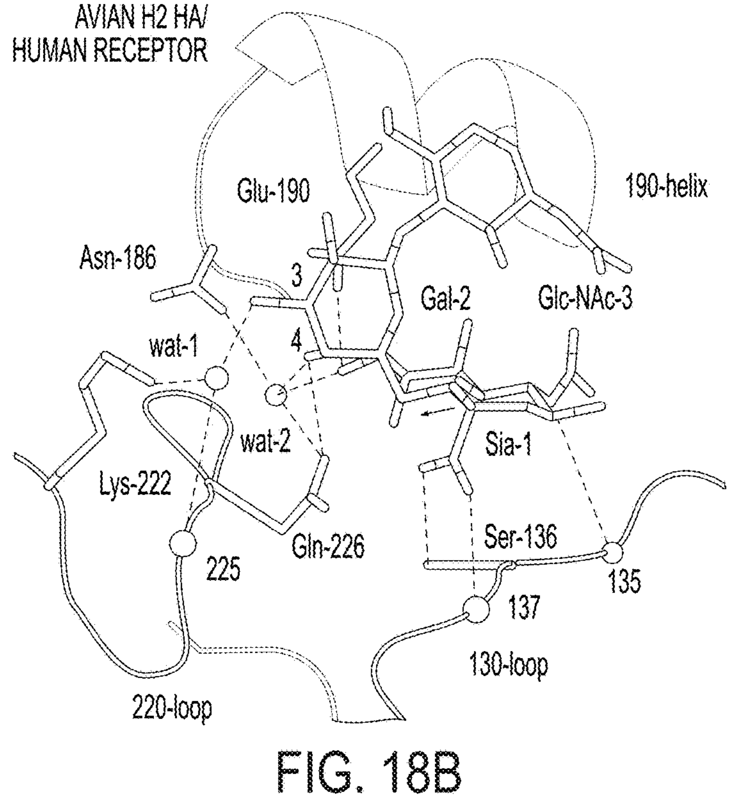
Figure 18C:
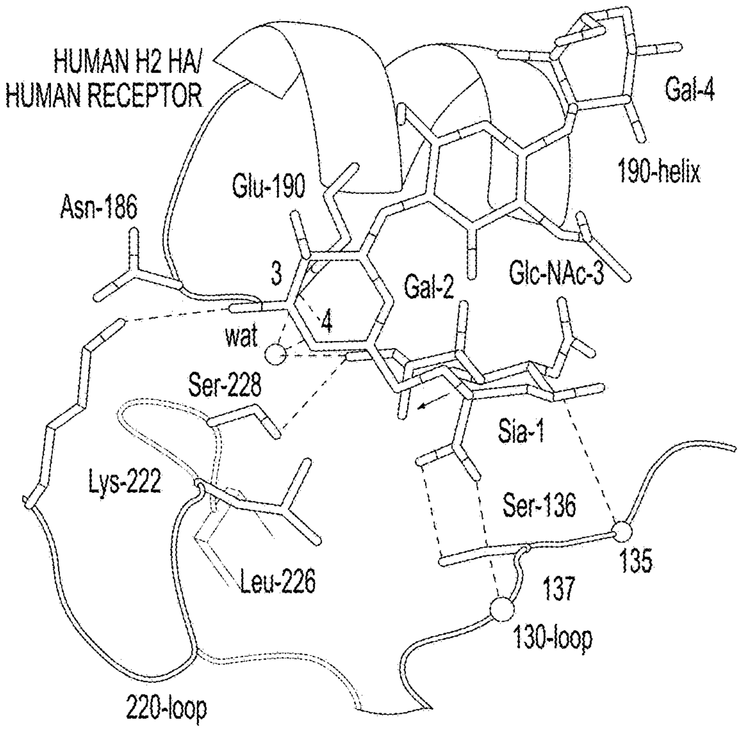
Figure 18D:
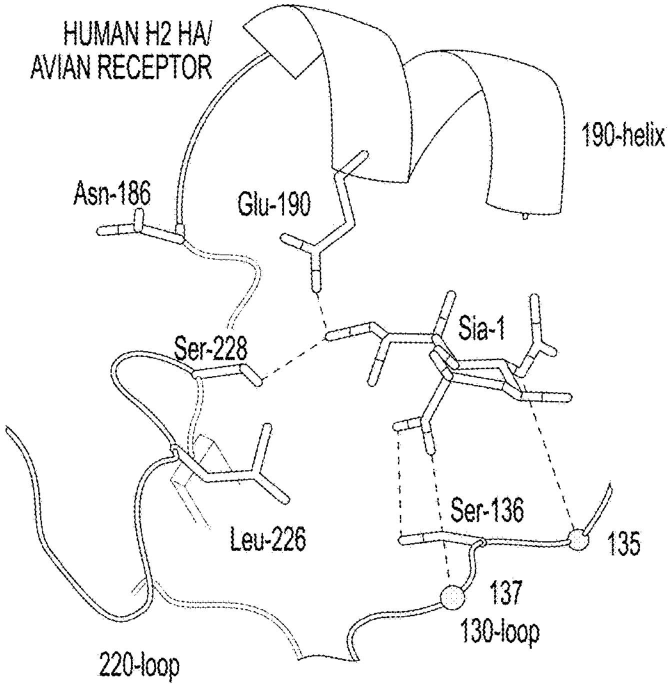

FIGS. 18A-D. Interactions of avian H2 HA and human H2 HA with avian and human receptor analogs. Interactions of an avian H2 HA (upper panels) and a human H2 HA (lower panels) with avian and human receptor analogues. The three secondary structure elements of the binding site, the 130- and 220-loops and the 190-helix are labeled in this backbone representation together with some selected side chains in stick representation. The broken lines indicate potential hydrogen bond interaction. In all four panels, the carbon, nitrogen, and oxygen atoms in the sialosaccharides are depicted, and water molecules are labeled. A/dk/Ontario/77 H2 HA in complex with avian receptor, LSTa (FIG. 18A) and human receptor, LSTc (FIG. 18B). A/Singapore/1/57 H2 HA in complex with human receptor (FIG. 18C) and avian receptor (FIG. 18D). The black arrows in FIGS. 18A, 18B, and 18C indicate that for the two human receptor complexes the Sia-1/Gal-2 linkage adopts a cis conformation, whereas for the avian complex it adopts a trans conformation (Liu J, et al. 2009 Proc Natl Acad Sci USA 106(40):17175-17180; incorporated herein by reference).

DESCRIPTION OF HA SEQUENCE ELEMENTS

HA Sequence Element 1

HA Sequence Element 1 is a sequence element corresponding approximately to residues 97-185 (where residue positions are assigned using H3 HA as reference) of many HA proteins found in natural influenza isolates. This sequence element has the basic structure:

(SEQ ID NO. 21)

C (Y/F) P $X_1$ C $X_2$ W $X_3$ W $X_4$ H H P, wherein:

$X_1$ is approximately 30-45 amino acids long;

$X_2$ is approximately 5-20 amino acids long;

$X_3$ is approximately 25-30 amino acids long; and $X_4$ is approximately 2 amino acids long.

In some embodiments, $X_1$ is about 35-45, or about 35-43, or about 35, 36, 37, 38, 38, 40, 41, 42, or 43 amino acids long. In some embodiments, $X_2$ is about 9-15, or about 9-14, or about 9, 10, 11, 12, 13, or 14 amino acids long. In some embodiments, $X_3$ is about 26-28, or about 26, 27, or 28 amino acids long. In some embodiments, $X_4$ has the sequence (G/A) (I/V). In some embodiments, $X_4$ has the sequence GI; in some embodiments, $X_4$ has the sequence GV; in some embodiments, $X_4$ has the sequence AI; in some embodiments, $X_4$ has the sequence AV. In some embodiments, HA Sequence Element 1 comprises a disulfide bond. In some embodiments, this disulfide bond bridges residues corresponding to positions 97 and 139 (based on the canonical H3 numbering system utilized herein).

HA Sequence Element 2

HA Sequence Element 2 is a sequence element corresponding approximately to residues 324-340 (again using a numbering system based on H3 HA) of many HA proteins found in natural influenza isolates. This sequence element has the basic structure:

(SEQ ID NO. 22)

G A I A G F I E

In some embodiments, HA Sequence Element 2 has the sequence:

(SEQ ID NO. 23)

P $X_1$ G A I A G F I E, wherein:

$X_1$ is approximately 4-14 amino acids long, or about 8-12 amino acids long, or about 12, 11, 10, 9 or 8 amino acids long. In some embodiments, this sequence element provides the HA0 cleavage site, allowing production of HA1 and HA2.

Definitions

Affinity: As is known in the art, "affinity" is a measure of the tightness with a particular ligand (e.g., an HA polypeptide) binds to its partner (e.g., an HA receptor). Affinities can be measured in different ways. In some embodiments, affinity is measured by a quantitative assay (e.g., glycan binding assays). In some such embodiments, binding partner concentration (e.g., HA receptor, glycan, etc.) may be fixed to be in excess of ligand (e.g., an HA polypeptide) concentration so as to mimic physiological conditions (e.g., viral HA binding to cell surface glycans). Alternatively or additionally, in some embodiments, binding partner (e.g., HA receptor, glycan, etc.) concentration and/or ligand (e.g., an HA polypeptide) concentration may be varied. In some such embodiments, affinity (e.g., binding affinity) may be compared to a reference (e.g., a wild type HA that mediates infection of a humans) under comparable conditions (e.g., concentrations).

Binding: It will be understood that the term "binding", as used herein, typically refers to a non-covalent association between or among agents. In many embodiments herein, binding is addressed with respect to particular glycans (e.g., umbrella topology glycans or cone topology glycans). It will be appreciated by those of ordinary skill in the art that such binding may be assessed in any of a variety of contexts. In some embodiments, binding is assessed with respect to free glycans. In some embodiments, binding is assessed with respect to glycans attached (e.g., covalently linked to) a carrier. In some such embodiments, the carrier is a polypeptide. In some embodiments, binding is assessed with respect to glycans attached to an HA receptor. In such embodiments, reference may be made to receptor binding or to glycan binding.

Binding agent: In general, the term "binding agent" is used herein to refer to any entity that binds to glycans (e.g., to umbrella-topology glycans) as described herein. Binding agents may be of any chemical type. In some embodiments, binding agents are polypeptides (including, e.g., antibodies or antibody fragments); in some such embodiments, binding agents are HA polypeptides; in other embodiments, binding agents are polypeptides whose amino acid sequence does not include an HA characteristic sequence (i.e., "Non-HA polypeptides). In some embodiments, binding agents are small molecules. In some embodiments, binding agents are nucleic acids. In some embodiments, binding agents are aptamers. In some embodiments, binding agents are polymers; in some embodiments, binding agents are non-polymeric. In some embodiments, binding agents are carbohydrates. In some embodiments, binding agents are lectins. In some embodiments, binding agents as described herein bind to sialylated glycans having an umbrella-like topology. In some embodiments, binding agents bind to umbrella-topology glycans with high affinity and/or specificity. In some embodiments, binding agents show a binding preference for umbrella-topology glycans as compared with cone-topology glycans. In some embodiments, binding agents compete with hemagglutinin for binding to glycans on hemagglutinin receptors. In some embodiments, binding agents compete with hemagglutinin for binding to umbrella-topology glycans. In some embodiments, a binding agent provided herein is an umbrella topology blocking agent. In some embodiments, a binding agent provided herein is an umbrella topology specific blocking agent. In some embodiments, binding agents bind to umbrella topology glycan mimics.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, at least 10, at least 15, at least 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids and/or that includes an immunogenic epitope, and therefore can be used by those of ordinary skill in the art to define members of the family.

Figure 3:
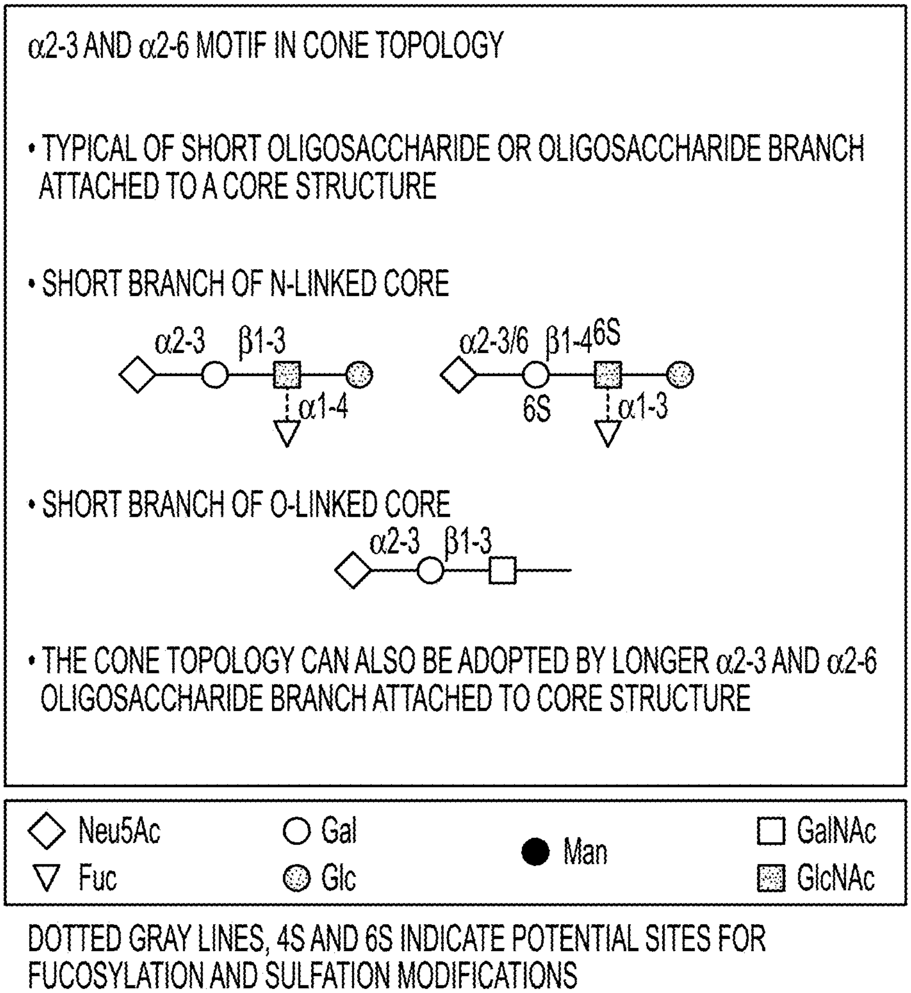
FIG. 3 shows exemplary cone topologies. This Figure illustrates certain exemplary (but not exhaustive) glycan structures that adopt cone topologies.

Cone topology: The phrase "cone topology" is used herein to refer to a 3-dimensional arrangement adopted by certain glycans and in particular by glycans on HA receptors. As illustrated in FIG. 3, the cone topology can be adopted by α2-3 sialylated glycans or by α2-6 sialylated glycans, and is typical of short oligonucleotide chains, though some long oligonucleotides can also adopt this conformation. The cone topology is characterized by the glycosidic torsion angles of Neu5Acα2-3Gal linkage which samples three regions of minimum energy conformations given by $\phi$ (C1-C2-O-C3/C6) value of about −60, about 60 or about 180 and $\psi$ (C2-O-C3/C6-H3/C5) samples −60 to 60 (FIG. 11). FIG. 3 presents certain representative (though not exhaustive) examples of glycans that adopt a cone topology.

Corresponding to: As used herein, the term "corresponding to" is often used to designate the position/identity of an amino acid residue in an HA polypeptide. Those of ordinary skill will appreciate that, for purposes of simplicity, a canonical numbering system (based on wild type H3 HA) is utilized herein (as illustrated, for example, in FIGS. 1-2), so that an amino acid "corresponding to" a residue at position 190, for example, need not actually be the $190^{th}$ amino acid in a particular amino acid chain but rather corresponds to the residue found at 190 in wild type H3 HA; those of ordinary skill in the art readily appreciate how to identify corresponding amino acids.

Degree of separation removed: As used herein, amino acids that are a "degree of separation removed" are HA amino acids that have indirect effects on glycan binding. For example, one-degree-of-separation-removed amino acids may either: (1) interact with the direct-binding amino acids; and/or (2) otherwise affect the ability of direct-binding amino acids to interact with glycan that is associated with host cell HA receptors; such one-degree-of-separation-removed amino acids may or may not directly bind to glycan themselves. Two-degree-of-separation-removed amino acids either (1) interact with one-degree-of-separation-removed amino acids; and/or (2) otherwise affect the ability of the one-degree-of-separation-removed amino acids to interact with direct-binding amino acids, etc.

Direct-binding amino acids: As used herein, the phrase "direct-binding amino acids" refers to HA polypeptide amino acids which interact directly with one or more glycans that is associated with host cell HA receptors.

Engineered: The term "engineered", as used herein, describes a polypeptide whose amino acid sequence has been selected by man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

H2 polypeptide: An "H2 polypeptide", as that term is used herein, is an HA polypeptide whose amino acid sequence includes at least one sequence element that is characteristic of H2 and distinguishes H2 from other HA subtypes. Representative such sequence elements can be determined by alignments such as, for example, those illustrated in FIG. 1 and include, for example, those described herein with regard to H2-specific embodiments of HA Sequence Elements.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (available through the world wide web at ncbi.nlm.nih.gov/genomes/FLU/flu) that, as of the filing of the present application included 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus. In some embodiments, an HA polypeptide has an amino acid sequence comprising at least one of HA Sequence Elements 1 and 2, as defined herein. In some embodiments, an HA polypeptide has an amino acid sequence comprising HA Sequence Elements 1 and 2, in some embodiments separated from one another by about 100 to about 200, or by about 125 to about 175, or about 125 to about 160, or about 125 to about 150, or about 129 to about 139, or about 129, about 130, about 131, about 132, about 133, about 134, about 135, about 136, about 137, about 138, or about 139 amino acids. In some embodiments, an HA polypeptide has an amino acid sequence that includes residues at positions within the regions 96-100 and/or 130-230 that participate in glycan binding. For example, many HA polypeptides include one or more of the following residues: Tyr98, Ser/Thr136, Trp153, His183, and Leu/Ile194. In some embodiments, an HA polypeptide includes at least 2, 3, 4, or all 5 of these residues.

High affinity binding: The term "high affinity binding", as used herein refers to a high degree of tightness with which a particular ligand (e.g., an HA polypeptide) binds to its partner (e.g., an HA receptor). Affinities can be measured by any available method, including those known in the art. In some embodiments, binding is considered to be high affinity if the Kd' is about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays. In some embodiments, binding is considered to be high affinity if the affinity is stronger (e.g., the Kd' is lower) for a polypeptide of interest than for a selected reference polypeptide. In some embodiments, binding is considered to be high affinity if the ratio of the Kd' for a polypeptide of interest to the Kd' for a selected reference polypeptide is 1:1 or less (e.g., 0.9:1, 0.8:1, 0.7:1, 0.6:1, 0.5:1, 0.4:1, 0.3:1, 0.2:1, 0.1:1, 0.05:1, 0.01:1, or less). In some embodiments, binding is considered to be high affinity if the Kd' for a polypeptide of interest is about 100% or less (e.g., about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1% or less) of the Kd' for a selected reference polypeptide.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Linkage Specific Blocking Agent (LSBA): As used herein, the term "linkage specific blocking agent" refers to an agent which binds to an HA receptor having an α2-6 sialylated glycan. In some embodiments, an LSBA selectively binds to an HA receptor having an α2-6 sialylated glycan with at least about 40, 50, or 75% of the affinity of that for an HA receptor having an α2-3 sialylated glycan. In some embodiments, an LSBA selectively binds to an HA receptor having an α2-6 sialylated glycan with at least about 2, 4, 5, or 10 times greater affinity than that for an HA receptor having an α2-3 sialylated glycan. In some embodiments, an LSBA has an affinity for an α2-6 sialylated glycan that is at least 50, 100, 150, or 200% of its affinity for an α2-3 sialylated glycan. In some embodiments, an LSBA may compete with hemagglutinin for binding to an HA receptor. For example, an LSBA may selectively inhibit the binding of an influenza virus particle (e.g., human or avian influenza virus) to an HA receptor based on the linkage characteristics (e.g., α2-6 sialylated glycan or α2-3 sialylated glycan). In some embodiments, an LSBA is a polypeptide. In some such embodiments, an LSBA polypeptide has an amino acid sequence that is substantially identical or substantially homologous to that of a naturally-occurring polypeptide. In some embodiments, an LSBA polypeptide is an HA polypeptide. In some embodiments, an LSBA polypeptide is a naturally-occurring HA polypeptide, or a fragment thereof. In some embodiments, an LSBA polypeptide has an amino acid sequence that is not related to that of an HA polypeptide. In some embodiments, an LSBA polypeptide is an antibody or fragment thereof. In some embodiments, an LSBA polypeptide is a lectin (e.g., SNA-1). In some embodiments, an LSBA is not a polypeptide. In some embodiments, an LSBA is a small molecule. In some embodiments, an LSBA is a nucleic acid.

Long oligosaccharide: For purposes of the present disclosure, an oligosaccharide is typically considered to be "long" if it includes at least one linear chain that has at least four saccharide residues.

Low affinity binding: The term "low affinity binding", as used herein refers to a low degree of tightness with which a particular ligand (e.g., an HA polypeptide) binds to its partner (e.g., an HA receptor). As described herein, affinities can be measured by any available method, including methods known in the art. In some embodiments, binding is considered to be low affinity if the Kd' is about 100 pM or more (e.g., above about 200 pM, 300 pM, 400 pM, 500 pM, 600 pM, 700 pM, 800 pM, 900 pM, 1 nM, 1.1 nM, 1.2 nM, 1.3 nM, 1.4 nM, 1.5 nM, etc.) In some embodiments, binding is considered to be low affinity if the affinity is the same or lower (e.g., the Kd' is about the same or higher) for a polypeptide of interest than for a selected reference polypeptide. In some embodiments, binding is considered to be low affinity if the ratio of the Kd' for a polypeptide of interest to the Kd' for a selected reference polypeptide is 1:1 or more (e.g., 1.1:1, 1.2:1, 1.3:1, 1.4:1, 1.5:1, 1.6:1, 1.7:1, 1.8:1, 1.9:1, 2:1, 3:1, 4:1, 5:1, 10:1 or more). In some embodiments, binding is considered to be low affinity if the Kd' for a polypeptide of interest is 100% or more (e.g., 100%, 105%, 110%, 115%, 120%, 125%, 130%, 135%, 140%, 145%, 150%, 155%, 160%, 165%, 170%, 175%, 180%, 185%, 190%, 195%, 200%, 300%, 400%, 500%, 1000%, or more) of the Kd' for a selected reference polypeptide.

Non-natural amino acid: The phrase “non-natural amino acid” refers to an entity having the chemical structure of an amino acid (i.e.:

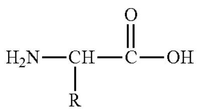

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Polypeptide: A “polypeptide”, generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include “non-natural” amino acids or other entities that nonetheless are capable of integrating into a polypeptide chain, optionally.

Predominantly Present: The term “predominantly present”, as used herein, refers to the presence of an entity (e.g., an amino acid residue) at a particular location across a population. For example, an amino acid may be predominantly present if, across a population of polypeptides, a particular amino acid is statistically present in at least about 50%, about 55%, about 60%, about 65%, about 70%, about 75%, about 80%, about 85%, about 90%, about 95%, about 96%, about 97%, about 98%, about 99% or more of the population of polypeptides.

Prevention: The term “prevention”, as used herein, refers to a delay of onset, and/or reduction in frequency and/or severity of one or more symptoms of a particular disease, disorder or condition (e.g., infection for example with influenza virus). In some embodiments, prevention is assessed on a population basis such that an agent is considered to “prevent” a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is “pure” if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Short oligosaccharide: For purposes of the present disclosure, an oligosaccharide is typically considered to be “short” if it has fewer than 4, or certainly fewer than 3, residues in any linear chain.

Specificity: As is known in the art, “specificity” is a measure of the ability of a particular ligand (e.g., an HA polypeptide) to distinguish its binding partner (e.g., a human HA receptor, and particularly a human upper respiratory tract HA receptor) from other potential binding partners (e.g., an avian HA receptor).

Substantial homology: The phrase “substantial homology” is used herein to refer to a comparison between amino acid or nucleic acid sequences. As will be appreciated by those of ordinary skill in the art, two sequences are generally considered to be “substantially homologous” if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as “hydrophobic” or “hydrophilic” amino acids, and/or as having “polar” or “non-polar” side chains Substitution of one amino acid for another of the same type may often be considered a “homologous” substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., “Gapped BLAST and PSI-BLAST: a new generation of protein database search programs”, *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying identical sequences, the programs mentioned above typically provide an indication of the degree of identity. In some embodiments, two sequences are considered to be substantially identical if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are identical over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Therapeutic agent: As used herein, the phrase "therapeutic agent" refers to any agent that elicits a desired biological or pharmacological effect.

Treatment: As used herein, the term "treatment" refers to any method used to alleviate, delay onset, reduce severity or incidence, or yield prophylaxis of one or more symptoms or aspects of a disease, disorder, or condition. For the purposes of the present invention, treatment can be administered before, during, and/or after the onset of symptoms.

Figures 4, 4A, 5:
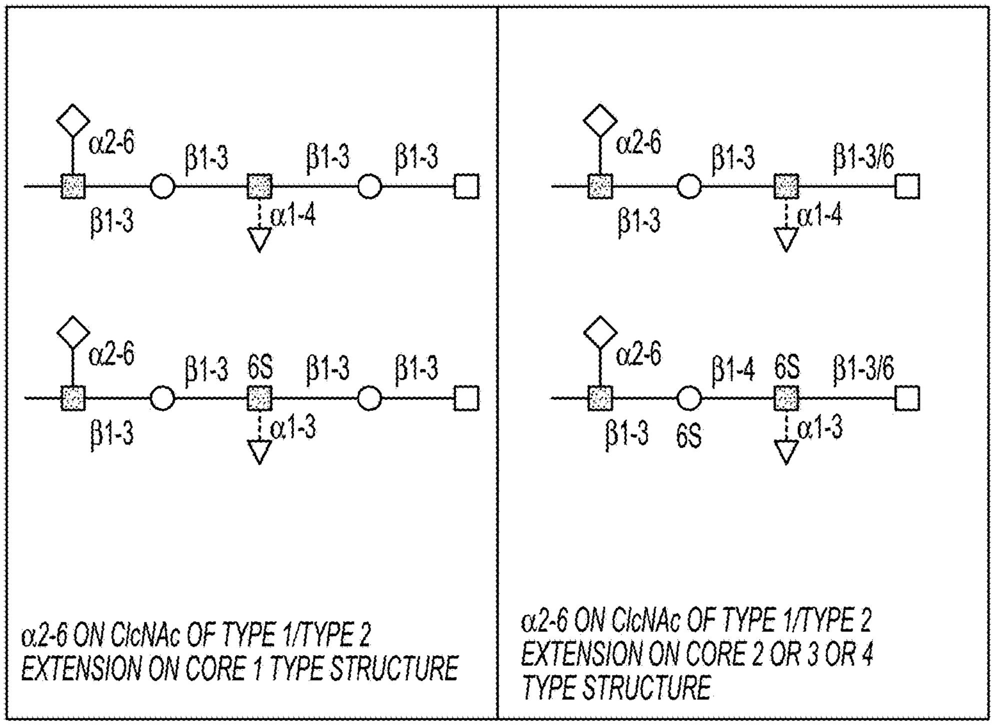
Figures 4, 4A, 5, 6:
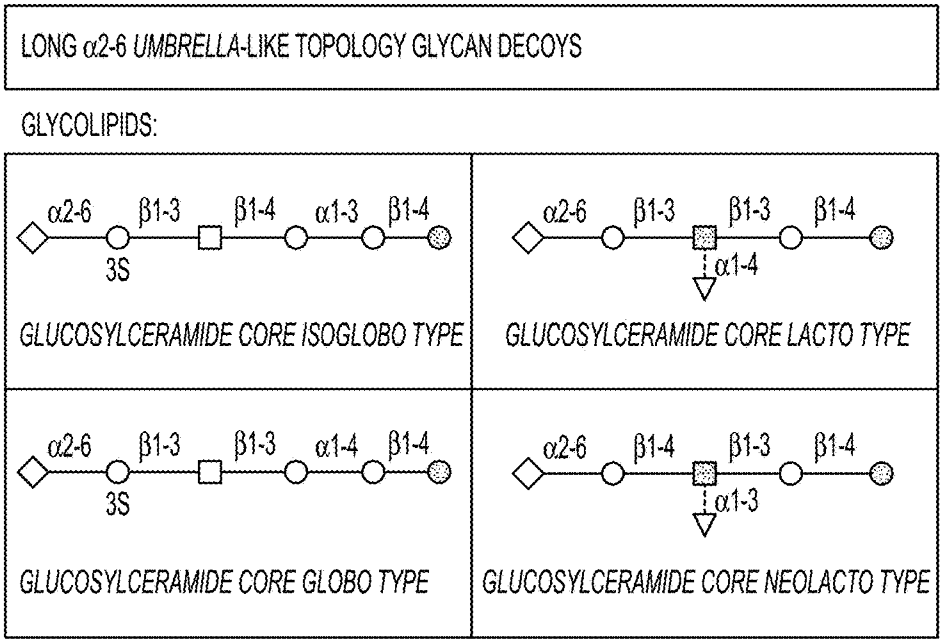
Figure 4B:
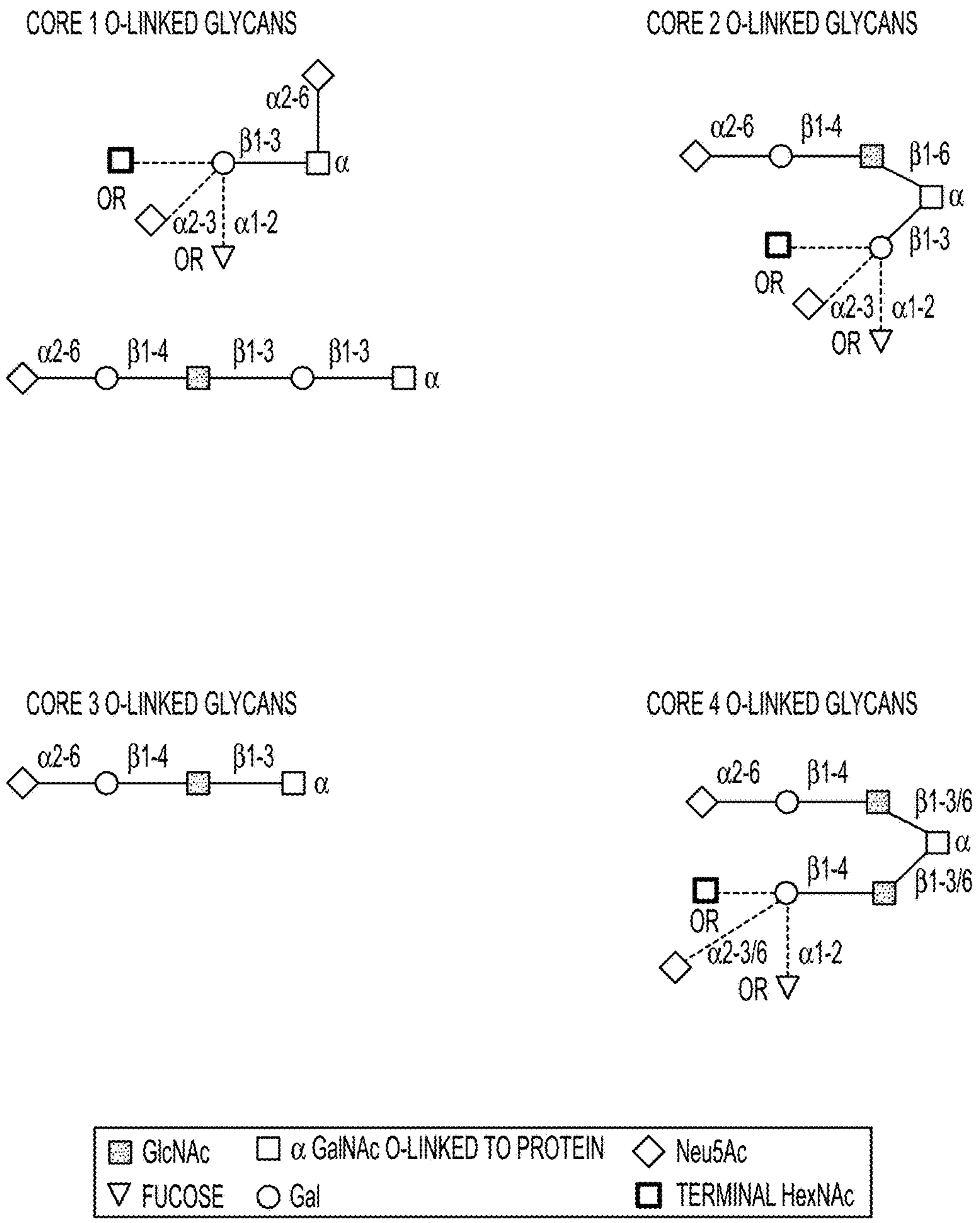
Figures 2, 12B:
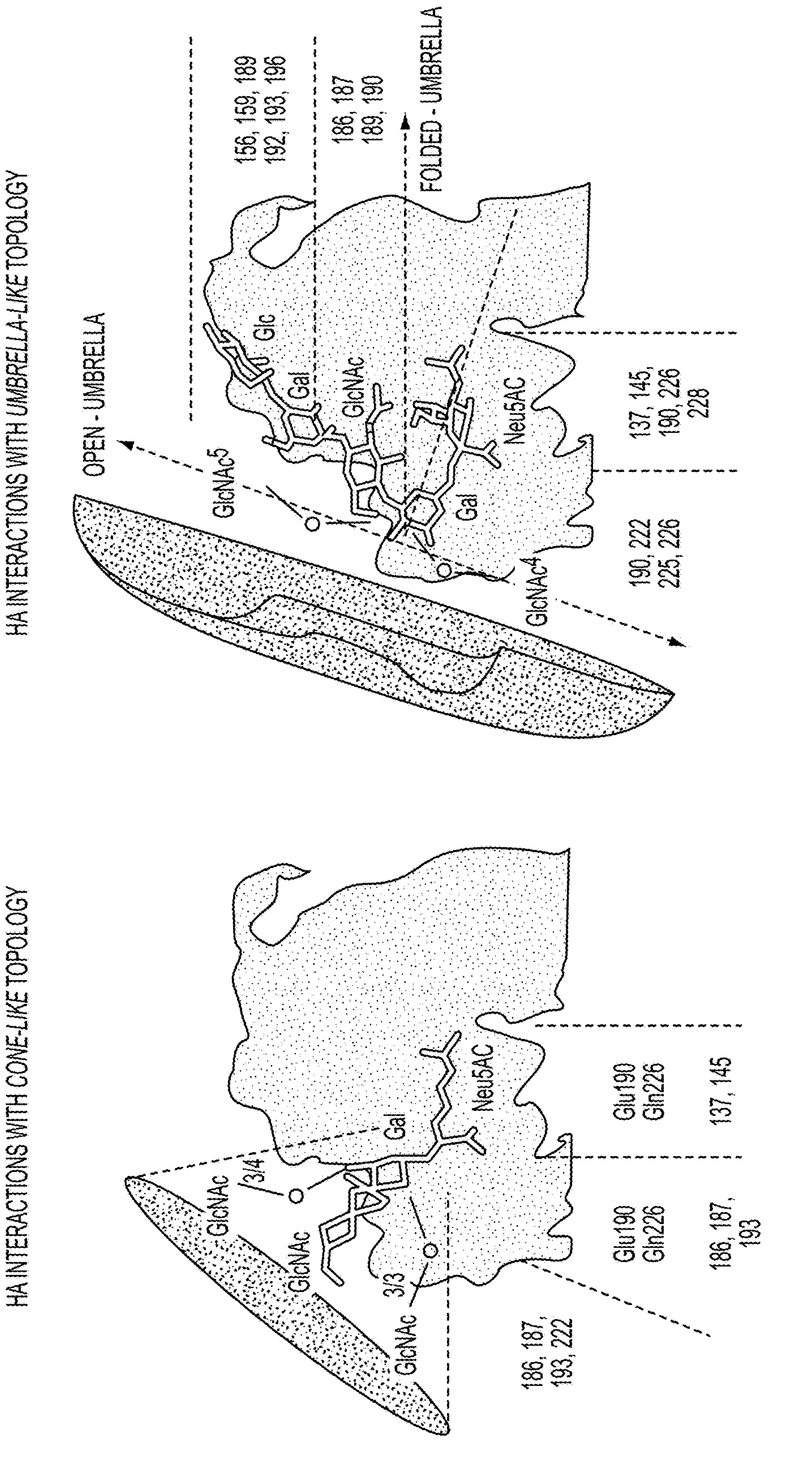
FIGS. 2A-E show alignment of exemplary sequences of wild type H3. Sequences were obtained from the NCBI influenza virus sequence database (available through the world wide web at ncbi.nlm.nih.gov/genomes/FLU/FLU).

Umbrella topology: The phrase "umbrella topology" is used herein to refer to a 3-dimensional arrangement adopted by certain glycans and in particular by glycans on HA receptors. The present invention encompasses the recognition that binding to umbrella topology glycans is characteristic of HA proteins that mediate infection of human hosts. As illustrated in FIG. 12, the umbrella topology is typically adopted only by α2-6 sialylated glycans, and is typical of long (e.g., greater than tetrasaccharide) oligosaccharides. In some embodiments, umbrella-topology glycans are glycans exhibiting a three-dimensional structure substantially similar to the structure presented in FIG. 6 (right panel). In some embodiments, umbrella-topology glycans are glycans which contact HA polypeptides via the amino acid residues shown in FIG. 6 (right panel). In some embodiments, umbrella-topology glycans are glycans which are able to contact and/or specifically bind to the amino acid binding pocket shown in FIG. 6 (right panel). In some embodiments, glycan structural topology is classified based on parameter θ defined as angle between $C_2$ of Sia, $C_1$ of Gal, and $C_1$ of GlcNAc. Values of θ<100° represent cone-like topology adopted by α2-3 and short α2-6 glycans. Values of θ>110° represent umbrella-like topology, such as topology adopted by long α2-6 glycans (FIG. 6). An example of umbrella topology is given by ϕ angle of Neu5Acα2-6Gal linkage of around −60 (see, for example, FIG. 11). FIG. 4 presents certain representative (though not exhaustive) examples of glycans that can adopt an umbrella topology. The long α2-6 motifs presented in FIG. 4 includes Neu5Acα2-6 linked at the non-reducing end to a long chain (e.g., at least a trisaccharide) found as a part of biological N-linked glycans, O-linked glycans, and glycolipids. The boxed inset shows examples of the umbrella-topology long α2-6 glycan moieties that are found as a part of biological glycans that bind to high affinity with HA. In some embodiments, umbrella-topology glycans (e.g., at a site) comprise a greater proportion of long (e.g. multiple lactosamine units) α2-6 oligosaccharide branches than short α2-6 (e.g. single lactosamine) branches. In some embodiments, umbrella-topology glycans (e.g., at a site) comprise about 2-fold, about 3-fold, about 4-fold, about 5-fold, about 10-fold, about 20-fold, about 50-fold, or greater than about 50-fold more long α2-6 oligosaccharide branches than short α2-6 (e.g. single lactosamine) branches. In some embodiments, the unique characteristic of HA interactions with umbrella-topology glycans and/or glycan decoys is the HA contact with a glycan comprising sialic acid (SA) and/or SA analogs at the non-reducing end. In some embodiments, chain length of the oligosaccharide is at least a trisaccharide (excluding the SA or SA analog). In some embodiments, a combination of the numbered residues shown in the right-hand panel of FIG. 12 is involved in contacts with umbrella-like topology. In some embodiments, umbrella topology glycans are oligosaccharides of the following form:

Neu5Acα2-6Sug1-Sug2-Sug3 where:

(a) Neu5Ac α2-6 is typically (but not essentially) at the non-reducing end;

(b) Sug1:

(i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);

(ii) no sugars other than Neu5Acα2-6 are attached to any of the non-reducing positions of Sug1 (except when Sug1 is GalNAcα- that is O-linked to the glycoprotein); and/or (iii) non-sugar moieties such as sulfate, phosphate, guanidium, amine, N-acetyl, etc. can be attached to non-reducing positions (typically 6 position) of Sug1 (e.g., to improve contacts with HA);

(c) Sug2 and/or Sug3 is/are:

(i) hexose (frequently Gal or Glc) or hexosamine (GlcNAc or GalNAc) in α or β configuration (frequently β); and/or (ii) sugars (such as Fuc) or non-sugar moieties such as sulfate, phosphate, guanidium, amine, N-acetyl, etc. can be attached to non-reducing positions of Sug2, Sug3, and/or Sug4;

(d) Linkage between any two sugars in the oligosaccharide apart from Neu5Acα2-6 linkage can be 1-2, 1-3, 1-4, and/or 1-6 (typically 1-3 or 1-4); and/or (e) Structure where Neu5Acα2-6 is linked GalNAcα that is O-linked to the glycoprotein and additional sugars are linked to the non-reducing end of GalNAcα for example (i) Neu5Acα2-6(Neu5Acα2-3Galβ1-3)GalNAcα-

(ii) Neu5Acα2-6(Galβ1-3)GalNAcα-

Umbrella topology blocking agent (UTBA): As used herein, the term "umbrella topology blocking agent" refers to an agent which binds to an HA receptor having an umbrella topology glycan. In some embodiments, a UTBA binds to an HA receptor having an umbrella topology glycan found in human upper airways. A UBTA can bind to either an umbrella topology glycan and/or to a cone topology glycan. In some embodiments, a UTBA selectively binds to an umbrella topology glycan with 50, 100, 150, or 200% of its affinity for a cone topology glycan. In some embodiments a UTBA selectively binds to an umbrella topology glycan with 50-150% of its affinity for a cone topology glycan. In some embodiments, and in some embodiments a UTBA binds to an umbrella topology glycan with about the same affinity as for a cone topology glycan. For example, in some embodiments, a UTBA binds an umbrella topology glycan (e.g., 6'SLN-LN) with about 50-200%, 50-150%, or about the same affinity to which it binds a cone topology glycan (e.g., 3'SLN-LN). In some embodiments, a UTBA selectively inhibits the binding of an influenza virus particle (e.g., a human or avian influenza virus) to the HA receptor based on the glycan topology of the receptor (e.g., umbrella or cone). In some embodiments, a UTBA is a polypeptide. In some such embodiments, a UTBA polypeptide has an amino acid sequence that is substantially identical or substantially homologous to that of a naturally-occurring polypeptide. In some embodiments, a UTBA polypeptide is an HA polypeptide. In some embodiments, a UTBA polypeptide is a naturally-occurring HA polypeptide, or a fragment thereof. In some embodiments, a UTBA polypeptide has an amino acid sequence that is not related to that of an HA polypeptide. In some embodiments, a UTBA polypeptide is an antibody or fragment thereof. In some embodiments, a UTBA polypeptide is a lectin (e.g., SNA-1). In some embodiments, a UTBA is not a polypeptide. In some embodiments, a UTBA is a small molecule. In some embodiments, a UTBA is a nucleic acid.

Umbrella topology glycan mimic: An "umbrella topology glycan mimic" is an agent, other than an umbrella topology glycan, that binds to binding agents as described herein. In some embodiments, umbrella topology glycan mimics are agents that bind to HA polypeptides. In some such embodiments, umbrella topology glycan mimics are agents that interact with HA polypeptide residues selected from the group consisting of residues 95, 98, 128, 130, 131, 132, 133, 135, 136, 137, 138, 145, 153, 155, 156, 158, 159, 160, 183, 186, 187, 188, 189, 190, 192, 193, 194, 195, 196, 219, 221, 222, 224, 225, 226, 227, 228 and combinations thereof. In some such embodiments, umbrella topology glycan mimics are agents that interact with HA polypeptide residues selected from the group consisting of residues 130, 131, 132, 133, 135, 137, 155, 188, 192, 193, 221, 226, 227, 228, and combinations thereof. In some such embodiments, umbrella topology glycan mimics are agents that interact with HA polypeptide residues selected from the group consisting of residues 160, 192, 193, and combinations thereof. Note that amino acid positions stated above are based on H3 HA numbering. In some embodiments, an HA topology glycan mimic is an agent that competes with umbrella topology glycans for interaction with an HA polypeptide.

Umbrella topology specific blocking agent (UTSBA): As used herein, the term "umbrella topology specific blocking agent" refers to an agent which binds to an HA receptor having an umbrella topology glycan found in human upper airways. A UTSBA selectively binds an umbrella topology glycan HA. For example, a UTSBA binds an umbrella topology glycan (e.g., 6'SLN-LN) with about at least 2, 4, 5, or 10 times greater affinity than it binds to a cone topology glycan (e.g., 3'SLN-LN). Typically, the affinity of a UTSBA for an umbrella topology glycan is greater than 1 nM. Typically the affinity of a UTSBA for a cone topology glycan is less is at least within 2 to 3 orders of magnitude of the binding affinity of umbrella topology glycans to human adapted HAs such as SC18, Mos99, Tx91, etc. and α2-6 binding plant lectins such as SNA-I. The binding affinity of UTSBA as measured by the dose-dependent direct binding assay (FIGS. 19 and 20) would typically be at least 1 nM. Typically the affinity of a UTSBA for a cone topology glycan is at most 1 to 3 orders of magnitude less than the binding affinity of cone topology glycans to avian HAs such as Viet0405, Av18, etc. In some embodiments, a UTSBA selectively inhibits binding of an influenza virus particle (e.g., a human or avian influenza virus) to the HA receptor (e.g., an H1, H2 or H3 or a human-adapted H5, H7 or H9) based on glycan topology (e.g., umbrella or cone). In some embodiments, a UTSBA is a polypeptide. In some such embodiments, a UTSBA polypeptide has an amino acid sequence that is that is substantially identical or substantially homologous to that of a naturally-occurring polypeptide. In some embodiments, a UTSBA polypeptide is an HA polypeptide. In some embodiments, a UTSBA polypeptide is a naturally-occurring HA polypeptide, or a fragment thereof. In some embodiments, a UTSBA polypeptide has an amino acid sequence that is not related to that of an HA polypeptide. In some embodiments, a UTSBA polypeptide is an antibody or fragment thereof. In some embodiments, a UTSBA polypeptide is a lectin (e.g., SNA-1). In some embodiments, a UTSBA is not a polypeptide. In some embodiments, a UTSBA is a small molecule. In some embodiments, a UTSBA is a nucleic acid.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Variant: As used herein, the term "variant" is a relative term that describes the relationship between a particular polypeptide (e.g., HA polypeptide) of interest and a "parent" polypeptide to which its sequence is being compared. A polypeptide of interest is considered to be a "variant" of a parent polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent polypeptide is one found in nature. For example, a parent HA polypeptide may be one found in a natural (e.g., wild type) isolate of an influenza virus (e.g., a wild type HA).

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic or prokaryotic cell. Vectors capable of directing the expression of operatively linked genes are referred to herein as "expression vectors."

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the world wide web at ncbi.nlm.nih.gov/genomes/FLU/FLU. Certain exemplary wild type H2 HA polypeptides are presented in FIG. 1.

DETAILED DESCRIPTION OF CERTAIN PARTICULAR EMBODIMENTS OF THE INVENTION

The present invention provides binding agents that show a strong ability to discriminate between umbrella-topology and cone-topology glycans. In some embodiments, provided binding agents are engineered HA polypeptides. In some embodiments, provided binding agents are engineered H2 HA polypeptides. In some embodiments, provided binding agents show an ability to discriminate between umbrella-topology and cone-topology glycans that is at least effective as that shown by an RTLS HA polypeptide (e.g., an RTLS H2 HA polypeptide) as described herein.

The present invention also provides systems and reagents for identifying binding agents that show a strong ability to discriminate between umbrella-topology and cone-topology glycans. The present invention also provides various reagents and methods associated with provided binding agents including, for example, systems for identifying them, strategies for preparing them, antibodies that bind to them, and various diagnostic and therapeutic methods relating to them. Further description of certain embodiments of these aspects, and others, of the present invention, is presented below.

Hemagglutinin (HA)

Influenza viruses are RNA viruses which are characterized by a lipid membrane envelope containing two glycoproteins, hemagglutinin (HA) and neuraminidase (NA), embedded in the membrane of the virus particular. There are 16 known HA subtypes and 9 NA subtypes, and different influenza strains are named based on the number of the strain's HA and NA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., 2004 *Virology,* 325:287, 2004; incorporated herein by reference).

HA exists in the membrane as a homotrimer of one of 16 subtypes, termed H1-H16. Only three of these subtypes (H1, H2, and H3) have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel & Wiley, 2000 *Annu Rev Biochem,* 69:531; Rogers, & Paulson, 1983 *Virology,* 127:361; Rogers et al., 1983 *Nature,* 304:76; Sauter et al., 1992 *Biochemistry,* 31:9609; Connor et al., 1994 *Virology,* 205:17; Tumpey et al., 2005 *Science,* 310:77; all of which are incorporated herein by reference). The present invention, however, encompasses the recognition that ability to infect human hosts correlates less with binding to glycans of a particular linkage, and more with binding to glycans of a particular topology. Thus, the present invention demonstrates that HAs that mediate infection of humans bind to umbrella topology glycans, often showing preference for umbrella topology glycans over cone topology glycans (even though cone-topology glycans may be α2-6 sialylated glycans).

Several crystal structures of HAs from H1 (human and swine), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., 1997 *Virology,* 232:19; Ha et al., 2001 *Proc Natl Acad Sci USA,* 98:11181; Ha et al., 2003 *Virology,* 309:209; Gamblin et al., 2004 *Science,* 303:1838; Stevens et al., 2004 *Science,* 303:1866; Russell et al., 2006 *Glycoconj J* 23:85; Stevens et al., 2006 *Science,* 312:404; all of which are incorporated herein by reference).

For example, the crystal structures of H5 (A/duck/Singapore/3/97) alone or bound to an α2-3 or an α2-6 sialylated oligosaccharide identifies certain amino acids that interact directly with bound glycans, and also amino acids that are one or more degree of separation removed (Stevens et al., 2001 *Proc Natl Acad Sci USA* 98:11181; incorporated herein by reference). In some cases, conformation of these residues is different in bound versus unbound states. For instance, Glu190, Lys193 and Gln226 all participate in direct-binding interactions and have different conformations in the bound versus the unbound state. The conformation of Asn186, which is proximal to Glu190, is also significantly different in the bound versus the unbound state.

Crystal structures of exemplary H2 HAs (human viruses A/Singapore/1/57 and A/Japan/305/57, avian viruses A/ck/Postdam/84, A/dk/Ontario/77 and A/ck/NewYork/91) complexed with analogs of human and avian HA receptors identify certain amino acids that interact directly with bound glycans and also mutations that alter the receptor binding pocket of HA (Xu R et al., 2010 *J Virol* 84(4):1715; Liu J, et al., 2009 *Proc Natl Acad Sci USA* 106(40):17175; each of which is incorporated herein by reference). Certain secondary structure elements of the binding site, e.g., the 130- and 220-loops and/or the 190-helix, may affect interactions with human and/or avian receptors. For example, human H2 HA residue 222 (Lys) forms a hydrogen bond with the 3'OH of Gal-2; human H2 HA residue 226 (leucine) is reported to lead to a more hydrophobic environment than that prevent in avian HA's (Liu J, et al., 2009 *Proc Natl Acad Sci USA* 106(40):17175). It has been reported that the receptor-binding site is formed by a shallow cavity surrounded by residues from the 190 helix (residues 190 to 198), the 220 loop (residues 221 to 228), the 130 loop (residues 134 to 138), and $Thr^{155}$ (Xu R et al., 2010 *J Virol* 84(4):1715). It has been observed that several conserved aromatic residues, including $Tyr^{98}$, $Trp^{153}$, and $His^{183}$, may form the bottom of the depression of the receptor-binding site (Xu R et al., 2010 *J Virol* 84(4):1715). In some embodiments, a sequence motif V/I H H P is present in the H2 HA receptor binding site, where the first H corresponds to a histidine at Residue 183. In some such embodiments, a glycine may be present at Residue 134, a tryptophan may be present at Residue 153, a threonine may be present at residue 155, a glutamic acid may be present at Residue 190, and/or a leucine may be present at Residue 194, and combinations thereof. In some embodiments, Residues 134, 153, 155, 190 and 194 are involved in binding to sialic acid.

Binding Agents

As described herein, binding to umbrella topology glycans correlates with ability to mediate infection of particular hosts, including for example, humans. Accordingly, the present invention provides binding agents (e.g., HA polypeptides, particularly H2 HA polypeptides, LSBAs, UTBAs, UTSBAs, etc.) that bind to umbrella glycans (and/or to umbrella topology glycan mimics). In some embodiments, inventive binding agents bind to umbrella glycans (and/or to umbrella topology glycan mimics) with high affinity. In some embodiments, inventive binding agents bind to a plurality of different umbrella topology glycans, often with high affinity and/or specificity.

In some embodiments, inventive binding agents bind to umbrella topology glycans (e.g., long α2-6 silaylated glycans such as, for example, Neu5Acα2-6Galβ1-4GlcNacβ1-3Galβ1-4GlcNAc-) with high affinity. For example, in some embodiments, inventive binding agents bind to umbrella topology glycans with an affinity comparable to that observed for a wild type HA that mediates infection of a humans. In some embodiments, a wild type HA that mediates infection in humans (e.g., is human transmissible) is an H1N1 HA, H2N2 HA, and/or H3N2 HA. In some embodiments, a wild type HA that mediates infection in humans (e.g., is human transmissible) is an HA from A/South Carolina/1/1918. In some embodiments, a wild type HA that mediates infection in humans (e.g., is human transmissible) is an HA from A/Albany/6/58. In some embodiments, inventive binding agents bind to umbrella glycans within a range of 10-fold or less (e.g., 9-fold, 8-fold, 7-fold, 6-fold, 5-fold, 4-fold, 3-fold, 2-fold, 1.5-fold, etc.) of the affinity for a wild type HA that mediates infection of a humans.

In some embodiments, inventive binding agents bind to umbrella glycans with an affinity that is at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100% of that observed under comparable conditions for a wild type HA that mediates infection of humans (e.g., is human transmissible). In some embodiments, inventive binding agents bind to umbrella glycans with an affinity that is greater than that observed under comparable conditions for a wild type HA that mediates infection of humans (e.g., is human transmissible).

In some embodiments, binding affinity of inventive binding agents is assessed over a range of concentrations. Such a strategy provides significantly more information, particularly in multivalent binding assays, than do single-concentration analyses. In some embodiments, for example, binding affinities of inventive binding agents are assessed over concentrations ranging over at least 2, at least 3, at least 4, at least 5, at least 6, at least 7, at least 8, at least 9, at least 10 or more fold.

In some embodiments, binding partner concentration (e.g., HA receptor, glycan, etc.) may be fixed to be in excess of ligand (e.g., an HA polypeptide) concentration so as to mimic physiological conditions (e.g., viral HA binding to cell surface glycans). Alternatively or additionally, in some embodiments, binding partner (e.g., HA receptor, glycan, etc.) concentration and/or ligand (e.g., an HA polypeptide) concentration may be varied. In some such embodiments, affinity (e.g., binding affinity) may be compared to a reference (e.g., a wild type HA that mediates infection of a humans) under comparable conditions (e.g., concentrations).

In some embodiments, binding affinity of inventive binding agents is performed using whole viruses. In some such embodiments, viral titer is measured in units that directly correlate with the number of viral particles.

In some embodiments, inventive binding agents show high affinity if they show a saturating signal in a multivalent glycan array binding assay such as those described herein. In some embodiments, inventive binding agents show high affinity if they show a signal above about 400000 or more (e.g., above about 500000, about 600000, about 700000, about 800000, etc) in such studies. In some embodiments, binding agents as described herein show saturating binding to umbrella glycans over a concentration range of at least 2 fold, at least 3 fold, at least 4 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold or more, and in some embodiments over a concentration range as large as at least 200 fold or more.

In some embodiments, provided binding agents show high affinity binding to umbrella topology glycans (and/or to umbrella topology glycan mimics). In some embodiments, provided binding agents show an affinity (Kd') for umbrella-topology glycans within the range of about 1.5 nM to about 2 pM. In some embodiments, provided binding agents show an affinity (Kd') for umbrella-topology glycans within the range of about 1.5 nM to about 200 pM. In some embodiments, provided binding agents show an affinity (Kd') for umbrella-topology glycans within the range of about 200 pM to about 10 pM. In some embodiments, provided binding agents show an affinity (Kd') for umbrella-topology glycans within the range of about 10 pM to about 2 pM. In some embodiments, provided binding agents show high affinity binding to umbrella topology glycans (and/or to umbrella topology glycan mimics) if they show a Kd' of about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays.

In some embodiments, provided binding agents show low affinity binding to cone topology glycans (and/or to cone topology glycan mimics). In some embodiments, provided binding agents show low affinity binding to cone topology glycans (and/or to cone topology glycan mimics) if they show a Kd' of about 100 pM or more (e.g., above about 200 pM, about 300 pM, about 400 pM, about 500 pM, about 600 pM, about 700 pM, about 800 pM, about 900 pM, about 1 nM, about 1.1 nM, about 1.2 nM, about 1.3 nM, about 1.4 nM, about 1.5 nM, etc.) in binding assays.

In some embodiments, provided binding agents show both high affinity to umbrella topology glycans (and/or to umbrella topology glycan mimics) and low affinity to cone topology glycans (and/or to cone topology glycan mimics). In some embodiments, provided binding agents show a Kd' of about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) for umbrella topology glycans and a Kd' of about 100 pM or more (e.g., above about 200 pM, about 300 pM, about 400 pM, about 500 pM, about 600 pM, about 700 pM, about 800 pM, about 900 pM, about 1 nM, about 1.1 nM, about 1.2 nM, about 1.3 nM, about 1.4 nM, about 1.5 nM, etc.) for cone topology glycans in binding assays.

In one aspect, the present invention provides the surprising recognition that high affinity for umbrella topology glycans, alone, may not be sufficient to mediate effective and/or efficient transmission to humans. Rather, according to the present disclosure, in some embodiments, provided binding agents show low binding to cone topology glycans and/or both high affinity for umbrella-topology glycans and low affinity for cone-topology glycans.

In some embodiments, inventive binding agents bind to α2-6 sialylated glycans; in some embodiments, inventive binding agents bind preferentially to α2-6 sialylated glycans. In some embodiments, inventive binding agents bind to a plurality of different α2-6 sialylated glycans. In some embodiments, inventive binding agents are not able to bind to α2-3 sialylated glycans, and in other embodiments inventive binding agents are able to bind to α2-3 sialylated glycans.

Furthermore, in some embodiments, inventive binding agents preferentially bind to umbrella topology glycans (and/or to umbrella topology glycan mimics) (e.g., they bind more strongly) than they bind to cone topology glycans. In some embodiments, inventive binding agents show a relative affinity for umbrella glycans vs cone glycans that is about 1, about 2, about 3, about 4, about 5, about 6, about 7, about 8, about 9, about 10, about 20, about 30, about 40, about 50, about 60, about 70, about 80, about 90, about 100, about 200, about 300, about 400, about 500, about 600, about 700, about 800, about 900, about 1000, about 2000, about 3000, about 4000, about 5000, about 6000, about 7000, about 8000, about 9000, about 10,000, up to about 100,000 or more. In some embodiments, inventive binding agents show an affinity for umbrella topology glycans that is about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, about 10,000% or more than their affinity for cone topology glycans.

In some embodiments, inventive binding agents bind to receptors found on human upper respiratory epithelial cells. In some embodiments, inventive binding agents bind to HA receptors in the bronchus and/or trachea. In some embodiments, inventive binding agents are not able to bind receptors in the deep lung, and in other embodiments, inventive binding agents are able to bind receptors in the deep lung.

In some embodiments, inventive binding agents bind to at least about 10%, about 15%, about 20%, about 25%, about 30% about 35%, about 40%, about 45%, about 50%, about 55%, about 60%, about 65%, about 70%, about 75%, about 80%, about 85%, about 90%, about 95% or more of the glycans found on HA receptors in human upper respiratory tract tissues (e.g., epithelial cells).

In some embodiments, inventive binding agents bind to one or more of the glycans illustrated in FIG. 4. In some embodiments, inventive binding agents bind to multiple glycans illustrated in FIG. 4. In some embodiments, inventive binding agents bind with high affinity and/or specificity to glycans illustrated in FIG. 4. In some embodiments, inventive binding agents bind to glycans illustrated in FIG. 4 preferentially as compared with their binding to glycans illustrated in FIG. 3. In some embodiments, inventive binding agents bind to an oligosaccharide of the following form:

Neu5Acα2-6Sug1-Sug2-Sug3 where:

1. Neu5Ac α2-6 is always or almost always at the non-reducing end;
2. Sug1:
   a. is a hexose (frequently Gal or Glc) or hexosamine (GlcNAc or GalNAc) in α or β configuration (frequently β- for N- and O-linked extension and α- in the case of GalNAcα- that is O-linked to glycoprotein);
   b. no sugars other than Neu5Acα2-6 should be attached to any of the non-reducing positions of Sug1 (except when Sug1 is GalNAcα- that is O-linked to the glycoprotein); and/or
   c. non-sugar moieties such as sulfate, phosphate, guanidium, amine, N-acetyl, etc. can be attached to non-reducing positions (typically 6 position) of Sug1 to improve contacts with HA;
3. Sug2 and/or Sug3:
   a. hexose (frequently Gal or Glc) or hexosamine (GlcNAc or GalNAc) in α or β configuration (frequently β); and/or
   b. sugars (such as Fuc) or non-sugar moieties such as sulfate, phosphate, guanidium, amine, N-acetyl, etc. can be attached to non-reducing positions of Sug2, Sug3, and/or Sug4;
4. Linkage between any two sugars in the oligosaccharide apart from Neu5Acα2-6 linkage can be 1-2, 1-3, 1-4, and/or 1-6 (typically 1-3 or 1-4); and/or
5. Structure where Neu5Acα2-6 is linked GalNAcα that is O-linked to the glycoprotein and additional sugars are linked to the non-reducing end of GalNAcα for example
   i. Neu5Acα2-6(Neu5Acα2-3Galβ1-3)GalNAcα-
   ii. Neu5Acα2-6(Galβ1-3)GalNAcα-

The present invention provides binding agents with designated binding specificity, and also provides binding agents with designated binding characteristics with respect to umbrella glycans.

Certain particular binding agents provided by the present invention are described in more detail below.

HA Polypeptides

In some embodiments, inventive binding agents are HA polypeptides. For example, the present invention provides isolated HA polypeptides with designated binding specificity, and also provides engineered HA polypeptides with designated binding characteristics with respect to umbrella glycans.

In some embodiments, provided HA polypeptides with designated binding characteristics are H1 polypeptides. In some embodiments, HA polypeptides in accordance with the invention with designated binding characteristics are H2 polypeptides. In some embodiments, HA polypeptides in accordance with the invention with designated binding characteristics are H3 polypeptides. In some embodiments, HA polypeptides in accordance with the invention with designated binding characteristics are H4 polypeptides. In some embodiments, HA polypeptides in accordance with the invention with designated binding characteristics are H5 polypeptides. In some embodiments, HA polypeptides in accordance with the invention with designated binding characteristics are H6 polypeptides. In some embodiments, HA polypeptides in accordance with the invention with designated binding characteristics are H7 polypeptides. In some embodiments, HA polypeptides in accordance with the invention with designated binding characteristics are H8 polypeptides. In some embodiments, HA polypeptides in accordance with the invention with designated binding characteristics are H9 polypeptides. In some embodiments, HA polypeptides in accordance with the invention with designated binding characteristics are H10 polypeptides. In some embodiments, HA polypeptides in accordance with the invention with designated binding characteristics are H11 polypeptides. In some embodiments, HA polypeptides in accordance with the invention with designated binding characteristics are H12 polypeptides. In some embodiments, HA polypeptides in accordance with the invention with designated binding characteristics are H13 polypeptides. In some embodiments, HA polypeptides in accordance with the invention with designated binding characteristics are H14 polypeptides. In some embodiments, HA polypeptides in accordance with the invention with designated binding characteristics are H15 polypeptides. In some embodiments, HA polypeptides in accordance with the invention with designated binding characteristics are H16 polypeptides.

In some embodiments, HA polypeptides in accordance with the invention with designated binding characteristics are not H1 polypeptides, are not H2 polypeptides, and/or are not H3 polypeptides.

In some embodiments, HA polypeptides in accordance with the invention do not include the H1 protein from any of the strains: A/South Carolina/1/1918; A/Puerto Rico/8/1934; A/Taiwan/1/1986; A/Texas/36/1991; A/Beijing/262/1995; A/Johannesburg/92/1996; A/New Caledonia/20/1999; A/Solomon Islands/3/2006.

In some embodiments, HA polypeptides in accordance with the invention are not the H2 protein from any of the strains of the Asian flu epidemic of 1957-58). In some embodiments, HA polypeptides in accordance with the invention do not include the H2 protein from any of the strains: A/Japan/305+/1957; A/Singapore/1/1957; A/Taiwan/1/1964; A/Taiwan/1/1967. In some embodiments, HA polypeptides in accordance with the invention do not include the H2 protein from A/Chicken/Pennsylvania/2004.

In some embodiments, HA polypeptides in accordance with the invention do not include the H3 protein from any of the strains: A/Aichi/2/1968; A/Philipines/2/1982; A/Mississippi/1/1985; A/Leningrad/360/1986; A/Sichuan/2/1987; A/Shanghai/11/1987; A/Beijing/353/1989; A/Shandong/9/1993; A/Johannesburg/33/1994; A/Nanchang/813/1995; A/Sydney/5/1997; A/Moscow/10/1999; A/Panama/2007/1999; A/Wyoming/3/2003; A/Oklahoma/323/2003; A/California/7/2004; A/Wisconsin/65/2005.

Engineered and/or Variant HA Polypeptides

In some embodiments, a provided HA polypeptide is a variant of a parent HA polypeptide in that its amino acid sequence is identical to that of the parent HA but for a small number of particular sequence alterations. In some embodiments, the parent HA is an HA polypeptide found in a natural isolate of an influenza virus (e.g., a wild type HA polypeptide). In some embodiments, the parent HA is an H2 HA polypeptide. In some embodiments, the parent HA is a wild-type H2 HA polypeptide. In some embodiments, the parent HA is an H2 HA selected from the group listed in FIG. 1. In some such embodiments, the parent HA is CkPA04. In some embodiments, the parent HA is Alb58. In some embodiments, the parent HA is A/Singapore/1/57 or A/Japan/305/57. In some embodiments, the parent HA is A/ck/NewYork/29878/91, A/dk/Ontario/77 or A/ck/postdam/4705/84.

In some embodiments, inventive HA polypeptide variants have different glycan binding characteristics than their corresponding parent HA polypeptides. In some embodiments, inventive HA variant polypeptides have greater affinity and/or specificity for umbrella glycans (e.g., as compared with for cone glycans) than do their cognate parent HA polypeptides. In some embodiments, such HA polypeptide variants are engineered variants.

In some embodiments, HA polypeptide variants with altered glycan binding characteristics have sequence alternations in residues within or affecting the glycan binding site. In some embodiments, such substitutions are of amino acids that interact directly with bound glycan; in other embodiments, such substitutions are of amino acids that are one degree of separation removed from those that interact with bound glycan, in that the one degree of separation removed—amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves. Inventive HA polypeptide variants contain substitutions of one or more direct-binding amino acids, one or more first degree of separation—amino acids, one or more second degree of separation—amino acids, or any combination of these. In some embodiments, inventive HA polypeptide variants may contain substitutions of one or more amino acids with even higher degrees of separation.

In some embodiments, HA polypeptide variants with altered glycan binding characteristics have sequence alterations in residues that make contact with sugars beyond Neu5Ac and Gal (see, for example, FIG. 13).

In some embodiments, HA polypeptide variants have at least one amino acid substitution, as compared with a wild type parent HA. In some embodiments, inventive HA polypeptide variants have at least two, three, four, five or more amino acid substitutions as compared with a cognate wild type parent HA; in some embodiments inventive HA polypeptide variants have two, three, or four amino acid substitutions. In some embodiments, all such amino acid substitutions are located within the glycan binding site.

In some embodiments, an HA polypeptide variant, and particularly an H2 polypeptide variant has one or more amino acid substitutions relative to a wild type parent HA at residues selected from amino acids that are one degree of separation removed from those that interact with bound glycan, in that the one degree of separation removed— amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues 137, 145, 156, 159, 186, 187, 189, 190, 192, 193, 196, 222, 225, 226, and 228.

In some embodiments, HA polypeptide variants, and particularly H2 polypeptide variants, have sequence substitutions at positions corresponding to one or more of residues 137, 193, 226, and 228. Alternatively or additionally, in some embodiments, HA polypeptide variants have sequence substitutions at positions corresponding to one or more of residues 145, 156, 159, 186, 187, 189, 190, 192, 196, 222 and 225.

In some embodiments, provided HA polypeptides such as HA polypeptide variants (e.g., H2 HA polypeptides such as H2 HA polypeptide variants) have an amino acid residue at a position corresponding to 137 (a "Residue 137") that is selected from arginine, lysine, glutamine, methionine and histidine. In some embodiments, provided HA polypeptides such as HA polypeptide variants (e.g., H2 HA polypeptides such as H2 HA polypeptide variants) have an amino acid residue at a position corresponding to 137 (a "Residue 137") that is selected from arginine, lysine, glutamine, and methionine. In some embodiments, provided HA polypeptides such as HA polypeptide variants (e.g., H2 HA polypeptides such as H2 HA polypeptide variants) have an amino acid residue at a position corresponding to 137 (a "Residue 137") that is selected from arginine and lysine. In some embodiments, provided HA polypeptides and/or polypeptide variants (e.g., H2 HA polypeptide variants) have an arginine residue as Residue 137.

In some embodiments, provided HA polypeptides such as HA polypeptide variants (e.g., H2 HA polypeptides such as H2 HA polypeptide variants) have a an amino acid residue at a position corresponding to 193 ("Residue 193") that is selected from the group consisting of alanine, aspartic acid, glutamic acid, leucine, isoleucine, methionine, serine, threonine, cysteine, and valine. In some embodiments, provided HA polypeptides such as HA polypeptide variants (e.g., H2 HA polypeptides such as H2 HA polypeptide variants) have a Residue 193 that is selected from the group consisting of alanine, glutamic acid, threonine, cysteine, methionine, valine, and serine. In some embodiments, provided HA polypeptides such as HA polypeptide variants (e.g., H2 HA polypeptides such as H2 HA polypeptide variants) have a Residue 193 that is selected from the group consisting of alanine, glutamic acid and threonine. In some embodiments, provided HA polypeptides such as HA polypeptide variants (e.g., H2 HA polypeptides such as H2 HA polypeptide variants) have a Residue 193 that is threonine.

In some embodiments, provided HA polypeptides such as HA polypeptide variants (e.g., H2 HA polypeptides such as H2 HA polypeptide variants) have an amino acid as a residue corresponding to residue 226 ("Residue 226") that is a nonpolar amino acid. In some embodiments, provided HA polypeptides such as HA polypeptide variants (e.g., H2 HA polypeptides such as H2 HA polypeptide variants) have a Residue 226 that is selected from the group consisting of alanine, cysteine, glycine, isoleucine, leucine, methionine, phenylalanine, proline, tryptophan and valine. In some embodiments, provided HA polypeptides such as HA polypeptide variants (e.g., H2 HA polypeptides such as H2 HA polypeptide variants) have a Residue 226 that is selected from the group consisting of leucine, isoleucine and valine. In some embodiments, provided HA polypeptides such as HA polypeptide variants (e.g., H2 HA polypeptides such as H2 HA polypeptide variants) have a Residue 226 that is leucine.

In some embodiments, provided HA polypeptides such as HA polypeptide variants (e.g., H2 HA polypeptides such as H2 HA polypeptide variants) have an amino acid residue at a position corresponding to 228 ("Residue 228") that is a polar amino acid. In some embodiments, provided HA polypeptides such as HA polypeptide variants (e.g., H2 HA polypeptides such as H2 HA polypeptide variants) have a Residue 228 that is selected from the group consisting of arginine, asparagine, aspartic acid, glutamic acid, glutamine, histidine, lysine, serine, glycine, threonine, and tyrosine. In some embodiments, provided HA polypeptides such as HA polypeptide variants (e.g., H2 HA polypeptides such as H2 HA polypeptide variants) have Residue 228 that is selected from the group consisting of arginine, asparagine, serine, glycine, and threonine. In some embodiments, provided HA polypeptides such as HA polypeptide variants (e.g., H2 HA polypeptides such as H2 HA polypeptide variants) have a Residue 228 that is serine.

In some embodiments, provided HA polypeptide variants have at least one substitution in a position other than 137, 193, 226, and/or 228, as compared with a particular reference HA polypeptide (e.g., with a wild type HA polypeptide such as a wild type H2 HA polypeptide, for example as described herein). In some such embodiments, affinity and/or specificity of the variant for umbrella-topology glycans is increased.

In some embodiments, provided HA polypeptides such as HA polypeptide variants (e.g., H2 HA polypeptides such as H2 HA polypeptide variants) have an amino acid at a particular residue (e.g., 137, 145, 186, 187, 189, 190, 192, 193, 222, 225, 226, 228) that is predominantly present in the corresponding human-adapted HA (e.g., human-adapted H2 HA, such as those shown in FIG. 1). In some embodiments, provided HA polypeptides such as HA polypeptide variants (e.g., H2 HA polypeptides such as H2 HA polypeptide variants) have at least one amino acid substitution that is found in the corresponding human-adapted HA (e.g., human-adapted H2 HA).

In some embodiments, inventive HA polypeptide variants have an open binding site as compared with a reference or parent HA, and particularly with a parent wild type HAs.

Portions or Fragments of HA Polypeptides

The present invention further provides characteristic portions (which may or may not be binding agents) of HA polypeptides in accordance with the invention (and/or polypeptide variants) and nucleic acids that encode them. In general, a characteristic portion is one that contains a continuous stretch of amino acids, or a collection of continuous stretches of amino acids, that together are characteristic of the HA polypeptide. Each such continuous stretch generally will contain at least two amino acids. Furthermore, those of ordinary skill in the art will appreciate that typically at least 5, 10, 15, 20 or more amino acids are required to be characteristic of an HA polypeptide (e.g., an H2 HA polypeptide). In general, a characteristic portion is one that, in addition to the sequence identity specified above, shares at least one functional characteristic with the relevant intact HA polypeptide. In some embodiments, inventive characteristic portions of HA polypeptides share glycan binding characteristics with the relevant full-length HA polypeptides.

Non-HA Polypeptides

In some embodiments, binding agents provided in accordance with the present invention are polypeptides whose amino acid sequence does not include a characteristic HA sequence. Such polypeptides are referred to herein as "Non-HA polypeptides". In some embodiments, a Non-HA polypeptide has an amino acid sequence selected in advance (e.g., via rational design, including for example, introduction of strategic amino acid alterations [additions, deletions, and/or substitutions] as compared with a reference sequence). In some embodiments, a Non-HA polypeptide has an amino acid sequence that is determined stochastically and, for example, identified on the basis of the desirable binding characteristics defined herein.

Antibodies

In some embodiments, binding agents provided in accordance with the present invention are antibodies (e.g., that bind to umbrella topology glycans and/or to umbrella topology glycan mimics). Antibodies suitable for the invention include antibodies or fragments of antibodies that bind immunospecifically to any umbrella topology glycan epitope. As used herein, the term "antibodies" is intended to include immunoglobulins and fragments thereof which are specifically reactive to the designated protein or peptide, or fragments thereof. Suitable antibodies include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. Antibody polypeptides for use herein may be of any type (e.g., IgA, IgD, IgE, IgG, IgM).

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Antibodies can be generated using methods well known in the art. For example, protocols for antibody production are described by Harlow and Lane, 1988, *Antibodies: A Laboratory Manual*; incorporated herein by reference. Typically, antibodies can be generated in mouse, rat, guinea pig, hamster, camel, llama, shark, or other appropriate host. Alternatively, antibodies may be made in chickens, producing IgY molecules (Schade et al., 1996 *ALTEX* 13(5):80; incorporated herein by reference). In some embodiments, antibodies suitable for the present invention are subhuman primate antibodies. For example, general techniques for raising therapeutically useful antibodies in baboons may be found, for example, in Goldenberg et al., international patent publication No. WO 91/11465 (1991), and in Losman et al., 1990 *Int. J. Cancer* 46: 310; each of which is incorporated herein by reference. In some embodiments, monoclonal antibodies may be prepared using hybridoma methods (Milstein and Cuello, 1983 *Nature* 305(5934):537; incorporated herein by reference). In some embodiments, monoclonal antibodies may also be made by recombinant methods (U.S. Pat. No. 4,166,452, 1979; incorporated herein by reference).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., 1988 *Nature* 332(6162):323; Verhoeyen et al., 1988 *Science.* 239(4847):1534; each of which is incorporated herein by reference.). Such "humanized" antibodies are chimeric Abs (U.S. Pat. No. 4,816,567, 1989; incorporated herein by reference), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., 1988 *Nature* 332(6162):323; Verhoeyen et al., 1988 *Science.* 239(4847):1534; each of which is incorporated herein by reference).

Human antibodies can also be produced using various techniques, including phage display libraries (Hoogenboom et al., 1991 *Mol Immunol.* 28(9):1027-37; Marks et al., 1991 *J Mol Biol.* 222(3):581-97; each of which is incorporated herein by reference) and the preparation of human monoclonal antibodies (Reisfeld and Sell, 1985, *Cancer Surv.* 4(1):271-90; incorporated herein by reference). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., High-avidity human IgG kappa monoclonal antibodies from a novel strain of minilocus transgenic mice, *Nat Biotechnol.* 1996 July; 14(7): 845-51; Lonberg et al., Antigen-specific human antibodies from mice comprising four distinct genetic modifications, *Nature* 1994 Apr. 28; 368(6474):856-9; Lonberg and Huszar, Human antibodies from transgenic mice, *Int. Rev. Immunol.* 1995; 13(1):65-93; Marks et al., By-passing immunization: building high affinity human antibodies by chain shuffling. *Biotechnology* (NY). 1992 July; 10(7):779-83; each of which is incorporated herein by reference).

Lectins

In some embodiments, binding agents provided in accordance with the present invention are lectins. Lectins are sugar-binding proteins which may bind to a soluble carbohydrate or to a carbohydrate moiety which is a part of a glycoconjugate (e.g., a glycopeptide or glycolipid). Lectins typically agglutinate certain animal cells and/or precipitate glycoconjugates by recognizing a particular sugar moiety. For example, SNA-1 is a lectin that has a high affinity for α2-6 sialic acids. As yet another example, polyporus squamosus lectins (PSL1a and PSL1b) have high affinity for binding sialylated glycoconjugates containing Neu5Acα2, 6Galβ1,4Glc/GlcNAc trisaccharide sequences of asparagine-linked glycoproteins. Non-limiting exemplary lectins that may act as binding agents include SNA-1, SNA-1', PSL1a, PSL1b, and polypeptides derived therefrom.

Amino acid sequences of exemplary lectins are provided below in Tables 1-4.

TABLE 1

| Sambucus Nigra Lectin 1 (Genbank Accession No. U27122): |
|---|
| MRLVAKLLYLAVLAICGLGIHGALTHPRVTPPVYPSVSFNLTGADTYEPF |
| LRALQEKVILGNHTAFDLPVLNPESQVSDSNRFVLVPLTNPSGDTVTLAI |
| DVVNLYVVAFSSNGKSYFFSGSTAVQRDNLFVDTTQEELNFTGNYTSLER |
| QVGFGRVYIPLGPKSLDQAISSLRTYTLTAGDTKPLARGLLVVIQMVSEA |
| ARFRYIELRIRTSITDASEFTPDLLMLSMENNWSSMSSEIQQAQPGGIFA |
| GVVQLRDERNNSIEVTNFRRLFELTYIAVLLYGCAPVTSSSYSNNAIDAQ |
| IIKMPVFRGGEYEKVCSVVEVTRRISGWDGLCVDVRYGHYIDGNPVQLRP |
| CGNECNQLWTFRTDGTIRWLGKCLTASSSVMIYDCNTVPPEATKWVVSID |
| GTITNPHSGLVLTAPQAAEGTALSLENNIHAARQGWTVGDVEPLVTFIVG |
| YKQMCLRENGENNFVWLEDCVLNRVQQEWALYGDGTIRVNSNRSLCVTSE |
| DHEPSDLIVILKCEGSGNQRWVFNTNGTISNPNAKLLMDVAQRDVSLRKI |
| ILYRPTGNPNQQWITTTHPA (SEQ ID NO: 24) |

TABLE 2

| Sambucus Nigra Lectin 1' (Genbank Accession No. U66191): |
|---|
| MKVVATILYLVVLAICGLGIHGAHPTHSAPPTVYPSVSFNLTEANSNEYR |
| HFLQELRGKVILGSHRAFDLPVLNPESKVSDSDRFVLVRLTNPSRKKVTL |
| AIDVVTFYVVAFAQNDRSYFFSGSSEVQRENLFVDTTQEDLNFKGDYTSL |
| EHQVGFGRVYIPLGPKSLAQSISSLSTYKSSAGDNKRLARSLLVVIQMVS |

TABLE 2-continued

| Sambucus Nigra Lectin 1' (Genbank Accession No. U66191): |
|---|
| EAARFRYIQLRIQASITDAKEFTPDLLMLSMENKWSSMSSEIQQAQPGGA |
| FAQVVKLLDQRNHPIDVTNFRRLFQLTSVAVLLHGCPTVTKMPAYIIKMP |
| VFNGGEDEERCSVVEEVTRRIGGRDGFCAEVKNGDEKDGTPVQLSSCGEQ |
| SNQQWTFSTDGTIQSLGKCLTTSSSVMIYNCKVVPPESTKWVVSIDGTIT |
| NPRSGLVLTAPKAAEGTLVSLEKNVHAARQGWIVGNVEPLVTFIVGYEQM |
| CLETNPGNNDVSLGDCSVKSASKVDQKWALYGDGTIRVNNDRSLCVTSEG |
| KSSNEPIIILKCLGWANQRWVFNTDGTISNPDSKLVMHVDQNDVPLRKII |
| LSHPSGTSNQQWIASTHPA (SEQ ID NO: 25) |

TABLE 3

| Polyporous squamosus lectin 1a (UniProt Q75WT9) |
|---|
| MSFQGHGIYYIASAYVANTRLALSEDSSANKSPDVIISSDAVDPLNNLWL |
| IEPVGEADTYTVRNAFAGSYMDLAGHAATDGTAIIGYRPTGGDNQKWIIS |
| QINDVWKIKSKETGTFVTLLNGDGGGTGTVVGWQNITNNTSQNWTFQKLS |
| QTGANVHATLLACPALRQDFKSYLSDGLYLVLTRDQISSIWQASGLGSTP |
| WRSEIFDCDDFATVFKGAVAKWGNENFKANGFALLCGLMFGSKSSGAHAY |
| NWFVERGNFSTVTFFEPQNGTYSANAWDYKAYFGLF (SEQ ID NO: |
| 26) |

TABLE 4

| Polyporous squamosus lectin 1b (UniProt Q75WT8) |
|---|
| MSFEGHGIYHIPHAHVANIRMALANRGSGQNGTPVIAWDSNNDAFDHMWL |
| VEPTGEADTYTIHNVSTGTYMDVTASAVADNTPIIGYQRTGNDNQKWIIR |
| QVQTDGGDRPWKIQCKATGTFATLYSGGGSGTAIVGWRLVNSNGNQDWVF |
| QKLSQTSVNVHATLLACGATVGQDFKNYLYDGLYLVLPRDRISAIWKASG |
| LGETARRDGIYDSDEFAMTFKSAAATWGKENFKADGFAILCGMMFGTKAS |
| TNRHAYNWVVERGSFSTVTFFEPQNGTYSDDAWGYKAYFGLF (SEQ ID |
| NO: 27) |

Aptamers

In some embodiments, binding agents provided in accordance with the present invention are aptamers. Aptamers are macromolecules composed of nucleic acid (e.g., RNA, DNA) that bind tightly to a specific molecular target (e.g., an umbrella topology glycan). A particular aptamer may be described by a linear nucleotide sequence and is typically about 15 to about 60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules.

In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Selection of aptamers that can bind umbrella topology glycans (and/or to umbrella topology glycan mimics) can be achieved through methods known in the art. For example, aptamers can be selected using the SELEX (Systematic Evolution of Ligands by Exponential Enrichment) method (Tuerk, C., and Gold, L., 1990 *Science* 249:505; incorporated herein by reference). In the SELEX method, a large library of nucleic acid molecules (e.g., $10^{15}$ different molecules) is produced and/or screened with the target molecule (e.g., an umbrella topology glycan of umbrella topology glycan epitope). The target molecule is allowed to incubate with the library of nucleotide sequences for a period of time. Several methods, known in the art, can then be used to physically isolate the aptamer target molecules from the unbound molecules in the mixture, which can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this iterative selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure, thereby producing aptamers truncated to their core binding domain. See Jayasena, S. D. 1999 *Clin. Chem.* 45:1628-1650, for review of aptamer technology; the entire teachings of which are incorporated herein by reference).

Production of Polypeptides

Inventive polypeptides (e.g., HA polypeptides and/or Non-HA polypeptides), and/or characteristic portions thereof, or nucleic acids encoding them, may be produced by any available means.

Inventive polypeptides (or characteristic portions) may be produced, for example, by utilizing a host cell system engineered to express an inventive polypeptide-encoding nucleic acid.

Any system can be used to produce polypeptides (or characteristic portions), such as egg, baculovirus, plant, yeast, Madin-Darby Canine Kidney cells (MDCK), or Vero (African green monkey kidney) cells. Alternatively or additionally, polypeptides (or characteristic portions) can be expressed in cells using recombinant techniques, such as through the use of an expression vector (Sambrook et al., 1989 *Molecular Cloning: A Laboratory Manual*, CSHL Press; incorporated herein by reference).

Alternatively or additionally, inventive polypeptides (or characteristic portions thereof) can be produced by synthetic means.

Alternatively or additionally, inventive polypeptides (or characteristic portions thereof), and particularly HA polypeptides, may be produced in the context of intact virus, whether otherwise wild type, attenuated, killed, etc. Inventive polypeptides (e.g., HA polypeptides), or characteristic portions thereof, may also be produced in the context of virus like particles.

In some embodiments, HA polypeptides (or characteristic portions thereof) can be isolated and/or purified from influenza virus. For example, virus may be grown in eggs, such as embryonated hen eggs, in which case the harvested material is typically allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Also, it will be appreciated by those of ordinary skill in the art that polypeptides, and particularly variant HA polypeptides as described herein, may be generated, identified, isolated, and/or produced by culturing cells or organisms that produce the polypeptide (whether alone or as part of a complex, including as part of a virus particle or virus), under conditions that allow ready screening and/or selection of polypeptides capable of binding to umbrella-topology glycans. To give but one example, in some embodiments, it may be useful to produce and/or study a collection of polypeptides (e.g., HA variant polypeptides) under conditions that reveal and/or favor those variants that bind to umbrella topology glycans (e.g., with particular specificity and/or affinity). In some embodiments, such a collection of polypeptides (e.g., HA variant polypeptides) results from evolution in nature. In some embodiments, such a collection of polypeptides (e.g., HA variant polypeptides) results from engineering. In some embodiments, such a collection of polypeptides (e.g., HA variant polypeptides) results from a combination of engineering and natural evolution.

HA Receptors

HA interacts with the surface of cells by binding to a glycoprotein receptor. Binding of HA to HA receptors is predominantly mediated by N-linked glycans on the HA receptors. Specifically, HA on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells. Some crystal structures of exemplary HA-glycan interactions have been identified and are presented in Table 5:

TABLE 5

| Crystal Structures of HA-Glycan Complexes | | |
|---|---|---|
| Abbreviation (PDB ID) | Virus Strain | Glycan (with assigned coordinates) |
| ADkALB76_H1_26 (2WRH) | A/duck/Alberta/76 (H1N1) | Neu5Ac |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| ASC18_H1_26 (2WRG) | A/South Carolina/1/18 (H1N1) | Neu5Acα6Galβ4GlcNAcβ3Gal |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ACkNY91_H2_23 (2WR2) | A/chicken/NY/29878/91 (H2N2) | Neu5Acα3Galβ3GlcNAc |
| ACkNY91_H2_26 (2WR1) | A/chicken/NY/29878/91 (H2N2) | Neu5Acα6Galβ4GlcNAc |
| ADkON77_H2_23 (2WR3) | A/duck/Ontario/77 (H2N2) | Neu5Acα3Galβ4GlcNAc |
| ADkON77_H2_26 (2WR4) | A/duck/Ontario/77 (H2N2) | Neu5Acα6Galβ4GlcNAc |
| ACkPD84_H2_26 (2WRF) | A/chicken/Potsdam/475/84 (H2N2) | Neu5Acα6Gal |
| ASING57_H2_23 (2WRB) | A/Singapore/1/57 (H2N2) | Neu5Ac |
| ASING57_H2_26 (2WR7) | A/Singapore/1/57 (H2N2) | Neu5Acα6Galβ4GlcNAcβ3Gal |
| AJAP57_H2_26(2WRE) | A/Japan/305/57 (H2N2) | Neu5Acα6Gal |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

HA-α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2-6 sialylated glycans are published (Eisen et al., 1997, *Virology,* 232:19), their coordinates were not available in the Protein Data Bank. The SARF2 (http://123d.ncifcrf.gov/sarf2.html) program was used to obtain the structural alignment of the different HA1 subunits for superimposition.

HA receptors are modified by either α2-3 or α2-6 sialylated glycans near the receptor's HA-binding site, and the type of linkage of the receptor-bound glycan can affect the conformation of the receptor's HA-binding site, thus affecting the receptor's specificity for different HAs.

For example, the glycan binding pocket of avian HA is narrow. According to the present invention, this pocket binds to the trans conformation of α2-3 sialylated glycans, and/or to cone-topology glycans, whether α2-3 or α2-6 linked.

HA receptors in avian tissues, and also in human deep lung and gastrointestinal (GI) tract tissues are characterized by α2-3 sialylated glycan linkages, and furthermore (according to the present invention), are characterized by glycans, including α2-3 sialylated and/or α2-6 sialylated glycans, which predominantly adopt cone topologies. HA receptors having such cone-topology glycans may be referred to herein as CTHArs.

By contrast, human HA receptors in the bronchus and trachea of the upper respiratory tract are modified by α2-6 sialylated glycans. Unlike the α2-3 motif, the α2-6 motif has an additional degree of conformational freedom due to the C6-05 bond (Russell et al., 2006 *Glycoconj J* 23:85; incorporated herein by reference). HAs that bind to such α2-6 sialylated glycans have a more open binding pocket to accommodate the diversity of structures arising from this conformational freedom. Moreover, according to the present invention, HAs may need to bind to glycans (e.g., α2-6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild type avian HAs (e.g., avian H2). Specifically, because the portions of the human respiratory tract that are most likely to encounter virus (i.e., the trachea and bronchi) lack receptors with cone glycans (e.g., α2-3 sialylated glycans, and/or short glycans) and wild type avian HAs typically bind primarily or exclusively to receptors associated with cone glycans (e.g., α2-3 sialylated glycans, and/or short glycans), humans rarely become infected with avian viruses. Only when in sufficiently close contact with virus that it can access the deep lung and/or gastrointestinal tract receptors having umbrella glycans (e.g., long α2-6 sialylated glycans) do humans become infected.

Glycan Arrays

To rapidly expand the current knowledge of known specific glycan-glycan binding protein (GBP) interactions, the Consortium for Functional Glycomics (CFG; available through the world wide web functionalglycomics.org), an international collaborative research initiative, has developed glycan arrays comprising several glycan structures that have enabled high throughput screening of GBPs for novel glycan ligand specificities. The glycan arrays comprise both monovalent and polyvalent glycan motifs (i.e. attached to polyacrylamide backbone), and each array comprises 264 glycans with low (10 μM) and high (100 μM) concentrations, and six spots for each concentration (available through the world wide web at functionalglycomics.org/static/consortium/resources/resourcecoreh5).

The arrays predominantly comprise synthetic glycans that capture the physiological diversity of N- and O-linked glycans. In addition to the synthetic glycans, N-linked glycan mixtures derived from different mammalian glycoproteins are also represented on the array.

As used herein, a glycan "array" refers to a set of one or more glycans, optionally immobilized on a solid support. In some embodiments, an "array" is a collection of glycans present as an organized arrangement or pattern at two or more locations that are physically separated in space. Typically, a glycan array will have at least 4, at least 8, at least 16, at least 24, at least 48, at least 96 or several hundred or thousand discrete locations. In general, inventive glycan arrays may have any of a variety of formats. Various different array formats applicable to biomolecules are known in the art. For example, a huge number of protein and/or nucleic acid arrays are well known. Those of ordinary skill in the art will immediately appreciate standard array formats appropriate for glycan arrays of the present invention.

In some embodiments, inventive glycan arrays are present in "microarray" formats. A microarray may typically have sample locations separated by a distance of about 50 to about 200 microns or less and immobilized sample in the nano to micromolar range or nano to picogram range. Array formats known in the art include, for example, those in which each discrete sample location has a scale of, for example, ten microns.

In some embodiments, inventive glycan arrays comprise a plurality of glycans spatially immobilized on a support. The present invention provides glycan molecules arrayed on a support. As used herein, "support" refers to any material which is suitable to be used to array glycan molecules. As will be appreciated by those of ordinary skill in the art, any of a wide variety of materials may be employed. To give but a few examples, support materials which may be of use in the invention include hydrophobic membranes, for example, nitrocellulose, PVDF or nylon membranes. Such membranes are well known in the art and can be obtained from, for example, Bio-Rad, Hemel Hempstead, UK.

In some embodiments, the support on which glycans are arrayed may comprise a metal oxide. Suitable metal oxides include, but are not limited to, titanium oxide, tantalum oxide, and aluminum oxide. Examples of such materials may be obtained from Sigma-Aldrich Company Ltd, Fancy Road, Poole, Dorset. BH12 4QH UK.

In some embodiments, such a support is or comprises a metal oxide gel. A metal oxide gel is considered to provide a large surface area within a given macroscopic area to aid immobilization of the carbohydrate-containing molecules.

Additional or alternative support materials which may be used in accordance with the present invention include gels, for example silica gels or aluminum oxide gels. Examples of such materials may be obtained from, for example, Merck KGaA, Darmstadt, Germany.

In some embodiments, glycan arrays are immobilized on a support that can resist change in size or shape during normal use. For example a support may be a glass slide coated with a component material suitable to be used to array glycans. Also, some composite materials can desirable provide solidity to a support.

As demonstrated herein, inventive arrays are useful for the identification and/or characterization of different HA polypeptides and their binding characteristics. In some embodiments, HA polypeptides in accordance with the invention are tested on such arrays to assess their ability to bind to umbrella topology glycans (e.g., to α2-6 sialylated glycans, and particularly to long α2-6 sialylated glycans arranged in an umbrella topology).

Indeed, the present invention provides arrays of α2-6 sialylated glycans, and optionally α2-3 sialylated glycans, that can be used to characterize HA polypeptide binding capabilities and/or as a diagnostic to detect, for example, human-binding HA polypeptides. In some embodiments, inventive arrays contain glycans (e.g., α2-6 sialylated glycans, and particularly long α2-6 sialylated glycans) in an umbrella topology. As will be clear to those of ordinary skill in the art, such arrays are useful for characterizing or detecting any HA polypeptides, including for example, those found in natural influenza isolates in addition to those designed and/or prepared by researchers.

In some embodiments, such arrays include glycans representative of about 10%, about 15%, about 20%, about 25%, about 30%, about 35%, about 40%, about 45%, about 50%, about 55%, about 60%, about 65%, about 70%, about 75%, about 80%, about 85%, about 90% about 95%, or more of the glycans (e.g., the umbrella glycans, which will often be α2-6 sialylated glycans, particularly long α2-6 sialylated glycans) found on human HA receptors, and particularly on human upper respiratory tract HA receptors. In some embodiments, inventive arrays include some or all of the glycan structures depicted in FIG. 14. In some embodiments, arrays include at least about 10%, about 15%, about 20%, about 25%, about 30% about 35%, about 40%, about 45%, about 50%, about 55%, about 60%, about 65%, about 70%, about 75%, about 80%, about 85%, about 90% about 95%, or more of these depicted glycans.

The present invention provides methods for identifying or characterizing HA polypeptides using glycan arrays. In some embodiments, for example, such methods comprise steps of (1) providing a sample containing HA polypeptide, (2) contacting the sample with a glycan array comprising, and (3) detecting binding of HA polypeptide to one or more glycans on the array.

Suitable sources for samples containing HA polypeptides to be contacted with glycan arrays according to the present invention include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples containing HA polypeptides include, but are not limited to, environmental samples such as soil, water, and flora. Yet other samples include laboratory samples, for example of engineered HA polypeptides designed and/or prepared by researchers. Other samples that have not been listed may also be applicable.

A wide variety of detection systems suitable for assaying HA polypeptide binding to inventive glycan arrays are known in the art. For example, HA polypeptides can be detectably labeled (directly or indirectly) prior to or after being contacted with the array; binding can then be detected by detection of localized label. In some embodiments, scanning devices can be utilized to examine particular locations on an array.

Alternatively or additionally, binding to arrayed glycans can be measured using, for example, calorimetric, fluorescence, or radioactive detection systems, or other labeling methods, or other methods that do not require labeling. In general, fluorescent detection typically involves directly probing the array with a fluorescent molecule and monitoring fluorescent signals. Alternatively or additionally, arrays can be probed with a molecule that is tagged (for example, with biotin) for indirect fluorescence detection (in this case, by testing for binding of fluorescently-labeled streptavidin). Alternatively or additionally, fluorescence quenching methods can be utilized in which the arrayed glycans are fluorescently labeled and probed with a test molecule (which may or may not be labeled with a different fluorophore). In such embodiments, binding to the array acts to squelch the fluorescence emitted from the arrayed glycan, therefore binding is detected by loss of fluorescent emission. Alternatively or additionally, arrayed glycans can be probed with a live tissue sample that has been grown in the presence of a radioactive substance, yielding a radioactively labeled probe. Binding in such embodiments can be detected by measuring radioactive emission.

Such methods are useful to determine the fact of binding and/or the extent of binding by HA polypeptides to inventive glycan arrays. In some embodiments of the invention, such methods can further be used to identify and/or characterize agents that interfere with or otherwise alter glycan-HA polypeptide interactions.

Methods described below may be of particular use in, for example, identifying whether a molecule thought to be capable of interacting with a carbohydrate can actually do so, or to identify whether a molecule unexpectedly has the capability of interacting with a carbohydrate.

The present invention also provides methods of using inventive arrays, for example, to detect a particular agent in a test sample. For instance, such methods may comprise steps of (1) contacting a glycan array with a test sample (e.g., with a sample thought to contain an HA polypeptide); and, (2) detecting the binding of any agent in the test sample to the array.

Yet further, binding to inventive arrays may be utilized, for example, to determine kinetics of interaction between binding agent and glycan. For example, inventive methods for determining interaction kinetics may include steps of (1) contacting a glycan array with the molecule being tested; and, (2) measuring kinetics of interaction between the binding agent and arrayed glycan(s).

The kinetics of interaction of a binding agent with any of the glycans in an inventive array can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same carbohydrate.

It will be appreciated, of course, that glycan binding by HA polypeptides in accordance with the invention can be evaluated on glycan samples or sources not present in an array format per se. For example, HA polypeptides in accordance with the invention can be bound to tissue samples and/or cell lines to assess their glycan binding characteristics. Appropriate cell lines include, for example, any of a variety of mammalian cell lines, particularly those expressing HA receptors containing umbrella topology glycans (e.g., at least some of which may be α2-6 sialylated glycans, and particularly long α2-6 sialylated glycans). In some embodiments, utilized cell lines express individual glycans with umbrella topology. In some embodiments, utilized cell lines express a diversity of glycans. In some embodiments, cell lines are obtained from clinical isolates; in some they are maintained or manipulated to have a desired glycan distribution and/or prevalence. In some embodiments, tissue samples and/or cell lines express glycans characteristic of mammalian upper respiratory epithelial cells.

Data Mining Platform

As discussed here, according to the present invention, HA polypeptides can be identified and/or characterized by mining data from glycan binding studies, structural information (e.g., HA crystal structures), and/or protein structure prediction programs.

The main steps involved in the particular data mining process utilized by the present inventors (and exemplified herein) are illustrated in FIG. 15. These steps involved operations on three elements: data objects, features, and classifiers. “Data objects” were the raw data that were stored in a database. In the case of glycan array data, the chemical description of glycan structures in terms of monosaccharides and linkages and their binding signals with different GBPs screened constituted the data objects. Properties of the data objects were “features.” Rules or patterns obtained based on the features were chosen to describe a data object. “Classifiers” were the rules or patterns that were used to either cluster data objects into specific classes or determine relationships between or among features. The classifiers provided specific features that were satisfied by the glycans that bind with high affinity to a GBP. These rules were of two kinds (1) features present on a set of high affinity glycan ligands, which can be considered to enhance binding, and (2) features that should not be present in the high affinity glycan ligands, which can be considered not favorable for binding.

The data mining platform utilized herein comprised software modules that interact with each other (FIG. 15) to perform the operations described above. The feature extractor interfaces to the CFG database to extract features, and the object-based relational database used by CFG facilitates the flexible definition of features.

Feature Extraction and Data Preparation

Representative features extracted from the glycans on the glycan array are listed in Table 6.

TABLE 6

Features extracted from the glycans on the glycan array. The features described in this table were used by the rule based classification algorithm to identify patterns that characterized binding to specific GBP.

| Features extracted | Feature Description |
|---|---|
| Monosaccharide level | |
| Composition | Number of hex, hexNAcs, dHex, sialic acids, etc [In FIG. 1, the composition is Hex = 5; HexNAc = 4]. Terminal composition is distinctly recorded [In FIG. 1, the terminal composition is Hex = 2; HexNAc = 2]. |
| Explicit Composition | Number of Glc, Gal, GlcNAc, Fuc, GalNAc, Neu5Ac, Neu5Gc, etc [In FIG. 1, the explicit composition is Man = 5; GlcNAc = 4]. Terminal explicit composition is explicitly recorded [In FIG. 1, the terminal explicit composition is Man = 2; GlcNAc = 2]. |
| Higher order features | |
| Pairs | Pair refers to a pair of monosaccharide, connected covalently by a linkage. The pairs are classified into two categories, regular [B] and terminal [T] to distinguish between the pair with one monosaccharide |

TABLE 6-continued

Features extracted from the glycans on the glycan array. The features described in this table were used by the rule based classification algorithm to identify patterns that characterized binding to specific GBP.

| Features extracted | Feature Description |
|---|---|
| | that terminates in the non reducing end [FIG. 16]. The frequency of the pairs were extracted as features |
| Triplets | Triplet refers to a set of three monosaccharides connected covalently by two linkages. We classify them into three categories namely regular [B], terminal [T] and surface [S] [FIG. 16]. The compositions of each category of triplets were extracted as features |
| Quadruplets | Similar to the triplet features, quadruplets features are also extracted, with four monosaccharides and their linkages [FIG. 16]. Quadruplets are classified into two varieties regular [B] and surface [S]. The frequencies of the different quadruplets were extracted as features |
| Clusters | In the case of surface triplets and quadruplets above, if the linkage information is ignored, we get a set of monosaccharide clusters, and their frequency of occurrence (composition) is tabulated. These features were chosen to analyze the importance of types of linkages between the monosaccharides. |
| Average Leaf Depth | As an indicator of the effective length of the probes, average depth of the reducing end of the tree is extracted as a glycan feature. In FIG. 16B, the leaf depths are 3, 4 and 3, and the average is 3.34 |
| Number of Leaves | As a measure of spread of the glycan tree, the number of non reducing monosaccharides is extracted as a feature. For FIG. 16B, the number of leaves is 3. For FIG. 1 it is 4. |
| GBP binding features | These features are obtained for all GBPs screened using the array |
| Mean signal per glycan | Raw signal value averaged over triplicate or quadruplicate [depending on array version] representation of the same glycan |
| Signal to Noise Ratio | Mean noise computed based on negative control [standardized method developed by CFG] to calculate signal to noise ratio [S/N] |

The rationale behind choosing these particular features shown was that glycan binding sites on GBPs typically accommodate di-tetra—saccharides. A tree based representation was used to capture the information on monosaccharides and linkages in the glycan structures (root of the tree at the reducing end). This representation facilitated the abstraction of various features including higher order features such as connected set of monosaccharide triplets, etc (FIG. 16). The data preparation involved generating a column-wise listing of all glycans in the glycan array along with abstracted features (Table 6) for each glycan. From this master table of glycans and their features, a subset is chosen for the rule based classification (see below) to determine specific patterns that govern the binding to a specific GBP or set of GBPs.

Classifiers

Different types of classifiers have been developed and used in many applications. They fall primarily into three main categories: Mathematical Methods, Distance Methods and Logic Methods. These different methods and their advantages and disadvantages are discussed in detail in Weiss & Indrukhya (Predictive data mining—A practical guide. Morgan Kaufmann, San Francisco, 1998). For this specific application we chose a method called Rule Induction, which falls under Logic Methods. The Rule Induction classifier generates patterns in form of IF-THEN rules.

One of the main advantages of the Logic Methods, and specifically classifiers such as the Rule Induction method that generate IF-THEN rules, is that the results of the classifiers can be explained more easily when compared to the other statistical or mathematical methods. This allows one to explore the structural and biological significance of the rule or pattern discovered. An example rule generated using the features described earlier (Table 6) is: IF A Glycan contains “Galb4GlcNAcb3Gal[B]” and DOES NOT contain “Fuca3GlcNAc[B]”, THEN the Glycan will bind with higher affinity to Galectin 3. The specific Rule Induction algorithm that was used in this case is the one developed by Weiss & Indurkya (Predictive data mining—A practical guide. Morgan Kaufmann, San Francisco, 1998.

Binding Levels

A threshold that distinguished low affinity and high affinity binding was defined for each of the glycan array screening data sets.

Nucleic Acids

In some embodiments, the present invention provides nucleic acids which encode an HA polypeptide or a characteristic or biologically active portion of an HA polypeptide. In other embodiments, the invention provides nucleic acids which are complementary to nucleic acids which encode an HA polypeptide or a characteristic or biologically active portion of an HA polypeptide.

In some embodiments, the invention provides nucleic acid molecules which hybridize to nucleic acids encoding an HA polypeptide or a characteristic or biologically active portion of an HA polypeptide. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In some embodiments, nucleic acids can be DNA or RNA, and can be single stranded or double-stranded. In some embodiments, inventive nucleic acids may include one or more non-natural nucleotides; in other embodiments, nucleic acids in accordance with the present invention include only natural nucleotides.

Antibodies to Polypeptides

The present invention provides antibodies to binding agent polypeptides in accordance with the present invention (e.g., HA polypeptides). These may be monoclonal or polyclonal and may be prepared by any of a variety of techniques known to those of ordinary skill in the art (e.g., see Harlow and Lane, 1988 Antibodies: A Laboratory Manual, Cold Spring Harbor Laboratory; incorporated herein by reference). For example, antibodies can be produced by cell culture techniques, including the generation of monoclonal antibodies, or via transfection of antibody genes into suitable bacterial or mammalian cell hosts, in order to allow for the production of recombinant antibodies.

Testing Binding Agents in Animal Models

The present invention provides methods for testing binding agents in accordance with the present invention (e.g., HA polypeptides, LSBAs, USBAs, UTSBAs, etc.) in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In some embodiments, an animal host used for the invention is a ferret. In particular, in some embodiments, an animal host is naïve to viral exposure or infection prior to administration of an inventive binding agent (optionally in an inventive composition). In some embodiments, the animal host is inoculated with, infected with, or otherwise exposed to virus prior to or concurrent with administration of an inventive binding agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or α2-6 glycans vs. a 2-3 glycans to the distribution found in the human respiratory tract. For example, it is contemplated that a ferret as an animal host may be more representative than a mouse when used as model of disease caused by influenza viruses in humans (Tumpey, et al. 2007 Science 315; 655-659; incorporated herein by reference). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey, et al. 2007 *Science* 315; 655-659; incorporated herein by reference). Virus transmission studies may be used to test inventive binding agent polypeptides (e.g., HA polypeptides). For example, inventive binding agents may be administered to a suitable animal host before, during or after virus transmission studies in order to determine the efficacy of said binding agent in blocking virus binding and/or infectivity in the animal host. Using information gathered from virus transmission studies in an animal host, one may predict the efficacy of a binding agent in blocking virus binding and/or infectivity in a human host.

Treatment

The present invention provides systems, compositions, and methods to treat (e.g., alleviate, ameliorate, relieve, delay onset of, inhibit progression of, reduce severity of, and/or reduce incidence of one or more symptoms or features of) and/or prevent influenza infection. In some embodiments, inventive binding agents such as those described herein may be used for a variety of therapeutic purposes, e.g., treating influenza infection and/or developing vaccines to immunize subjects against influenza infection.

A. Vaccination

In some embodiments, inventive binding agents in accordance with the invention (e.g., entities that bind to HA polypeptides and/or fragments, variants, and/or characteristic portions thereof; entities that bind to umbrella-topology glycans) may be utilized for prophylactic applications. In some embodiments, prophylactic applications involve systems and methods for preventing, inhibiting progression of, and/or delaying the onset of influenza infection.

In some embodiments, influenza vaccines are used to prevent and/or delay onset of infection by influenza. In some embodiments, vaccination is tailored to a particular HA polypeptide. For example, vaccine compositions may comprise H2 HA polypeptides and/or variants, fragments, and/or characteristic portions thereof. In some embodiments, it is desirable for vaccine compositions to comprise antigens that have a native conformation, mediate a protective response (e.g., complement activation, virus neutralization, etc.), and/or can induce a strong antibody response.

In some embodiments, interfering agents may be utilized for passive immunization (i.e., immunization wherein antibodies are administered to a subject). In some embodiments, influenza vaccines for passive immunization may comprise antibody interfering agents, such as those described herein. In some embodiments, passive immunization occurs when antibodies are transferred from mother to fetus during pregnancy. In some embodiments, antibodies are administered directly to an individual (e.g., by injection, orally, etc.).

The present invention provides influenza vaccines for active immunization (i.e., immunization wherein microbes, proteins, peptides, epitopes, mimotopes, etc. are administered to a subject). In some embodiments, influenza vaccines may comprise one or more interfering agents and/or binding agents, as described herein.

In some embodiments, vaccines comprise at least one HA polypeptide (and/or to variants, fragments, and/or characteristic portions thereof), e.g., any of the HA polypeptides, variants, fragments, characteristic portions, and/or combinations thereof described herein. In some embodiments, vaccines comprise H2 HA polypeptides (and/or to variants, fragments, and/or characteristic portions thereof). In some embodiments, vaccines comprise HA polypeptides having one or more of the following: arginine at Residue 137, threonine at Residue 193, leucine at Residue 226, and/or serine at Residue 228. In some embodiments, vaccines comprise HA polypeptides having each of the following: arginine at Residue 137, threonine at Residue 193, leucine at Residue 226, and/or serine at Residue 228. In some embodiments, vaccines comprise live active virus particles comprising one or more of any HA polypeptide described herein, live attenuated virus particles comprising one or more of any HA polypeptide described herein, virus-like particles (VLPs) comprising one or more of any HA polypeptide described herein, subunit vaccines comprising one or more of any HA polypeptide described herein, and/or combinations thereof.

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on the internet (available through the world wide web at niaid.nih.gov/daids/vaccine/pdf/compendium.pdf). See also Allison (1998, *Dev. Biol. Stand.,* 92:3-11; incorporated herein by reference), Unkeless et al. (1998, *Annu. Rev. Immunol.,* 6:251-281; incorporated herein by reference), and Phillips et al. (1992, *Vaccine,* 10:151-158; incorporated herein by reference). Hundreds of different adjuvants are known in the art and could be employed in the practice of the present invention. Exemplary adjuvants that can be utilized in accordance with the invention include, but are not limited to, cytokines, aluminum salts (e.g., aluminum hydroxide, aluminum phosphate, etc.; Baylor et al., *Vaccine,* 20:S18, 2002; incorporated herein by reference), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, *Immunology and Immunopharmacology of bacterial endotoxins*, Plenum Publ. Corp., NY, p 407, 1986; incorporated herein by reference); exotoxins such as cholera toxin, *E. coli* heat labile toxin, and *pertussis* toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, saponins (e.g., QS21, Ghochikyan et al., *Vaccine,* 24:2275, 2006; incorporated herein by reference), squalene, tetrachlorodecaoxide, CPG 7909 (Cooper et al., *Vaccine,* 22:3136, 2004; incorporated herein by reference), poly[di(carboxylatophenoxy)phosphazene] (PCCP; Payne et al., *Vaccine,* 16:92, 1998; incorporated herein by reference), interferon-γ (Cao et al., *Vaccine,* 10:238, 1992; incorporated herein by reference), block copolymer P1205 (CRL1005; Katz et al., *Vaccine,* 18:2177, 2000; incorporated herein by reference), interleukin-2 (IL-2; Mbwuike et al., *Vaccine,* 8:347, 1990; incorporated herein by reference), polymethyl methacrylate (PMMA; Kreuter et al., *J. Pharm. Sci.,* 70:367, 1981; incorporated herein by reference), etc.

B. Therapy

The present invention provides systems and methods for treating patients suffering from, susceptible to, and/or displaying symptoms of influenza infection. In some embodiments, the invention provides systems and methods useful for stratifying patients suffering from, susceptible to, and/or displaying symptoms of influenza infection.

In some embodiments, inventive binding agents in accordance with the invention may be utilized for therapeutic applications.

In some embodiments, therapeutic applications comprise administering a therapeutically effective amount of at least one binding agent in accordance with the invention to a subject in need thereof. In some embodiments, administration of binding agents to a subject may alleviate, ameliorate, relieve, delay onset of, inhibit progression of, reduce severity of, and/or reduce incidence of one or more signs, symptoms, and/or features of influenza infection.

In some embodiments, administration of binding agents reduces the level of influenza virions circulating in a subject (e.g., influenza virions that are capable of infecting new cells). In some embodiments, administration of binding agents reduces the level of influenza virions circulating in a subject by about 10%, about 20%, about 30%, about 40%, about 50%, about 60%, about 70%, about 80%, about 90%, about 95%, about 99%, or about 100% relative to non-treated controls.

In some embodiments, binding agents may be used in vitro to reduce viral load in a subject. For reducing viral load of a body component, particularly a body component of a patient infected with influenza, a patient's blood is passed through a device comprising binding agents bound to a surface or solid support for capturing influenza virions (see, for example, U.S. Pat. Nos. 5,698,390 and 4,692,411; both of which are incorporated herein by reference). Various other devices found in the literature can be used with the subject antibodies to achieve a similar result. A body component can be a biological fluid (e.g., blood, serum, etc.), a tissue, an organ, such as the liver, and the like.

In some embodiments, the "level of influenza virions circulating in a subject" refers to an absolute number of virions circulating in a subject. In some embodiments, the "level of influenza virions circulating in a subject" refers to the number of virions per unit volume (e.g., milliliter, liter, etc.) of the subject's blood. In some embodiments, the "level of influenza virions circulating in a subject" refers to viral load.

In some embodiments, administration of binding agents inhibits binding of virus to HA receptors. In some embodiments, administration of binding agents inhibits binding of virus to at least one HA receptor by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents kills and/or inactivates influenza virions in a subject. In some embodiments, administration of influenza antibodies kills and/or inactivates about 10%, about 20%, about 30%, about 40%, about 50%, about 60%, about 70%, about 80%, about 90%, about 95%, about 99%, or about 100% of influenza virions in a subject relative to non-treated controls.

In some embodiments, administration of binding agents inhibits virus-mediated fusion with a target cell. In some embodiments, administration of binding agents inhibits virus-mediated fusion with a target cell by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents inhibits conformational changes of one or more proteins associated with virus entry. In some embodiments, administration of binding agents inhibits conformational changes of one or more proteins associated with virus entry by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents results in conformational changes in HA polypeptides and/or HA receptors. For example, administered interfering agents and/or binding agents may bind to HA polypeptides and/or HA receptors, thereby sterically blocking the HA polypeptide's and/or HA receptors' ability to recognize and/or interact with one another. In some embodiments, administered binding agents may bind to HA polypeptides and/or HA receptors, thereby changing the three-dimensional conformation of the HA polypeptides and/or HA receptors in such a way that renders HA polypeptides and/or HA receptors incapable of recognizing one another.

In some embodiments, treatment and/or vaccination regimens are particularly tailored for the individual being treated and/or vaccinated. The present invention provides systems, compositions, and methods useful for determining whether a patient is infected with H2 HA influenza or non-H2 HA influenza. Such methods can be utilized to stratify patients into treatment and/or vaccination categories. In some embodiments, such methods may be advantageous because the treatment and/or vaccination is tailored to the particular individual being treated and/or vaccinated. To give but one particular example, if a patient is classified as being infected with H2 HA influenza, therapies that are useful for treatment of H2 HA influenza can be administered to the patient, and therapies that are not useful for treatment of H2 HA influenza will not be administered. This avoids or reduces the risk of adverse reactions from administering therapeutics that are not needed. Such methods eliminate the expense of treating and/or vaccinating patients who would not benefit from such treatment and/or vaccination.

C. Pharmaceutical Compositions

In some embodiments, the present invention provides for pharmaceutical compositions including inventive binding agents (e.g., HA polypeptides, LSBAs, UTBAs, UTBSAs, etc.) and/or related entities. For example, in some embodiments, binding agent polypeptide(s) (e.g., HA polypeptides), nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in inventive pharmaceutical compositions. In some embodiments, inventive binding agents that are not polypeptides, e.g., that are small molecules, umbrella topology glycans and mimics thereof, carbohydrates, aptamers, polymers, nucleic acids, etc., are included in pharmaceutical compositions.

The invention encompasses treatment of influenza infections by administration of such inventive pharmaceutical compositions. In some embodiments, inventive pharmaceutical compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to inventive binding agents prior to, during, or after administration of inventive pharmaceutical compositions. In some embodiments, subjects having such antibodies are not administered pharmaceutical compositions comprising inventive binding agents. In some embodiments, an appropriate dose of pharmaceutical composition and/or binding agent is selected based on detection (or lack thereof) of such antibodies.

In some embodiments, selection of a particular subject for treatment, particular binding agent or composition for administration, and/or particular dose or regimen for administration, is memorialized, for example in a written, printed, or electronic storage form.

Inventive compositions may be administered prior to or after development of one or more symptoms of influenza infection.

The invention encompasses treatment and/or prevention (e.g., vaccination) of influenza infections by administration of agents and/or compositions described herein. In some embodiments, treatment of influenza infections according to the present invention is accomplished by administration of a vaccine. To date, although significant accomplishments have been made in the development of influenza vaccines, there is room for further improvement. The present invention provides vaccines comprising inventive binding agents (e.g., HA polypeptides, particularly H2 HA polypeptides, LSBAs, UTBAs, UTBSAs, etc.), and particularly comprising binding agents that bind to umbrella glycans (e.g., α2-6 linked umbrella glycans such as, for example, long α2-6 sialylated glycans). In some embodiments, a composition is substantially free of agents that preferentially bind to non-umbrella topology glycans. In some such embodiments, pharmaceutical compositions contain not more than 50%, 40%, 30%, 20%, 10%, 5%, or 1% of an agent that binds to HA receptor glycans other than umbrella topology glycans.

To give but one example, the H2N2 influenza subtype stopped circulating in humans by 1968, however H2 subtype viruses are occasionally isolated from swine and avian species. The circulation of avian H2 strains in domestic birds and pigs increase the risk of human exposure to these viruses and reintroduction of the viruses to the human population. Such a reintroduction could lead to a significant global health threat given the lack of pre-existing immunity in a huge subset of the human population born after 1968. The present invention provides, among other things, vaccines comprising H2 HA polypeptides for treatment and/or prevention of influenza infections.

In some embodiments, the present invention provides for vaccines and the administration of these vaccines to a human subject (e.g., to an individual suffering from or susceptible to influenza infection). In some embodiments, vaccines are compositions comprising one or more of the following: (1) inactivated virus, (2) live attenuated influenza virus, for example, replication-defective virus, (3) inventive binding agent (e.g., HA polypeptides and/or polypeptide variants, LSBAs, UTBAs, UTBSAs, etc.)), (4) nucleic acid encoding binding agent polypeptide (e.g., HA polypeptide) or characteristic or biologically active portion thereof, (5) DNA vector that encodes inventive binding agent polypeptide (e.g., HA polypeptide) or characteristic or biologically active portion thereof, and/or (6) expression system, for example, cells expressing one or more influenza proteins to be used as antigens, and/or virus-like particles.

Thus, in some embodiments, the present invention provides inactivated flu vaccines. In some embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., *Textbook of Influenza*, Blackwell Science, Malden, Mass., 1998). To assess the potency of the vaccine, the single radial immunodiffusion (SRD) test can be used (Schild et al., *Bull. World Health Organ.,* 52:43-50 & 223-31, 1975; Mostow et al., *J. Clin. Microbiol.,* 2:531, 1975; incorporated herein by reference). In some embodiments, the present invention provides virus-like particles (VLPs) that are useful for vaccines. In general, VLPs comprise multiple copies of a protein antigen that, when assembled together, mimic the conformation of a native virus. In some embodiments, VLPs contain repetitive high density displays of influenza virus surface proteins (e.g., HA polypeptides in accordance with the present invention) which present conformational epitopes that can elicit strong T cell and/or B cell immune responses. Since VLPs do not contain any viral genetic material, they may be safer than attenuated viruses in vaccine compositions. VLPs can be produced in a variety of cell culture systems including mammalian cell lines, insect cell lines, yeast, plant cells, etc. For a general discussion of VLPs, see, e.g., published PCT applications WO 02/000885, WO 05/020889, WO 06/108226, WO 07/130327, WO 07/130330, WO 08/005777, WO 08/040060, WO 08/054535, WO 08/061243, WO 08/094197, WO 08/094200, WO 08/148104, WO 09/009876, WO 09/012489, WO 10/006452, and US patent application publication 2005/0009008, all of which are incorporated herein by reference.

In some embodiments, a VLP in accordance with the invention is a specialized VLP called a lipoparticle. In general, lipoparticles are stable, highly purified, homogeneous VLPs that are engineered to contain high concentrations of a conformationally intact membrane protein of interest. In some embodiments, lipoparticles in accordance with the present invention contain influenza envelope proteins and/or other influenza antigens.

The present invention also provides live, attenuated flu vaccines, and methods for attenuation are well known in the art. In some embodiments, attenuation is achieved through the use of reverse genetics, such as site-directed mutagenesis.

In some embodiments, influenza virus for use in vaccines is grown in eggs, for example, in embryonated hen eggs, in which case the harvested material is allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

In some embodiments, vaccines further comprise one or more adjuvants. Any adjuvant may be used in accordance with the present invention. A large number of adjuvants are known; a useful compendium of many such compounds is prepared by the National Institutes of Health and is available through the world wide web at niaid.nih.gov/daids/vaccine/pdf/compendium.pdf. See also Allison (1998, *Dev. Biol. Stand.,* 92:3-11; incorporated herein by reference), Unkeless et al. (1998, *Annu. Rev. Immunol.,* 6:251-281; incorporated herein by reference), and Phillips et al. (1992, *Vaccine,* 10:151-158; incorporated herein by reference). Hundreds of different adjuvants are known in the art and could be employed in the practice of the present invention. For example, aluminum salts (e.g., aluminum hydroxide, aluminum phosphate, etc., Baylor et al., *Vaccine,* 20:S18, 2002) and monophosphoryl lipid A (MPL; Ribi et al., (1986, *Immunology and Immunopharmacology of bacterial endotoxins*, Plenum Publ. Corp., NY, p 407, 1986) can be used as adjuvants in human vaccines. Alternatively or additionally, exemplary adjuvants that can be utilized in accordance with the invention include cytokines, calcium phosphate, microbial adjuvants (e.g., immunomodulatory DNA sequences that include CpG motifs; endotoxins such as monophosphoryl lipid A (Ribi et al., 1986, Immunology and Immunopharmacology of bacterial endotoxins, Plenum Publ. Corp., NY, p 407, 1986; incorporated herein by reference); exotoxins such as cholera toxin, *E. coli* heat labile toxin, and *pertussis* toxin; muramyl dipeptide, etc.); oil-emulsion and emulsifier-based adjuvants (e.g., Freund's Adjuvant, SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); polymers (e.g., polyphosphazenes; described in U.S. Pat. No. 5,500,161, which is incorporated herein by reference), Q57, squalene, and/or tetrachlorodecaoxide.

Alternatively or additionally, new compounds are currently being tested as adjuvants in human vaccines, such as MF59 (Chiron Corp., available through the world wide web at chiron.com/investors/pressreleases/2005/051028), CPG 7909 (Cooper et al., *Vaccine,* 22:3136, 2004; incorporated herein by reference), and saponins, such as QS21 (Ghochikyan et al., *Vaccine,* 24:2275, 2006; incorporated herein by reference).

Additionally, some adjuvants are known in the art to enhance the immunogenicity of influenza vaccines, such as poly[di(carboxylatophenoxy)phosphazene] (PCCP; Payne et al., *Vaccine,* 16:92, 1998; incorporated herein by reference), interferon-γ (Cao et al., *Vaccine,* 10:238, 1992; incorporated herein by reference), block copolymer P1205 (CRL1005; Katz et al., *Vaccine,* 18:2177, 2000; incorporated herein by reference), interleukin-2 (IL-2; Mbwuike et al., *Vaccine,* 8:347, 1990; incorporated herein by reference), and polymethyl methacrylate (PMMA; Kreuter et al., *J. Pharm. Sci.,* 70:367, 1981; incorporated herein by reference).

In some embodiments, pharmaceutical compositions do not include adjuvants (e.g., provided compositions are essentially free of adjuvants). In some embodiments, pharmaceutical compositions do not include an alum adjuvant (e.g., provided compositions are essentially free of alum).

In addition to vaccines, the present invention provides other therapeutic compositions useful in the treatment and/or vaccination of viral infections. In some embodiments, treatment and/or vaccination is accomplished by administration of an agent that interferes with expression or activity of an HA polypeptide.

In some embodiments, the present invention provides pharmaceutical compositions comprising antibodies or other agents related to provided polypeptides. For example, the invention provides compositions containing antibodies recognize virus particles containing a particular HA polypeptide (e.g., an HA polypeptide that binds to umbrella glycans), nucleic acids (such as nucleic acid sequences complementary to HA sequences, which can be used for RNAi), glycans that compete for binding to HA receptors, small molecules or glycomometics that compete the glycan-HA polypeptide interaction, or any combination thereof. In some embodiments, collections of different agents, having diverse structures are utilized. In some embodiments, therapeutic compositions comprise one or more multivalent agents. In some embodiments, treatment comprises urgent administration shortly after exposure or suspicion of exposure.

In general, a pharmaceutical composition will include a therapeutic agent in addition to one or more inactive agents such as a sterile, biocompatible carrier including, but not limited to, sterile water, saline, buffered saline, or dextrose solution. Alternatively or additionally, a composition may comprise a pharmaceutically acceptable excipient, which, as used herein, includes any and all solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, as suited to the particular dosage form desired. Remington's *The Science and Practice of Pharmacy,* $21^{st}$ Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component of the pharmaceutical composition, its use is contemplated to be within the scope of this invention.

In some embodiments, the therapeutic agent present in an inventive pharmaceutical composition will consist of one or more binding agents as described herein. In some embodiments, an inventive pharmaceutical composition contains a binding agent (e.g., an HA polypeptide, LSBA, UTBA, UTSBA, etc.) that binds to umbrella topology glycans (and/or to umbrella topology glycan mimics). In some such embodiments, the inventive composition is substantially free of related agents (e.g., of other HA polypeptides, etc.) that do not bind to umbrella-topology glycans. In some such embodiments, the inventive pharmaceutical compositions contains not more than 50%, 40%, 30%, 20%, 10%, 5%, or 1% of an agent that binds to HA receptor glycans other than umbrella topology glycans.

In some embodiments, a pharmaceutical composition will include a therapeutic agent that is encapsulated, trapped, or bound within a lipid vesicle, a bioavailable and/or biocompatible and/or biodegradable matrix, or other microparticle.

In some embodiments, a provided pharmaceutical composition will include a binding agent (e.g., an HA polypeptide, LSBA, UTBA, UTSBA, etc.) that is not aggregated. For example, in some embodiments, less than 1%, 2%, 5%, 10%, 20%, or 30%, by dry weight or number, of the binding agent is present in an aggregate.

In some embodiments, a provided pharmaceutical composition will include a binding agent (e.g., an HA polypeptide, LSBA, UTBA, UTSBA, etc.) that is not denatured. For example, in some embodiments, less than 1%, 2%, 5%, 10%, 20%, or 30%, by dry weight or number, of the UTSBA administered is denatured.

In some embodiments, a provided pharmaceutical composition will include a binding agent (e.g., an HA polypeptide, LSBA, UTBA, UTSBA, etc.) that is not inactive. For example, in some embodiments, less than 1%, 2%, 5%, 10%, 20%, or 30%, by dry weight or number, of the UTSBA administered is inactive.

In some embodiments, inventive pharmaceutical compositions are formulated to reduce immunogenicity of provided binding agents. For example, in some embodiments, a provided binding agent is associated with (e.g., bound to) an agent, such as polyethylene glycol and/or carboxymethyl cellulose, that masks its immunogenicity. In some embodiments, a provided binding agent has additional glycosylation that reduces immunogenicity.

Pharmaceutical compositions of the present invention may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans. In some embodiments, inventive pharmaceutical compositions and/or binding agents are administered in combination with one or more of an anti-viral agent (e.g., Oseltamivir [tamiflu], Zanamavir [Relenza], etc.) and/or a sialidase.

Pharmaceutical compositions may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Pharmaceutical compositions are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and/or vaccinated and the severity of the disorder; the activity of the specific vaccine composition employed; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions of the present invention may be administered by any route. In some embodiments, pharmaceutical compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In general, the most appropriate route of administration will depend upon a variety of factors including the nature of the agent being administered (e.g., its stability upon administration), the condition of the subject (e.g., whether the subject is able to tolerate a particular mode of administration), etc. In specific embodiments, pharmaceutical compositions may be administered intranasally. In specific embodiments, pharmaceutical compositions may be administered by intratracheal instillation. In specific embodiments, pharmaceutical compositions may be administered by bronchial instillation. In specific embodiments, pharmaceutical compositions may be administered by inhalation. In specific embodiments, pharmaceutical compositions may be administered as a nasal spray. In specific embodiments, pharmaceutical compositions may be administered mucosally. In specific embodiments, pharmaceutical compositions may be administered orally. In specific embodiments, pharmaceutical compositions may be administered by intravenous injection. In specific embodiments, pharmaceutical compositions may be administered by intramuscular injection. In specific embodiments, pharmaceutical compositions may be administered by subcutaneous injection. At present the oral or nasal spray or aerosol route (e.g., by inhalation) is most commonly used to deliver therapeutic agents directly to the lungs and respiratory system. However, the invention encompasses the delivery of the inventive composition by any appropriate route taking into consideration likely advances in the sciences of drug delivery.

In some embodiments, preparations for inhaled or aerosol delivery comprise a plurality of particles. In some embodiments, such preparations have a mean particle size of about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, inventive compositions are administered as drops to the nasal or buccal cavity. In some embodiments, a dose may comprise a plurality of drops (e.g., 1-100, 1-50, 1-20, 1-10, 1-5, etc.)

In some embodiments, inventive compositions are administered using a device that delivers a metered dosage of composition (e.g., of binding agent).

Suitable devices for use in delivering intradermal pharmaceutical compositions described herein include short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662; all of which are incorporated herein by reference. Intradermal compositions may also be administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537; all of which are incorporated herein by reference. Also suitable are ballistic powder/particle delivery devices which use compressed gas to accelerate vaccine in powder form through the outer layers of the skin to the dermis. Additionally, conventional syringes may be used in the classical mantoux method of intradermal administration.

General considerations in the formulation and manufacture of pharmaceutical agents may be found, for example, in *Remington's Pharmaceutical Sciences,* $19^{th}$ ed., Mack Publishing Co., Easton, Pa., 1995.

Inventive pharmaceutical compositions may be administered in any dose appropriate to achieve a desired outcome. In some embodiments, the desired outcome is reduction in intensity, severity, and/or frequency, and/or delay of onset of one or more symptoms of influenza infection.

In some embodiments, inventive pharmaceutical compositions are formulated to administer a dose of binding agent effective to compete with influenza HA for binding to umbrella topology glycans. In some embodiments, such binding by influenza HA is reduced after administration of one or more doses of an inventive composition as compared with its level absent such administration. In some embodiments, inventive pharmaceutical compositions are formulated to administer a dose of binding agent effective to saturate at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more than 99% or more HA binding sites (e.g., HA binding sites containing umbrella topology glycans) present in the subject (e.g., in the respiratory tract of the subject) receiving the composition.

In some embodiments, pharmaceutical compositions may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of a therapeutic agent per subject body weight per day to obtain a desired therapeutic effect. A desired dosage may be delivered to a subject only once. A desired dosage may be delivered more than three times per day, three times per day, two times per day, once per day, every other day, every third day, every week, every two weeks, every three weeks, every four weeks, every two months, every six months, every twelve months, every two years, every three years, every four years, every five years, every 10 years, or every 20 years. In some embodiments, the desired dosage may be delivered using multiple administrations (e.g., two, three, four, five, six, seven, eight, nine, ten, eleven, twelve, thirteen, fourteen, fifteen, or more administrations).

It will be appreciated that compositions in accordance with the present invention can be employed in combination therapies. The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an agent useful for treating, preventing, and/or delaying the onset of influenza infection may be administered concurrently with another agent useful for treating, preventing, and/or delaying the onset of influenza infection), or they may achieve different effects (e.g., control of any adverse effects). The invention encompasses delivery of pharmaceutical compositions in combination with agents that may improve their bioavailability, reduce and/or modify their metabolism, inhibit their excretion, and/or modify their distribution within the body.

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In general, it is expected that agents utilized in combination with be utilized at levels that do not exceed the levels at which they are utilized individually. In some embodiments, the levels utilized in combination will be lower than those utilized individually.

In some embodiments, pharmaceutical compositions are administered in combination with one or more of an anti-viral agent (e.g., Oseltamivir [tamiflu], Zanamavir [Relenza], etc.) and/or a sialidase.

Diagnostics/Kits

The present invention provides kits for detecting binding agents (e.g., HA polypeptides, LSBAs, UTBAs, UTSBAs, etc), and particular for detecting binding agents with particular glycan binding characteristics (e.g., binding to umbrella glycans, to α2-6 sialylated glycans, to long α2-6 sialylated glycans, etc.) in pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. The present invention also provides kits for detecting binding agents (e.g., HA polypeptides, LSBAs, UTBAs, UTSBAs, etc) of interest in environmental samples, including, but not limited to, soil, water, and flora. Other samples that have not been listed may also be applicable.

In some embodiments, the present invention provides kits for detecting HA polypeptides as described herein whether or not such polypeptides are binding agents.

In some embodiments, inventive kits may include one or more agents that specifically detect binding agents (e.g., HA polypeptides, LSBAs, UTBAs, UTSBAs, etc) with particular glycan binding characteristics. Such detecting agents may include, for example, antibodies that specifically recognize certain binding agents (e.g., binding agents that bind to umbrella glycans and/or to α2-6 sialylated glycans and/or to long α2-6 sialylated glycans), which can be used to specifically detect such binding agents by ELISA, immunofluorescence, and/or immunoblotting.

Antibodies that bind to HA polypeptides (e.g., to provided HA polypeptides such as HA polypeptide variants) can also be used in virus neutralization tests, in which a sample is treated with antibody specific to HA polypeptides of interest, and tested for its ability to infect cultured cells relative to untreated sample. If the virus in that sample contains such HA polypeptides, the antibody will neutralize the virus and prevent it from infecting the cultured cells. Alternatively or additionally, such antibodies can also be used in HA-inhibition tests, in which the HA protein is isolated from a given sample, treated with antibody specific to a particular HA polypeptide or set of HA polypeptides, and tested for its ability to agglutinate erythrocytes relative to untreated sample. If the virus in the sample contains such an HA polypeptide, the antibody will neutralize the activity of the HA polypeptide and prevent it from agglutinating erythrocytes (Harlow & Lane, Antibodies: A Laboratory Manual, CSHL Press, 1988; available through the world wide web at who.int/csr/resources/publications/influenza/WHO_CDS_CSR_NCS_2002_5/en/index; available through the world wide web at who.int/csr/disease/avian influenza/guidelines/labtests/en/index). In other embodiments, such agents may include nucleic acids that specifically bind to nucleotides that encode particular HA polypeptides and that can be used to specifically detect such HA polypeptides by RT-PCR or in situ hybridization (available through the world wide web at who.int/csr/resources/publications/influenza/WHO_CDS_CSR_NCS_2002_5/en/index; available through the world wide web at who.int/csr/disease/avian_influenza/guidelines/labtests/en/index). In some embodiments, nucleic acids which have been isolated from a sample are amplified prior to detection. In some embodiments, diagnostic reagents can be detectably labeled.

The present invention also provides kits containing reagents according to the invention for the generation of influenza viruses and vaccines. Contents of the kits include, but are not limited to, expression plasmids containing HA nucleotides (or characteristic or biologically active portions) encoding HA polypeptides of interest (or characteristic or biologically active portions). Alternatively or additionally, kits may contain expression plasmids that express HA polypeptides of interest (or characteristic or biologically active portions). Expression plasmids containing no virus genes may also be included so that users are capable of incorporating HA nucleotides from any influenza virus of interest. Mammalian cell lines may also be included with the kits, including but not limited to, Vero and MDCK cell lines. In some embodiments, diagnostic reagents can be detectably labeled.

In some embodiments, kits for use in accordance with the present invention may include, a reference sample, instructions for processing samples, performing the test, instructions for interpreting the results, buffers and/or other reagents necessary for performing the test. In some embodiments the kit can comprise a panel of antibodies.

In some embodiments of the present invention, glycan arrays, as discussed above, may be utilized as diagnostics and/or kits.

In some embodiments, inventive glycan arrays and/or kits are used to perform dose response studies to assess binding of HA polypeptides to umbrella glycans at multiple doses (e.g., as described herein). Such studies give particularly valuable insight into the binding characteristics of tested HA polypeptides, and are particularly useful to assess specific binding. Dose response binding studies of this type find many useful applications. To give but one example, they can be helpful in tracking the evolution of binding characteristics in a related series of HA polypeptide variants, whether the series is generated through natural evolution, intentional engineering, or a combination of the two.

In some embodiments, inventive glycan arrays and/or kits are used to induce, identify, and/or select binding agents (e.g., HA polypeptides, and/or HA polypeptides such as HA polypeptide variants) having desired binding characteristics. For instance, in some embodiments, inventive glycan arrays and/or kits are used to exert evolutionary (e.g., screening and/or selection) pressure on a population of polypeptide binding agents (e.g., HA polypeptides).

The present invention provides kits for administration of inventive pharmaceutical compositions. For example, in some embodiments, the invention provides a kit comprising at least one dose of a binding agent. In some embodiments, the invention provides a kit comprising an initial unit dose and a subsequent unit dose of a binding agent. In some such embodiments, the initial unit dose is greater than the subsequent unit dose or wherein the two doses are equal.

In some embodiments, inventive kits (particularly those for administration of inventive pharmaceutical compositions) comprise at least one component of a delivery device, e.g., an inhaler. In some such embodiments, the invention provides a kit comprising at least one component of a delivery device, e.g., an inhaler and a dose of an of a binding agent.

In some embodiments, provided kits comprise instructions for use.

EXEMPLIFICATION

Example 1

H2N2 HA Variants

The 20th century witnessed three influenza pandemics: the Spanish flu of 1918 (H1N1), the Asian flu of 1957-58 (H2N2) and the Hong Kong flu of 1967-68 (H3N2). Among these subtypes the H1N1 and H3N2 continue to circulate in the human population leading to epidemic outbreaks annually and the H1N1 subtype was responsible for the 2009 'swine flu' pandemic (2009 H1N1). The H2N2 subtype had stopped circulating in humans by 1968, however H2 subtype viruses are occasionally isolated from swine and avian species. The circulation of avian H2 strains in domestic birds and pigs increase the risk of human exposure to these viruses and reintroduction of the viruses to the human population. Such a reintroduction may pose a significant global health threat given the lack of pre-existing immunity in a huge subset of the human population born after 1968.

One of the main steps in the evolution of a pandemic influenza virus is the acquisition of genetic changes that enable it to adapt to the human host in order to replicate efficiently and transmit rapidly resulting in widespread and sustained disease in humans. An important first step in the host infection by the virus is the binding of the viral surface glycoprotein hemagglutinin (HA) to sialylated glycan receptors, complex glycans terminated by N-acetylneuraminic acid (Neu5Ac) expressed on the host cell surface. Glycans terminating in Neu5Ac that is $\alpha2\rightarrow6$-linked to the penultimate sugar are predominantly expressed in human upper respiratory epithelia and serve as receptors for human-adapted influenza A viruses (henceforth referred to as human receptors). On the other hand, glycans terminating in Neu5Ac that is $\alpha2\rightarrow3$-linked to the penultimate sugar residue, serve as receptors for the avian-adapted influenza viruses (henceforth referred to as avian receptors).

The molecular interactions of HA with avian and human receptors have been captured using a topology-based definition of glycan receptors. Glycan array platforms comprised of representative avian and human receptors have been widely employed to study the glycan receptor binding of HAs and whole viruses. The relative binding affinities of recombinantly expressed HAs from avian—(such as H1N1 and H5N1) and human-adapted (such as H1N1 and H3N2) viruses to avian and human receptors have been quantified by analyzing these HAs (or whole viruses) in a dose-dependent manner on glycan array platforms. Furthermore, the glycan array binding properties of the HAs have been shown to correlate with their binding to physiological glycan-receptors in human respiratory tissues. It has been shown that the human receptor-binding affinity of H1N1 HAs correlated with the efficiency of airborne viral transmission in the ferret animal model, which is an established model to evaluate viral transmissibility in humans. Such a relationship has yet to be shown for the H2N2 subtype.

Previous structural and biochemical studies have provided insights into interactions of the receptor binding site (RBS) of HA with avian and human receptors for both wild type (WT) and mutant forms of HA derived from the 1957-58 H2N2 pandemic strains. However, it has been recently demonstrated that changes in the interactions between amino acids within and proximal to the RBS, arising from substitutions due to antigenic drift or reassortment, have profound effects on HA-glycan interactions which in turn influences the glycan binding affinity of HA. This observation is particularly relevant to HA from recent avian-H2 strains that have diverged considerably in sequence compared to the HA sequence of the pandemic H2N2 strains. Therefore in order to monitor changes in the recent avian H2-subtype viruses that would possibly lead to their human-adaptation, it is important to understand the mutations in their HA that would confer human receptor-binding affinity that is quantitatively in the same range as that of HA from the 1957-58 human-adapted H2N2 pandemic viruses.

In the present example, we systematically analyzed the effects of mutations in the glycan RBS of pandemic and recent avian H2N2 HAs on their respective glycan-binding specificities. The HA from a representative 1957-58 pandemic H2N2 strain, A/Albany/6/58 (Alb58), was chosen as a reference human-adapted HA. The HA from a representative avian H2N2 virus, A/Chicken/Pennsylvania/2004 (CkPA04), which is among the most recent strains isolated from birds was also evaluated in this study. We first characterized the glycan receptor-binding affinity and human respiratory tissue binding properties of these avian- and human-adapted H2N2 HAs. The glycan receptor-binding affinity of HA is quantitatively defined using an apparent binding constant $K_d'$ that takes into account the cooperativity and avidity in the multivalent HA-glycan interactions as described previously. Next, using homology-based structural models of Alb58 HA-human receptor and CkPA04 HA-avian receptor complexes we analyzed the RBS of these HAs and designed and evaluated mutations in CkPA04 HA that would make its human receptor binding affinity in the same range as that of Alb58 HA.

Characterization of Glycan Receptor-Binding Specificity of Alb58 HA.

Figure 5A:
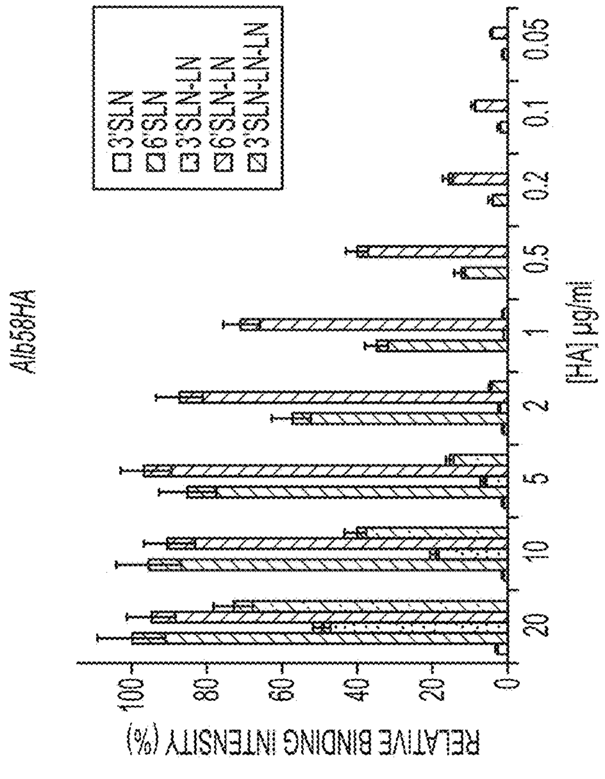
FIGS. 5A-B show exemplary glycan receptor-binding specificity of Alb58 HA.
Figure 5B:
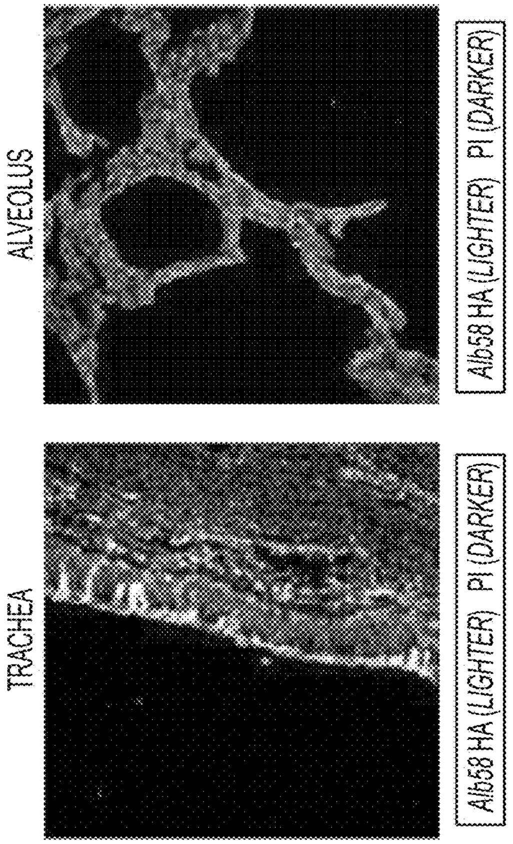

We have previously developed a dose-dependent glycan array binding assay to quantitatively characterize glycan receptor binding affinity of HA by calculating an apparent binding constant Kd'. Alb58 HA was recombinantly expressed and analyzed using this assay. Alb58 HA bound with high affinity to the representative human receptors, 6'SLN (Kd'~35 pM) and 6'SLN-LN (Kd'~5 pM) (FIG. 5A). Notably, the binding affinity of Alb58 HA to 6'SLN-LN is in the same range as that of the pandemic H1N1 (A/South Carolina/1/1918 or SC18) HA. However unlike SC18 HA, surprisingly, Alb58 HA also showed substantial binding to the representative avian receptors 3'SLN-LN (Kd'~1.5 nM) and 3'SLN-LN-LN (Kd'~1 nM) on the glycan array (FIG. 5A). Staining of Alb58 HA on human upper respiratory tracheal tissue sections revealed extensive binding of the protein to the apical side (FIG. 5B) and thus correlated with its high affinity binding to human receptors. Additionally, the substantial α2→3 sialylated glycan binding of Alb58 observed in the glycan array assay was also reflected in its binding to the human deep lung alveolar tissue (FIG. 5B) that predominantly expresses these glycans.

Previous studies have pointed to the roles played by the amino acids in positions 226 and 228 in the RBS of H2N2 HAs in governing the glycan receptor binding specificity. The observation includes the fact that HA from most human H2N2 isolates has Leu226 and Ser228 within its RBS, whereas HA from most avian H2 isolates has Gln226 and Gly228. To understand the roles of these residues on the quantitative glycan receptor binding affinity of Alb58 HA, three mutant forms of Alb58 were designed. Two of these mutants possessed a single amino acid change, Leu226→Gln (Alb58-QS mutant) and Ser228→Gly (Alb58-LG). The third mutant carried two amino acid changes, Leu226→Gln/Ser228→Gly (Alb58-QG).

Figure 6A:
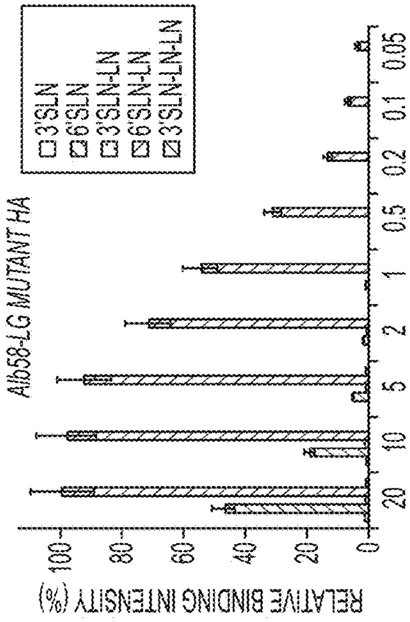
FIGS. 6A-D show exemplary glycan receptor-binding specificity of mutant forms of Alb58 HA.
Figure 6B:
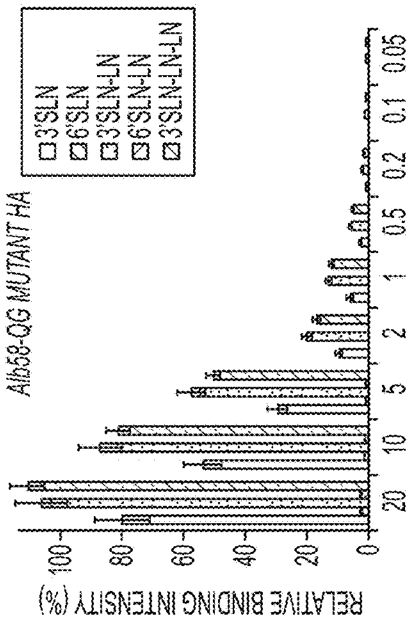
Figure 6C:
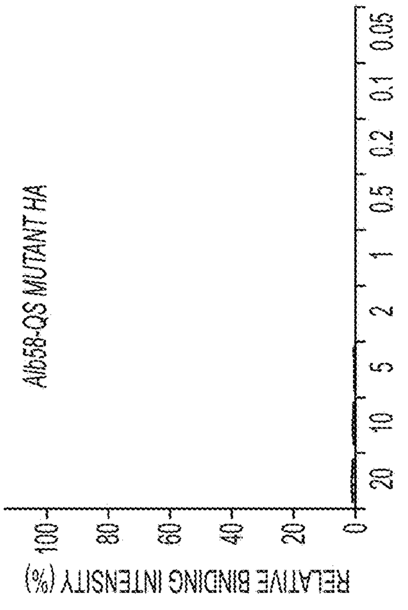
Figure 6D:
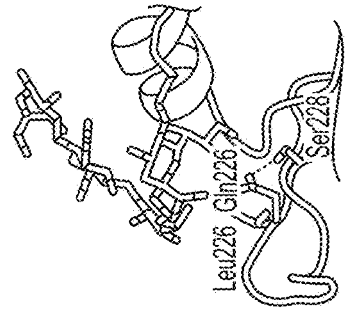

Alb58-LG mutant retained the human receptor binding specificity of the WT Alb58 HA but showed a complete loss in the avian receptor binding in the dose-dependent direct binding assay (FIG. 6A). On the other hand, Alb58-QG mutant showed a complete loss in human receptor binding and but displayed a substantial binding to avian receptors in contrast to Alb58 HA (FIG. 6B). Surprisingly, Alb58-QS mutant exhibited little to no binding to either the avian or human glycan receptor (FIG. 6C). Circular dichroism analysis of Alb58-QS ruled out the possibility of Alb58-QS being misfolded. A homology-based structural model of the Alb58-QS mutant was constructed to investigate the molecular basis of the observed biochemical binding property. Analysis of the glycan receptor-binding site of this mutant in the model showed that Ser228 is positioned to form a hydrogen bond with Gln226 (FIG. 6D). The interaction between Gln226 and Ser228 potentially disrupts the favorable positioning of Gln226 for optimal contact with avian receptor. This observation offers an explanation for the loss of avian receptor binding in the Alb58-QS mutant. Furthermore, the absence of contacts between Gln226 and human receptor could explain the loss of human receptor binding.

Mutations in RBS of CkPA04 and Their Effects on Its Glycan Receptor Binding Specificity.

Figure 7A:
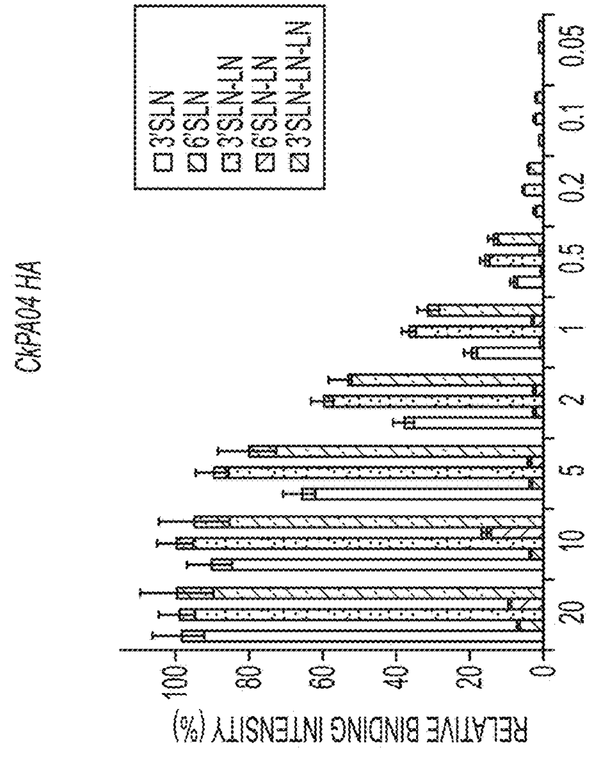
FIGS. 7A-B show exemplary glycan receptor-binding specificity of CkPA04 HA.
Figure 7B:
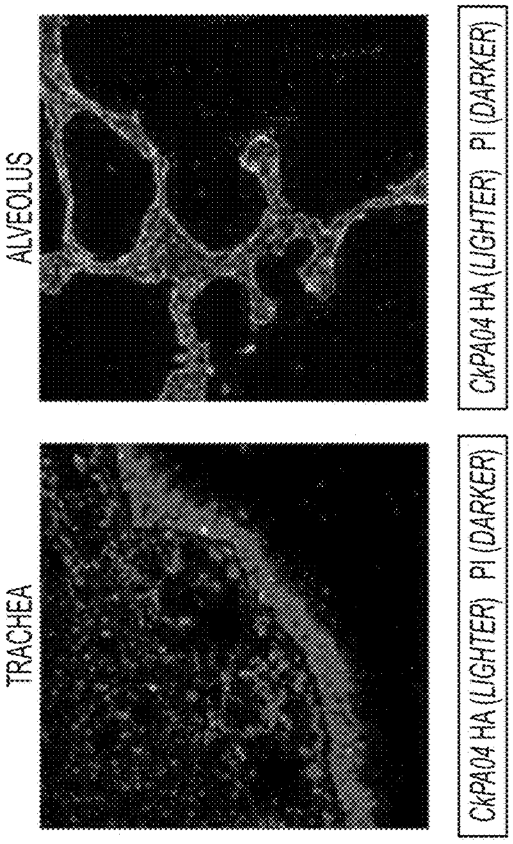

The dose-dependent glycan array binding of CkPA04 HA showed high affinity binding to the representative avian receptors 3'SLN, 3'SLN-LN and 3'SLN-LN-LN with minimal binding to human receptors (FIG. 7A). Furthermore, the glycan array binding property of CkPA04 correlated with its extensive binding to the human alveolar tissues and minimal binding to the apical side of the tracheal tissues (FIG. 7B).

Figure 8A:
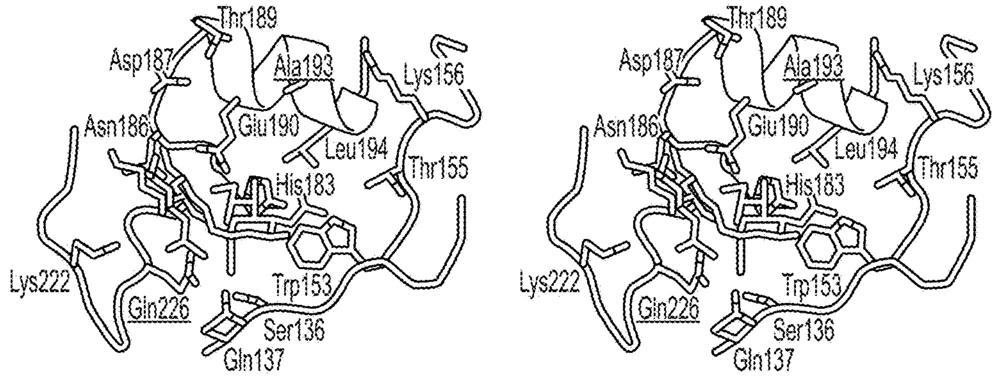
FIGS. 8A-B show exemplary_homology-based structural model of HA-glycan receptor complexes.
Figure 8B:
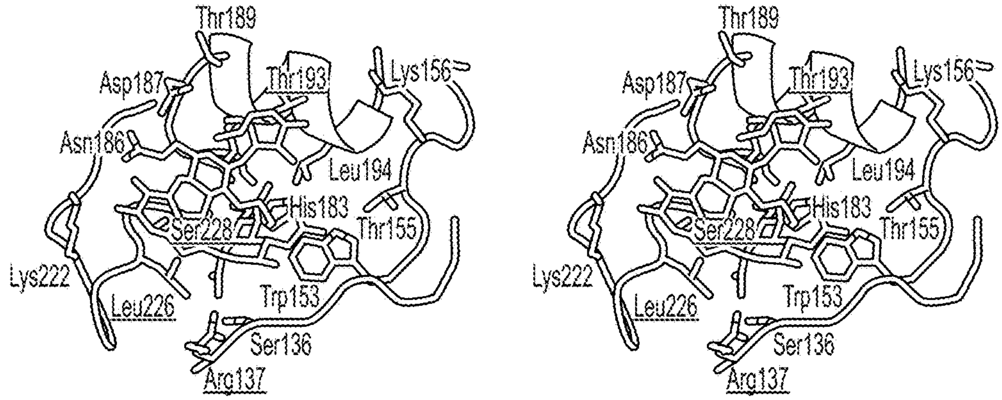

To understand the molecular aspects of the H2 HA-glycan receptor interaction, we constructed homology-based structural models of the CkPA04-avian (FIG. 8A) and the Alb58-human receptor complexes (FIG. 8B). Based on these structural models of CkPA04 and Alb58 HAs, the amino acids positioned to interact with the glycan receptors were compared (Table 7).

TABLE 7

Comparison of key amino acids in the RBS of CkPA04 and Alb58 HAs

| | 136 | 137 | 153 | 155 | 156 | 183 | 186 | 187 | 189 | 190 | 193 | 194 | 222 | 226 | 228 |
|---|---|---|---|---|---|---|---|---|---|---|---|---|---|---|---|
| CkPA04 | S | Q | W | T | K | H | N | D | T | E | A | L | K | Q | G |
| Alb58 | S | R | W | T | K | H | N | D | T | E | T | L | K | L | S |

In addition to the differences in 226 and 228 positions, there were differences in other positions including 137 and 193. The amino acids at positions 137 and 193 are oriented to interact with Neu5Acα2→6Gal motif as well as sugars beyond this motif in the context of the human receptor (and potentially play a role in antigenic variations among current strains of H2 viruses; see discussion). These differences potentially impinge on the human receptor binding of H2N2 HA. Notably, CkPA04 HA differs from earlier avian-adapted H2N2 HAs in the 137 and 193 positions. Therefore, while the Gln226→Leu and Gly228→Ser substitutions would make the RBS of earlier avian-adapted H2N2 HAs almost identical to that of the pandemic Alb58 HA, additional amino acid changes are required in the more recent avian-adapted HAs, including CkPA04.

Based on the above analysis, three sets of mutations were progressively made on CkPA04 to improve its contacts with the human receptor. The first mutant comprised of the two amino acid change Gln226→Leu/Gly228→Ser (CkPA04-LS). The second mutant, CkPA04-TLS, included an additional Ala193→Thr amino acid change in the CkPA04-LS HA. The third mutant, CkPA04-RTLS, was generated by introducing an additional Gln137→Arg mutation in the CkPA04-TLS HA. These HA mutants were recombinantly expressed and characterized in terms of their quantitative glycan receptor binding affinity and human tissue binding properties.

Figure 9A:
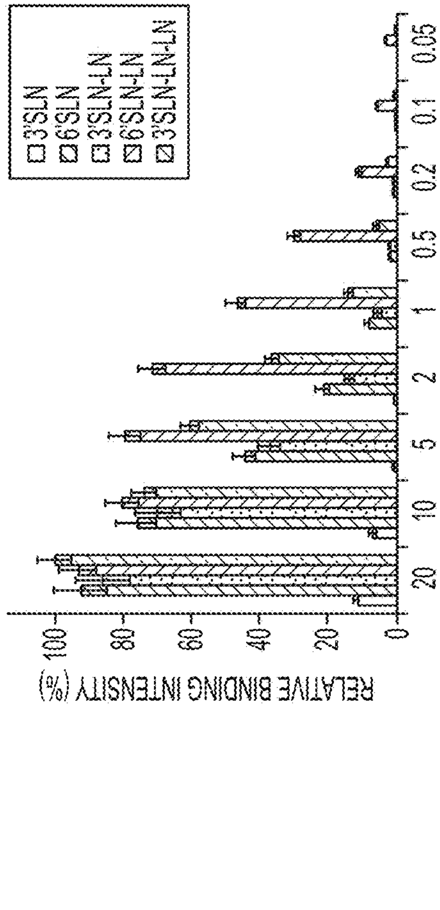
FIGS. 9A-F show exemplary glycan receptor-binding specificity of mutant forms of CkPA04 HA.
Figure 9B:
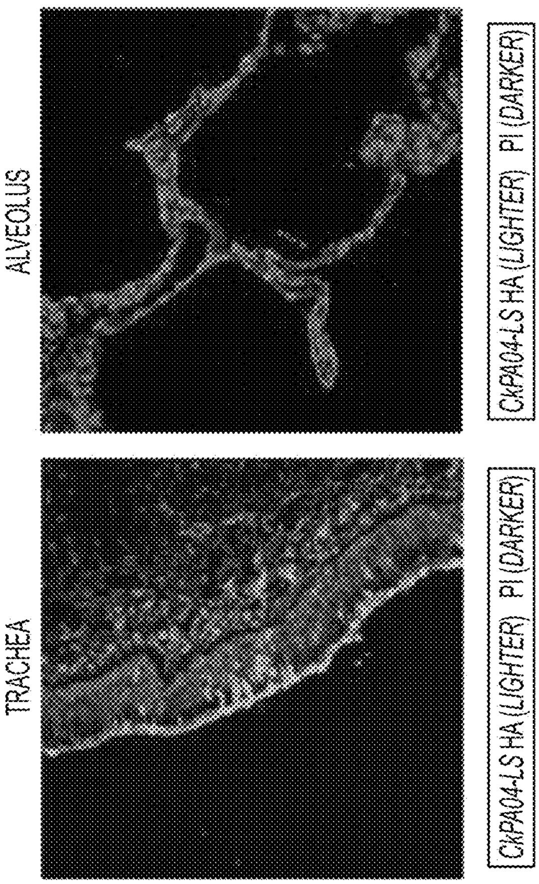
Figure 9C:
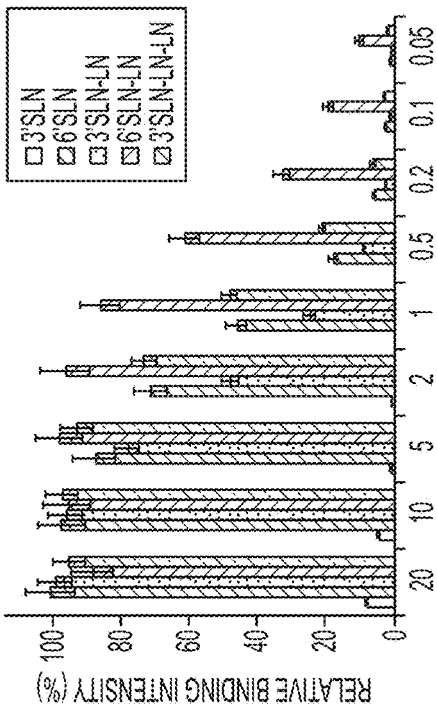
Figure 9D:
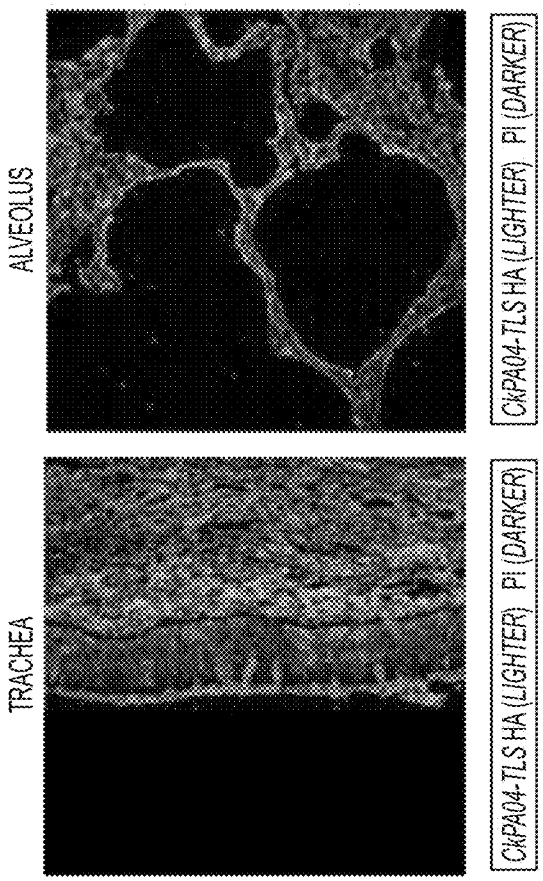
Figure 9F:
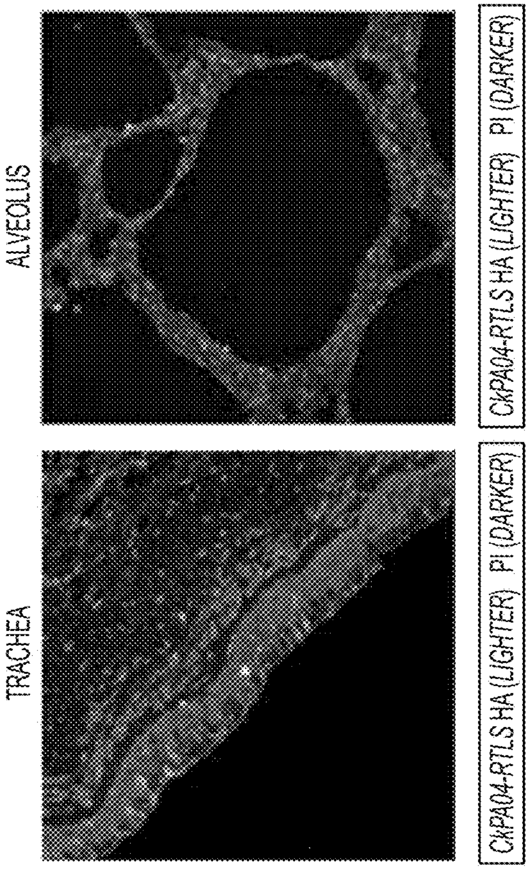
Figure 9E:
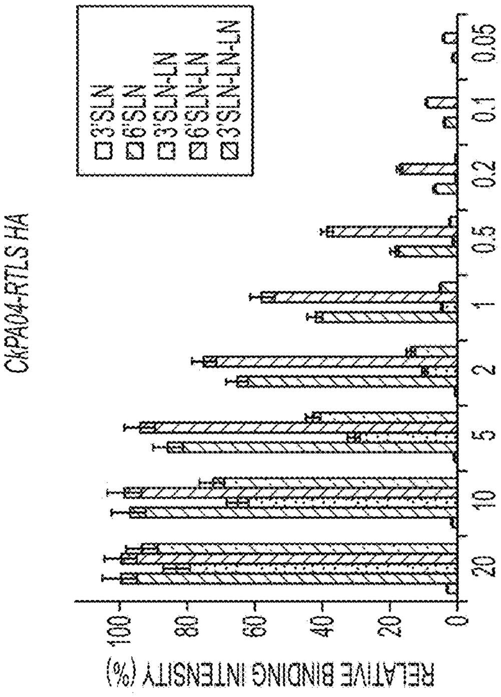
Figure 10A:
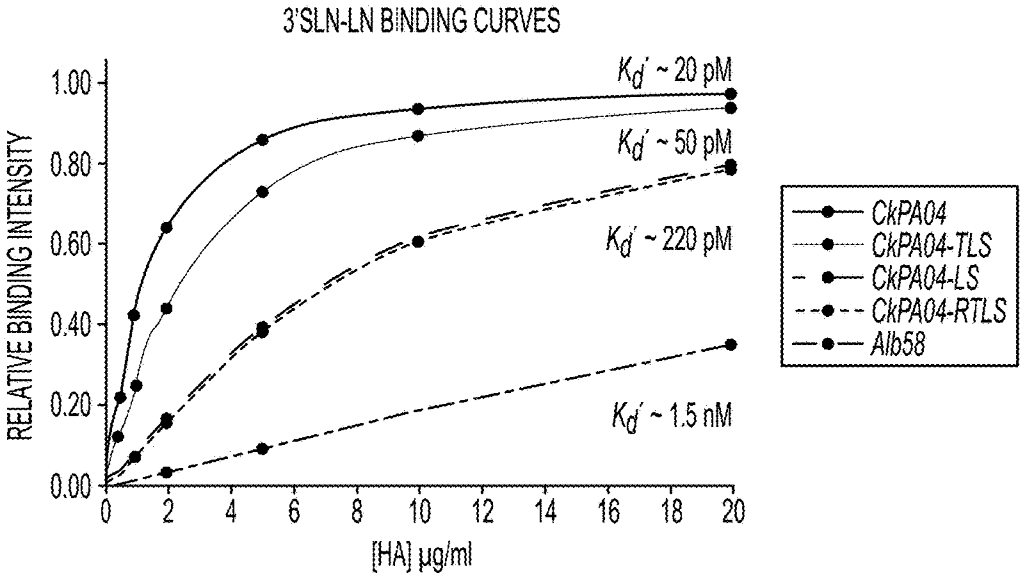
FIGS. 10A-B show exemplary glycan receptor-binding affinities of mutant forms of CkPA04 HA.
Figure 10B:
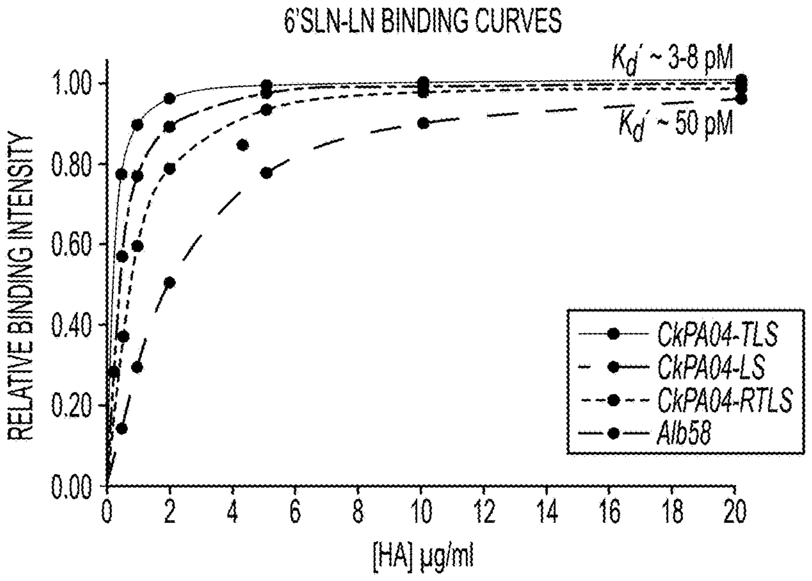
Figure 11A:
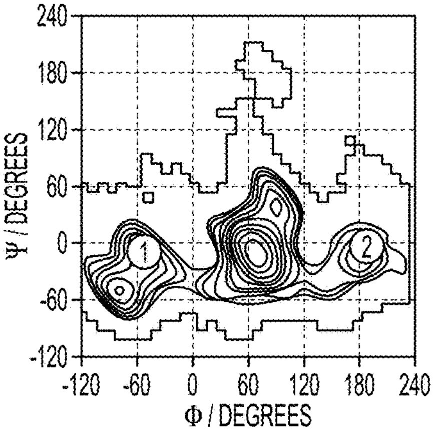
FIGS. 11A-D show conformational map and solvent accessibility of Neu5Acα2-3Gal and Neu5Acα2-6Gal motifs.
Figure 11B:
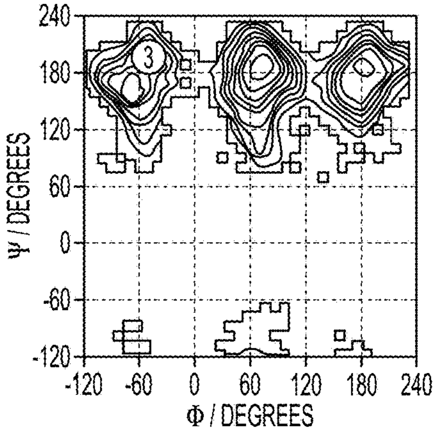
Figure 11C:
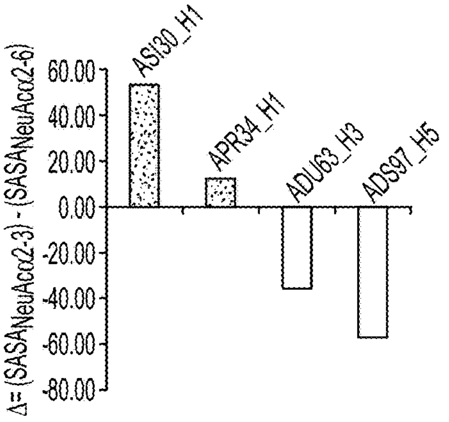
Figure 11D:
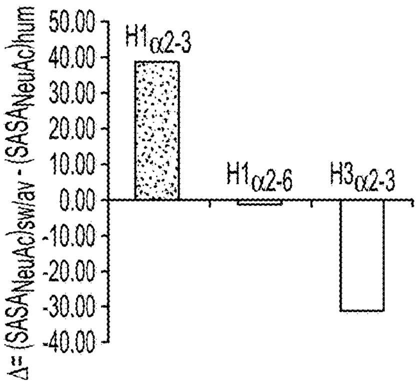

CkPA04-LS showed decreased binding to avian receptors and substantial binding to human receptors in comparison with CkPA04 (FIG. 9A). CkPA04-TLS showed substantially higher binding signals to both human and avian receptors when compared to CkPA04-LS (FIG. 9C). CkPA04-RTLS on the other hand showed increased binding signals to human receptor and similar binding signals to avian receptor as compared to CkPA04-LS (FIG. 9E). The human respiratory tissue binding of these mutant H2 HAs was in agreement with their observed glycan array binding (FIG. 9B, 9D, 9F). The dose-dependant glycan binding data of the described HAs were used to calculate Kd' and n values (n~1.3 for all the HAs) by fitting the binding data to the Hill equation (for multivalent binding) and this was then used to generate theoretical binding curves to clearly distinguish the relative binding affinities of WT and mutant H2 HAs to representative avian and human receptors (FIG. 10). The human receptor binding affinity of CkPA04-LS (Kd'~50 pM) was 10-fold lower than that of the Alb58 HA (Kd'~5 pM). On the other hand the human receptor binding affinity of both CkPA04-TLS (Kd'~3 pM) and CkPA04-RTLS (Kd'~8 pM) were several fold higher than that of CkPA04-LS and in the same range as that of Alb58 HA. The avian receptor binding affinity of CkPA04-TLS (Kd'~50 pM) was in the same range as that of the WT CkPA04 HA (Kd'~20 pM) and several fold higher than that of CkPA04-LS (Kd'~220 pM) and CkPA04-RTLS (Kd'~220 pM). Therefore, among the different mutants, CkPA04-RTLS was the closest to Alb58 HA in terms of its relative human to avian receptor binding affinity. Based on our structural understanding, this observation is consistent with the fact that the RBS of CkPA04-RTLS and Alb58 were very similar to each other, including extended range contacts with the glycan receptor beyond the Neu5Ac linkage.

Our study highlights the value of integrating a systematic sequence and structure analysis of HA-glycan molecular interactions and a quantitative binding assay to study the effects of these interactions on the biochemical glycan receptor binding affinity of HA.

Previous studies have focused on amino acid substitutions in 226 and 228 positions in the RBS of pandemic H2N2 HAs. Recently the glycan receptor-binding properties of the Alb58 virus and the WT and mutant forms (with substitutions in 226 and 228 positions in HA) of a related pandemic H2N2 virus—A/El Salvador/2/57 (or ElSalv57) were characterized by analyzing these whole viruses in a dose dependent fashion on the glycan array platform. The glycan receptor-binding properties of the recombinant Alb58 HA reported in the present study are in good agreement with those obtained using the whole viruses. Our results further augment these observations by characterizing the effect of substitutions in the 226 and 228 position on the quantitative glycan receptor binding affinity of Alb58 HA.

In addition to the previously noted 226 and 228 positions, our systematic sequence and structural analysis of H2 HA-glycan complexes revealed differences between CkPA04 and Alb58 HAs in other positions, such as 137 and 193. By progressively designing mutations in CkPA04 we have demonstrated that substitutions at the 137 and 193 positions (in addition to those in 226 and 228 positions) considerably alter the glycan receptor binding affinity. In fact, introducing these additional amino acid changes (CkPA04-TLS and CkPA04-RTLS mutants) leads to a 10-fold increase in the human receptor binding affinity compared to that of the CkPA04-LS mutant and makes the affinity in the range of that observed for the pandemic H2N2 HA (Alb58). Therefore, monitoring the mutations in these additional positions in the RBS is valuable for understanding changes in glycan receptor binding affinity of the H2 HAs. Moreover, these additional positions are also a part of antigenic loops and hence are likely to undergo constant substitutions as a result of antigenic drift in the H2 viruses to escape antibody neutralization. Monitoring these mutations also have important implications in vaccine development should a scenario arise wherein recent avian or swine H2 viruses are able to gain a foothold in the human population.

The apparent binding constant Kd' calculated in our study is used primarily to compare the relative binding affinities of different recombinant HAs by taking into account a defined spatial arrangement of HA (that is fixed for all the HAs) relative to the glycans. Among the various factors that influence the efficient viral transmissibility in humans we have shown in both the 1918 pandemic H1N1 and the recently declared 2009 pandemic H1N1 that the binding affinity to the human receptors (quantified using Kd') correlates with the transmissibility of the virus via respiratory droplets in ferrets. The human receptor binding affinity of Alb58 HA being in the same range as that of the SC18 HA taken together with the efficient respiratory droplet transmission of the Alb58 virus extends this correlation to the H2N2 viruses. Furthermore, given that Alb58 virus transmits efficiently via respiratory droplets in ferrets, our results underscores the fact that a complete switch from avian to human receptor binding is not the critical determinant for human adaptation of influenza A virus HAs. Both the quantitative glycan array binding and human tissue binding results of Alb58 HA show substantial avian receptor binding. Instead, it appears that the high affinity binding to human receptors is a common factor shared by H2 HA with that of other human-adapted virus subtypes (H1 and H3) and therefore this property appears to be an important determinant for efficient human adaptation and transmission. In summary our studies offer valuable strategies to monitor the evolution of human-adaptive mutations in the HA of currently circulating avian H2 influenza A viruses.

The present disclosure reports the first description of an H2 HA polypeptide characterized by the absolute and/or relative biding affinities reported herein. Now that the present disclosure has established that it is possible to provide such H2 HA polypeptides, those of ordinary skill in the art will appreciate that other H2 HA polypeptides, e.g., containing one or more sequence variations as compared with the specific sequences of H2 HA polypeptides explicitly tested herein, can be prepared that will similarly be characterized by such absolute and/or relative binding affinities. The present invention therefore provides H2 HA polypeptides characterized in that they show binding to umbrella topology glycans with high affinity.

For example, in some embodiments, H2 HA polypeptide binding to umbrella glycans is within a range of 10-fold or less (e.g., 9-fold, 8-fold, 7-fold, 6-fold, 5-fold, 4-fold, 3-fold, 2-fold, 1.5-fold, etc.) of the affinity for a wild type HA that mediates infection of a humans.

In some embodiments, H2 HA polypeptide binding to umbrella glycans has an affinity of at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100% of that observed under comparable conditions for a wild type HA that mediates infection of humans (e.g., is human transmissible).

In some embodiments, H2 HA polypeptides show a signal for binding to umbrella topology glycans above about 400000 or more (e.g., above about 500000, about 600000, about 700000, about 800000, etc) in a multivalent glycan array binding assay.

In some embodiments, H2 HA polypeptides show an affinity (Kd') for umbrella-topology glycans within the range of about 1.5 nM to about 2 pM. In some embodiments, H2 HA polypeptides show a Kd' for binding to cone-topology glycans of about 100 pM or more (e.g., above about 200 pM, about 300 pM, about 400 pM, about 500 pM, about 600 pM, about 700 pM, about 800 pM, about 900 pM, about 1 nM, about 1.1 nM, about 1.2 nM, about 1.3 nM, about 1.4 nM, about 1.5 nM, etc.) in binding assays. In some embodiments, H2 HA polypeptides show a Kd' of about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) for umbrella topology glycans and a Kd' of about 100 pM or more (e.g., above about 200 pM, about 300 pM, about 400 pM, about 500 pM, about 600 pM, about 700 pM, about 800 pM, about 900 pM, about 1 nM, about 1.1 nM, about 1.2 nM, about 1.3 nM, about 1.4 nM, about 1.5 nM, etc.) for cone topology glycans in binding assays.

In some embodiments, H2 HA polypeptides show a relative affinity for umbrella glycans vs cone glycans that is about 1, about 2, about 3, about 4, about 5, about 6, about 7, about 8, about 9, about 10, about 20, about 30, about 40, about 50, about 60, about 70, about 80, about 90, about 100, about 200, about 300, about 400, about 500, about 600, about 700, about 800, about 900, about 1000, about 2000, about 3000, about 4000, about 5000, about 6000, about 7000, about 8000, about 9000, about 10,000, up to about 100,000 or more. In some embodiments, H2 HA polypeptides show an affinity for umbrella topology glycans that is about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, about 10,000% or more than their affinity for cone topology glycans.

In some embodiments, H2 HA polypeptides bind to at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more of the glycans found on HA receptors in human upper respiratory tract tissues (e.g., epithelial cells).

In some embodiments, H2 HA polypeptides have an amino acid at a particular residue (e.g., 137, 145, 186, 187, 189, 190, 192, 193, 222, 225, 226, 228) that is predominantly present in the corresponding human-adapted HA (e.g., human-adapted H2 HA, such as those shown in FIG. 1). In some embodiments, provided HA polypeptides such as HA polypeptide variants (e.g., H2 HA polypeptides such as H2 HA polypeptide variants) have at least one amino acid substitution that is found in the corresponding human-adapted HA (e.g., human-adapted H2 HA). In some embodiments, H2 HA polypeptides have a sequence that differs from the wild-type H2 HA sequence.

Materials and Methods

Homology Based Modeling of CkPA04 HA- and Alb58 HA-Glycan Structural Complexes

The co-crystal structures of A/Singapore/1/57 H2N2 HA—human receptor (PDB ID: 2WR7) and A/ck/NewYork/91—avian receptor (PDB ID: 2WR2) were used as templates to model the structural complexes of Alb58—human receptor and CkPA04—avian receptor respectively. Homology modeling was performed using the SWISS-MODEL web-based program (URL: http://swissmodel.expasy.org/SWISS-MODEL.html).

Cloning, Mutagenesis and Expression of HA

The Alb58 and CkPA04 plasmids were gifts from Dr. Terrence Tumpey and Dr. Adolfo Garcia-Sastre respectively. The human and avian WT H2N2 HA genes were subcloned into a pAcGP67A vector to generate pAcGp67-Alb58-HA and pAcGp67-CkPA04-HA respectively for baculovirus expression in insect cells. Using pAcGp67-CkPA04-HA as a template the gene was mutated to yield pAcGp67-LS-HA [Gln226Leu, Gly228Ser], pAcGp67-TLS-HA [Ala193Thr, Gln226Leu, Gly228Ser] and pAcGp67-RTLS-HA [Gln137Arg, Ala193Thr, Gln226Leu, Gly228Ser]. The primers for mutagenesis were designed using PrimerX (http://bioinformatics.org/primerx/) and synthesized by IDT DNA technologies (Coralville, Iowa). The mutagenesis reaction was carried out using the QuikChange Multi Site-Directed Mutagenesis Kit (Stratagene, CA) Alb58, CkPA04, CkPA04-LS, CkPA04-TLS and CkPA04-RTLS baculoviruses were created from their respective plasmids, using Baculogold system (BD Biosciences, CA) as per the manufacturer's instructions. The baculoviruses were used to infect 300 ml suspension cultures of Sf9 cells (Invitrogen, Carlsbad, Calif.) cultured in Sf-900 II SFM medium (Invitrogen, Carlsbad, Calif.). The infected cultures were monitored and harvested 4-5 days post-infection. The soluble trimeric form of HA was purified from the supernatant of infected cells using modification of the protocol described previously. In brief, the supernatant was concentrated using Centricon Plus-70 centrifugal filters (Millipore, Billerica, Mass.) and the trimeric HA was recovered from the concentrated cell supernatant using affinity chromatography with columns packed with Ni-NTA beads (Qiagen, Valencia, Calif.). The fractions containing HA were pooled together and subjected to ultrafiltration using Amicon Ultra 100 K NMWL membrane filters (Millipore, Billerica, Mass.). The protein was reconstituted in PBS and concentrated. The purified protein concentration was determined using Bio-Rad's protein assay (Bio-Rad, CA).

Dose Dependent Direct Glycan Array-Binding Assay

To investigate the multivalent HA-glycan interactions a streptavidin plate array comprising representative biotinylated α2→3 and α2→6 sialylated glycans as described previously. The glycans 3'SLN, 3'SLN-LN, 3'SLN-LN-LN are representative avian receptors. 6'SLN and 6'SLN-LN are representative human receptors. LN corresponds to lactosamine (Galβ1-4GlcNAc) and 3'SLN and 6'SLN respectively correspond to Neu5Acα2-3 and Neu5Acα2-6 linked to LN. The biotinylated glycans were obtained from the Consortium of Functional Glycomics through their resource request program. Streptavidin-coated High Binding Capacity 384-well plates (Pierce) were loaded to the full capacity of each well by incubating the well with 50 μl of 2.4 μM of biotinylated glycans overnight at 4° C. Excess glycans were removed through extensive washing with PBS.

The trimeric HA unit comprises of three HA monomers (and hence three RBS, one for each monomer). The spatial arrangement of the biotinylated glycans in the wells of the streptavidin plate array favors binding to only one of the three HA monomers in the trimeric HA unit. Therefore in order to specifically enhance the multivalency in the HA-glycan interactions, the recombinant HA proteins were pre-complexed with the primary and secondary antibodies in the ratio of 4:2:1 (HA:primary:secondary). The identical arrangement of 4 trimeric HA units in the precomplex for all the HAs permits comparison between their glycan binding affinities.

A stock solution containing appropriate amounts of Histidine tagged HA protein, primary antibody (Mouse anti 6× His tag IgG) and secondary antibody (HRP conjugated goat anti Mouse IgG (Santacruz Biotechnology) in the ratio 4:2:1 and incubated on ice for 20 min. Appropriate amounts of precomplexed stock HA were diluted to 250 μl with 1% BSA in PBS. 50 μl of this precomplexed HA was added to each of the glycan-coated wells and incubated at room temperature for 2 hrs followed by the above wash steps. The binding signal was determined based on HRP activity using Amplex Red Peroxidase Assay (Invitrogen, CA) according to the manufacturer's instructions. The experiments were done in triplicate. Minimal binding signals were observed in the negative controls including binding of precomplexed unit to wells without glycans and binding of the antibodies alone to the wells with glycans. The binding parameters, cooperativity (n) and apparent binding constant (Kd'), for H2 HA-glycan binding were calculated by fitting the average signal value (from the triplicate analysis) and the HA concentration to the linearized form of the Hill equation:

$$\log\left(\frac{y}{1-y}\right) = n*\log([HA]) - \log(K_d'),$$

where y is the fractional saturation (average binding signal/maximum observed binding signal). The theoretical y values calculated using the Hill equation $$y = \frac{[HA]^n}{[HA]^n + K_d'}$$

(for the set of n and Kd' parameters) were plotted against the varying concentration of HA to obtain the binding curves for representative human (6'SLN-LN) and avian receptors (3'SLN-LN) shown in FIG. 10.

Human Respiratory Tissue Binding Assay

Formalin fixed and paraffin embedded normal human tracheal and alveolar tissue sections were purchased from US Biological and US Biomax, respectively. Tissue sections were incubated for 30 minutes in a hybridization oven at 60° C. to melt the paraffin. Excess paraffin was removed by multiple washes in xlyene. Sections were subsequently rehydrated in a series of ethanol washes. In order to prevent nonspecific binding, sections were pre-blocked with 1% BSA in PBS for 30 minutes at room temperature (RT). For the generation of HA-antibody precomplexes, the histidine tagged purified recombinant HAs (Alb58, CkPA04, LS and TLS) were incubated with primary antibody against his tag (mouse anti 6× His tag, Abcam) and secondary (Alexa Fluor 488 goat anti mouse IgG, Invitrogen) antibody in a ratio of 4:2:1 respectively for 20 minutes on ice. Tissue sections were incubated with the HA-antibody precomplexed unit, diluted to different final concentrations in 1% BSA-PBS, for 3 hours at RT. Sections were then incubated with propidium iodide to counterstain the nuclei (Invitrogen; 1:100 in TBST) for 20 minutes at RT. After thorough washing, sections were mounted and analyzed using a Zeiss LSM510 laser scanning confocal microscope.

REFERENCES

1. Makarova N V, Kaverin N V, Krauss S, Senne D, Webster R G (1999) Transmission of Eurasian avian H2 influenza virus to shorebirds in North America. J Gen Virol 80 (Pt 12): 3167-3171.
2. Schafer J R, Kawaoka Y, Bean W J, Suss J, Senne D, et al. (1993) Origin of the pandemic 1957 H2 influenza A virus and the persistence of its possible progenitors in the avian reservoir. Virology 194: 781-788.
3. Ma W, Vincent A L, Gramer M R, Brockwell C B, Lager K M, et al. (2007) Identification of H2N3 influenza A viruses from swine in the United States. Proc Natl Acad Sci USA 104: 20949-20954.
4. Russell C J, Webster R G (2005) The genesis of a pandemic influenza virus. Cell 123: 368-371.
5. Tumpey T M, Basler C F, Aguilar P V, Zeng H, Solorzano A, et al. (2005) Characterization of the reconstructed 1918 Spanish influenza pandemic virus. Science 310: 77-80.
6. Yen H L, Webster R G (2009) Pandemic influenza as a current threat. Curr Top Microbiol Immunol 333: 3-24.
7. Basler C, Palese P (2002) Influenza Viruses. In: Creighton T, editor. Encyclopedia of Molecular Medicine. New York: John Wiley and Sons. pp. 1741-1747.
8. Skehel J J, Wiley D C (2000) Receptor binding and membrane fusion in virus entry: the influenza hemagglutinin. Annu Rev Biochem 69: 531-569.
9. Shriver Z, Raman R, Viswanathan K, Sasisekharan R (2009) Context-specific target definition in influenza a virus hemagglutinin-glycan receptor interactions. Chem Biol 16: 803-814.
10. Chandrasekaran A, Srinivasan A, Raman R, Viswanathan K, Raguram S, et al. (2008) Glycan topology determines human adaptation of avian H5N1 virus hemagglutinin. Nat Biotechnol 26: 107-113.
11. Shinya K, Ebina M, Yamada S, Ono M, Kasai N, et al. (2006) Avian flu: influenza virus receptors in the human airway. Nature 440: 435-436.
12. van Riel D, Munster V J, de Wit E, Rimmelzwaan G F, Fouchier R A, et al. (2007) Human and Avian Influenza Viruses Target Different Cells in the Lower Respiratory Tract of Humans and Other Mammals. Am J Pathol. 171: 1215-23
13. Gambaryan A S, Tuzikov A B, Bovin N V, Yamnikova S S, Lvov D K, et al. (2003) Differences between influenza virus receptors on target cells of duck and chicken and receptor specificity of the 1997 H5N1 chicken and human influenza viruses from Hong Kong. Avian Dis 47: 1154-1160.
14. Xu D, Newhouse E I, Amaro R E, Pao H C, Cheng L S, et al. (2009) Distinct glycan topology for avian and human sialopentasaccharide receptor analogues upon binding different hemagglutinins: a molecular dynamics perspective. J Mol Biol 387: 465-491.
15. Wei C J, Boyington J C, Dai K, Houser K V, Pearce M B, et al. (2010) Cross-neutralization of 1918 and 2009 influenza viruses: Role of glycans in viral evoluion and vaccine design. Sci Transl Med 2, 24ra21
16. Childs R A, Palma A S, Wharton S, Matrosovich T, Liu Y, et al. (2009) Receptor-binding specificity of pandemic influenza A (H1N1) 2009 virus determined by carbohydrate microarray. Nat Biotechnol 27: 797-799.
17. Stevens J, Blixt O, Chen L M, Donis R O, Paulson J C, et al. (2008) Recent avian H5N1 viruses exhibit increased propensity for acquiring human receptor specificity. J Mol Biol 381: 1382-1394.
18. Stevens J, Blixt O, Paulson J C, Wilson I A (2006) Glycan microarray technologies: tools to survey host specificity of influenza viruses. Nat Rev Microbiol 4: 857-864.
19. Maines T R, Jayaraman A, Belser J A, Wadford D A, Pappas C, et al. (2009) Transmission and pathogenesis of swine-origin 2009 A(H1N1) influenza viruses in ferrets and mice. Science 325: 484-487.
20. Hensley S E, Das S R, Bailey A L, Schmidt L M, Hickman H D, et al. (2009) Hemagglutinin receptor binding avidity drives influenza A virus antigenic drift. Science 326: 734-736.
21. Srinivasan A, Viswanathan K, Raman R, Chandrasekaran A, Raguram S, et al. (2008) Quantitative biochemical rationale for differences in transmissibility of 1918 pandemic influenza A viruses. Proc Natl Acad Sci USA 105: 2800-2805.
22. Van Hoeven N, Pappas C, Belser J A, Maines T R, Zeng H, et al. (2009) Human HA and polymerase subunit PB2 proteins confer transmission of an avian influenza virus through the air. Proc Natl Acad Sci USA 106: 3366-3371.

23. Itoh Y, Shinya K, Kiso M, Watanabe T, Sakoda Y, et al. (2009) In vitro and in vivo characterization of new swine-origin H1N1 influenza viruses. Nature 460: 1021-1025.
24. Wan H, Sorrell E M, Song H, Hossain M J, Ramirez-Nieto G, et al. (2008) Replication and transmission of H9N2 influenza viruses in ferrets: evaluation of pandemic potential. PLoS ONE 3: e2923.
25. Tumpey T M, Maines T R, Van Hoeven N, Glaser L, Solorzano A, et al. (2007) A two-amino acid change in the hemagglutinin of the 1918 influenza virus abolishes transmission. Science 315: 655-659.
26. Maines T R, Chen L M, Matsuoka Y, Chen H, Rowe T, et al. (2006) Lack of transmission of H5N1 avian-human reassortant influenza viruses in a ferret model. Proc Natl Acad Sci USA 103: 12121-12126.
27. Xu R, McBride R, Paulson J C, Basler C F, Wilson I A (2009) Structure, receptor binding and antigenicity of influenza virus hemagglutinins from the 1957 H2N2 pandemic. J Virol.
28. Liu J, Stevens D J, Haire L F, Walker P A, Coombs P J, et al. (2009) Structures of receptor complexes formed by hemagglutinins from the Asian Influenza pandemic of 1957. Proc Natl Acad Sci USA 106: 17175-17180.
29. Glaser L, Zamarin D, Acland H M, Spackman E, Palese P, et al. (2006) Sequence analysis and receptor specificity of the hemagglutinin of a recent influenza H2N2 virus isolated from chicken in North America. Glycoconj J 23: 93-99.
30. Pappas C, Viswanathan K, Chandrasekaran A, Raman R, Katz J, et al. (2010) Receptor specificity and transmission of H2N2 subtype viruses isolated from the pandemic of 1957. PLoS ONE (In Press).
31. Stevens J, Corper A L, Basler C F, Taubenberger J K, Palese P, et al. (2004) Structure of the uncleaved human H1 hemagglutinin from the extinct 1918 influenza virus. Science 303: 1866-1870.

Example 2

Testing Inventive Binding Agents in an Animal Host

As described herein, the present invention encompasses the recognition that the use of animal hosts (e.g., ferrets) for the study of transmission of virus may provide a reliable indicator of human virus transmission. Similarly, the present invention encompasses the recognition that the use of animal hosts (e.g., ferrets) treated with inventive binding agents (e.g., HA polypeptides) for the study of transmission of virus may provide a reliable indicator of the efficacy of such inventive binding agents for prevention or treatment of virus in a human host.

The present Example describes a virus transmission assay that can be used in the presence or absence of inventive binding agents to determine viral transmission in a suitable animal model. Animal hosts, e.g., ferrets, can be housed in adjacent cages that prevent direct and indirect contact between animals. However, these housing conditions allow the spread of influenza virus through the air. A first portion of the animals are inoculated via methods known in the art, e.g., intranasally, with an effective amount of virus ("inoculated animals"). Naïve animals can then be introduced into cages adjacent to the inoculated animals one, two, three or more days later.

Animals used in the study can be killed at any time one, two, three or more days post-inoculation or transmission for analysis. Suitable analysis for virus transmission studies can include, but is not limited to determination of infectious virus titers (e.g., by nasal washes), observation of physical symptoms in the animals (e.g., lethargy, anorexia, rhinorrhea, sneezing, high fever, and/or death), immunohistochemical analysis of respiratory tissues, among others.

The virus transmission assay described above can also incorporate the treatment of the animal host with an inventive binding agent described herein before, during or after inoculation or transmission of virus. Analytic methods described herein are then used to determine the efficacy of the binding agent(s) in blocking transmission and/or infection of the animal host with the virus.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A monoclonal antibody that binds specifically to an HA polypeptide variant relative to that of reference HA from avian influenza strain A/Chicken/Pennsylvania/2004, wherein the HA polypeptide variant has an amino acid sequence that shows at least 90% overall sequence identity with a reference HA polypeptide of SEQ ID NO:1, which HA polypeptide variant is characterized in that its amino acid sequence includes:

an amino acid residue ("Residue 137") at a position corresponding to HA position 137 of SEQ ID NO:1 that is arginine;

an amino acid residue ("Residue 193") at a position corresponding to HA position 193 of SEQ ID NO:1 that is threonine;

an amino acid residue ("Residue 226") at a position corresponding to HA position 226 of SEQ ID NO:1 that is leucine; and an amino acid residue ("Residue 228") at a position corresponding to HA position 228 of SEQ ID NO:1 that is serine.

2. A method of using the antibody of claim 1 to detect the HA polypeptide in a sample.

3. The method of claim 2, wherein the sample is an environmental sample.

4. The method of claim 3, wherein the environmental sample is or comprises one or more of soil, water and flora.

5. The method of claim 2, wherein the sample is a pathological sample.

6. The method of claim 5, wherein the pathological sample is or comprises blood, serum, plasma, peripheral blood mononuclear cells, peripheral blood lymphocytes (PBMC/PBL), sputum, urine, feces, throat swabs, dermal lesion swabs, cerebrospinal fluids, cervical smears, pus samples, food matrices, and tissues.

* * * * *

UNITED STATES PATENT AND TRADEMARK OFFICE
CERTIFICATE OF CORRECTION

Page 1 of 1

PATENT NO. : 9,745,352 B2
APPLICATION NO. : 14/341285
DATED : August 29, 2017
INVENTOR(S) : Raman et al.

It is certified that error appears in the above-identified patent and that said Letters Patent is hereby corrected as shown below:

In the Specification

In Column 1, Lines 11-14, delete:
"This invention was made with government support under Grant Nos. R37 GM057073 and U54 GM2116 awarded by the National Institutes of Health. The government has certain rights in this invention."

And insert:
-- This invention was made with government support under R37 GM057073 and U54 GM062116 awarded by the National Institutes of Health. The government has certain rights in the invention. --

Signed and Sealed this
Fourth Day of November, 2025

John A. Squires
*Director of the United States Patent and Trademark Office*